US009815895B2

(12) United States Patent
Koike et al.

(10) Patent No.: US 9,815,895 B2
(45) Date of Patent: *Nov. 14, 2017

(54) METHODS OF REDUCING BASOPHIL LEVELS

(71) Applicants: BIOWA, INC., Princeton, NJ (US); ASTRAZENECA AB, Södertälje (SE)

(72) Inventors: Masamichi Koike, West Windsor, NJ (US); George L. Spitalny, Yardley, PA (US); Alistair Wheeler, Northborough, MA (US); Barbara White, Finksburg, MD (US)

(73) Assignees: BIOWA, INC., Princeton, NJ (US); ASTRAZENECA AB, Södertälje (SE)

( * ) Notice: Subject to any disclaimer, the term of this patent is extended or adjusted under 35 U.S.C. 154(b) by 328 days.

This patent is subject to a terminal disclaimer.

(21) Appl. No.: 13/934,271

(22) Filed: Jul. 3, 2013

(65) Prior Publication Data

US 2014/0004109 A1 Jan. 2, 2014

Related U.S. Application Data

(63) Continuation of application No. 13/177,221, filed on Jul. 6, 2011, now Pat. No. 8,501,176, which is a continuation of application No. 12/600,017, filed as application No. PCT/US2008/006156 on May 14, 2008, now abandoned.

(60) Provisional application No. 60/924,422, filed on May 14, 2007, provisional application No. 60/924,832, filed on Jun. 1, 2007, provisional application No. 60/935,005, filed on Jul. 20, 2007, provisional application No. 61/064,612, filed on Mar. 14, 2008.

(51) Int. Cl.

| *A61K 39/395* | (2006.01) |
| *C07K 16/00* | (2006.01) |
| *C07K 16/28* | (2006.01) |
| *C07K 7/08* | (2006.01) |
| *A61K 39/00* | (2006.01) |

(52) U.S. Cl.
CPC ............. *C07K 16/28* (2013.01); *C07K 7/08* (2013.01); *C07K 16/2866* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| 6,018,032 | A | 1/2000 | Koike et al. |
| 6,538,111 | B1 | 3/2003 | Koike et al. |
| 6,946,292 | B2 | 9/2005 | Kanda et al. |
| 7,179,464 | B2 | 2/2007 | Koike et al. |
| 7,214,775 | B2 | 5/2007 | Hanai et al. |
| 7,238,354 | B2 | 7/2007 | Koike et al. |
| 7,393,683 | B2 | 7/2008 | Kanda et al. |
| 7,404,953 | B2 | 7/2008 | Hosaka et al. |
| 7,425,446 | B2 | 9/2008 | Kanda et al. |
| 7,662,925 | B2 * | 2/2010 | Lazar et al. ............... 530/387.1 |
| 7,708,992 | B2 | 5/2010 | Hanai et al. |
| 7,718,175 | B2 | 5/2010 | Hanai et al. |
| 7,737,325 | B2 | 6/2010 | Kanda et al. |
| 7,741,442 | B2 | 6/2010 | Kanda et al. |
| 7,846,725 | B2 | 12/2010 | Kanda et al. |
| 8,501,176 | B2 * | 8/2013 | Koike et al. ............... 424/133.1 |
| 2006/0014680 | A1 | 1/2006 | Xu et al. |
| 2006/0063254 | A1 | 3/2006 | Kanda et al. |
| 2007/0003546 | A1 | 1/2007 | Lazar et al. |

FOREIGN PATENT DOCUMENTS

| EP | 1266663 A1 | 12/2002 |
| EP | 1688437 A1 | 8/2006 |
| WO | WO97/10354 | 3/1997 |
| WO | WO00/61739 | 10/2000 |
| WO | WO 01/60405 A1 | 8/2001 |
| WO | WO2007/041635 A2 | 4/2007 |

OTHER PUBLICATIONS

Garrett et al., Anti-interleukin-5 (mepolizumab) therapy for hypereosinophilic syndromes. J. Allergy Clin. Immunol. 113:115-119, 2004.*
Bowie et al. Deciphering the Message in Protein Sequences: Tolerance to Amino Acid Substitutions. Science, 247:1306-1310, 1990.*
Greenspan et al. Defining epitopes: It's not as easy as it seems. Nature Biotechnology 7: 936-937, 1999.*
Burgess et al. Possible dissociation of the heparin-binding and mitogenic activities of heparin-binding (acidic fibroblast) growth factor-1 from its receptor-binding activties by site-directed mutagensis of a single lysine residue. Journal of Cell Biology, 111:2129-2138, 1990.*
Lazar et al. Transforming growth factor alpha: Mutation of aspartic acid 47 and leucine 48 results in different biological activites. Molecular Cellular Biology, 8:1247- 1252, 1988.*
Yu et al. Interaction between Bevacizumab and murine VEGF-A: a reassessment. Investigative Ophthalmology & Visual Science, 2008; 49(2): 522-527).*
Kolbeck et al. MEDI-563, a humanized anti-IL-5 receptor alpha mAb with enhanced antibody-dependent cell-mediated cytotoxicity function. Journal of Clinical Immunology, 2010; 125(6): 1344-53.*

(Continued)

*Primary Examiner* — Vanessa L Ford
*Assistant Examiner* — Sandra Dillahunt

(57) ABSTRACT

The present invention relates to a method of reducing the numbers of eosinophils in a human subject comprising administration to a subject an IL-5R binding molecule that comprises (a) a region that specifically binds to the IL-5R and (b) an immunoglobulin Fc region. In a specific embodiment, a method of the invention reduces the number of eosinophils in blood, bone marrow, gastrointestinal tract (e.g. esophagus, stomach, small intestine and colon), or lung.

6 Claims, 47 Drawing Sheets

(56) References Cited

OTHER PUBLICATIONS

Busse et al. Safety profile, pharmacokinetics, and biologic activity of MEDI-563, an anti-IL-5 receptor alpha antibody, in a phase I study of subjects with mild asthma. Journal of Allergy and Clinical Immunology; 2010; (125(6): 1237-1244.*

Chihara, Junichi et al., 1990, "Characterization of a Receptor for Interleukin 5 on Human Eosinophils: Variable Expression and Induction by Granulocyte/Macrophage Colony-stimulating Factor", J. Exp. Med., 172:1347-1351.

Corrigan, C.J. et al., 1992, "T cells and eosinophils in the pathogenesis of asthma", Immunology Today, 13(12): 501-506.

Ema, Hideo et al., 1990, "Target Cells for Granulocyte Colony-Stimulating Factor, Interleukin-3, and Interleukin-5 in Differentation Pathways of Neutrophils and Eosinophils", 76(10): 1956-1961.

Farinacci, Charles J. et al., 1951, "Eosinophilic Granuloma of the Lung", United States Armed Forces Medical Journal, vol. 11(7):1085-1093.

Fauci, Anthony S. et al., 1982, "The Idiopathic Hypereosinophilic Syndrome", Annals of Internal Medicine, 97:78-92.

Fukuda, Takeshi et al., 1985, "Increased Numbers of Hypodense Eosinophils in the Blood of Patients with Bronchial Asthma", Am. Rev. Respir. Dis. 132:981-985.

Garrett, Jennifer K. Et al., 2004, "Anti-interleukin-5 (mepolizumab) therapy for hypereosinophilic syndromes", J. Allergy Clin. Immunol. 113:115-119.

Gleich, Gerald J. et al., 1986, "The Eosinophilic Leukocyte: Structure and Function", Advances in Immunology, 39:177-253.

Gruart, Valerie et al., 1989, "Variations in Protein Expression Related to Human Eosinophil Heterogeneity", The Journal of Immunology, 142:4416-4421.

Harley, John B. et al., 1983, "Noncardiovascular Findings Associated With Heart Disease in the Idiopathic Hypereosinophilic Syndrome", Am. J. Cardiol., 52:321-324.

Ishino, Tetsuya et al., 2004, "Kinetic Interaction Analysis of Human Interleukin 5 Receptor α Mutants Reveals a Unique Binding Topology and Charge Distribution for Cytokine Recognition", J. Biol. Chem., 279(10):9547-9556.

International Search Report dated Sep. 25, 2008.

Owen, William F. et al., 1989, "Interleukin 5 and Phenotypically Altered Eosinophils in the Blood of Patients With the Idiopathicf Hypereosinophilic Syndrome", J. Exp. Med., 170:343-348.

Rothenberg, Marc. E. et al., 1988, "Human Eosinophils Have Prolonged Survival, Enhanced Functional Properties, and Become Hypodense When Exposed to Human Interleukin 3", J. Clin. Invest., 81:1986-1992.

Saito, Hirohisa et al., 1988, "Selective differentiation and proliferation of hematopoietic cells induced by recombinant human interleukins", Proc. Natl. Acad. Sci. USA, 85:2288-2292.

Saita, Naoki et al., 1999, "Difference in Apoptotic Function between Eosinophils from Peripheral Blood and Bronchoalveolar Lavage in Chronic Eosinophilic Pneumonia", Int. Arch. Allergy Immunol., 120:91-94.

Spry, C.J.F. et al., 1976, "Studies on blood eosinophils", Clin. Exp. Immunol. 24:423-434.

Tai, P.C., et al., 1991, "Effects of IL-5, granulocyte/macrophage colony-stimulating factor (GM-CSF) and IL-3 on the survival of human blood eosinophils in vitro", Clin. Exp. Immunol., 85:312-316.

Teran, L. M., et al., 1996, "The chemokines: their potential role in allergic inflammation", Clinical and Experimental Allergy, 26:1005-1019.

Winqvist, I. et al., 1982, "Altered density, metabolism and surface receptors of eosinophils in eosinophilia", Immunology, 47:531-539.

Lazar, GA et al., 2006 "Engineered antibody Fc variants with enhanced effector function", Proceedings of the National Academy of Sciences, vol. 103, No. 11, pp. 4005-4010.

Siberil, Sophie et al.., 2007, "FcgammaR: The Key to Optimize Therapeutic Antibodies?", Critical Reviews in Oncology/Hematology, Elsevier Science Ireland Ltd., Limerick, IE., vol. 62, No. 1, pp. 26-33.

Supplementary European Search Report for EP 08779619 dated May 12, 2012.

English Translation of Kyowa Hakko, Clinical study on an antibody medicinal product for treating asthma, over 6 years by the US subsidiary, Chemical Daily, Nov. 2, 2005, Chemical Daily p. 6, (No. 378).

English Translation of Official Action dated Apr. 2, 2013 for corresponding Japanese Application No. 2010-508412.

* cited by examiner

MEDI-563 Binding to rhuIL-5Rα

| | Format | Instrument | kon (1/Ms) | koff (1/sec) | $K_D$ (nM) |
|---|---|---|---|---|---|
| | | | (xe+5) | (xe-3) | |
| Experiment 0 | Capture | 3000 | 7.4 | 2.1 | 2.9 |
| Experiment 1 | rhIL-5Ra-down | 3000 | 5.16* (5.06/5.26) | 1.11* (0.79/1.42) | 2.13* (1.57/2.69) |
| Experiment 2 | Capture | T100 | 3.03* (2.79/3.27) | 1.92* (1.82/2.02) | 6.35* (6.52/6.18) |

Fig. 10

MEDI-563 Binding to rhuFcγRs

| Test Reagent | [Batch] | Fc Receptor | Fc Lot | $K_D$ (nM) |
| --- | --- | --- | --- | --- |
| BIW8405 | 5mg/mL | huFcgRIIb - | 5/7/07 | 5730 |
| BIW8405 | 5mg/mL | huFcgRIIIA - 158F | 5/1/06 | 4760 |
| BIW8405 | 5mg/mL | huFcgRIIIA - 158V | R22K ZZ3401-03 | 46 |
| BIW8405 | 5mg/mL | huFcRI - | 3/7/06 | 16 |
| BIW8405 | 5mg/mL | huFcRIIA - | 3/7/06 | 1290 |
| BIW8405 | 5mg/mL | muFcgRIIb - | KB031407 | 1100 |
| BIW8405 | 5mg/mL | muFcgRIII - | KS032307 | 4930 |
| BIW8405 | 5mg/mL | muFcgRIV - | KS032307 | 32 |
| Control | 5mg/mL | huFcgRIIb - | 5/7/07 | 14500 |
| Control | 5mg/mL | huFcgRIIIA - 158F | 5/1/06 | 0 |
| Control | 5mg/mL | huFcgRIIIA - 158V | R22K ZZ3401-03 | 574 |
| Control | 5mg/mL | huFcRI - | 3/7/06 | 19 |
| Control | 5mg/mL | huFcRIIA - | 3/7/06 | 1280 |
| Control | 5mg/mL | muFcgRIIb - | KB031407 | 1470 |
| Control | 5mg/mL | muFcgRIII - | KS032307 | 6360 |
| Control | 5mg/mL | muFcgRIV - | KS032307 | 329 |

Fig. 11

```
                          Segment A                                    Segment B
Human  1   DLL PDEKIS LLPPVNFTIKV TGLAQVLLQWK PNPDQEQR NVNLEYQVKINAPKEDDYETR
           DLL +K     LLPPVNFTIK  TGLAQVLL W   PNPDQEQR+V+LEY  VKINAP+ED+Y+TR
Mouse  1   DLLNHKKFLLLPPVNFTIKATGLAQVLLHWDPNPDQEQRHVDLEYHVKINAPQEDEYDTR Segment C
Human  61  IT ESKCVT ILHKGFSASVRTIL QNDHSLLASSWASAELH APP   102
           +T  SKCVT  LH+GF+ASVRTIL++   H+ LASSW SAEL  APP
Mouse  61  KTESKCVTPLHEGFAASVRTIILKSSHTTLASSWVSAELKAPP       102

Comparison of Domain 1 of IL5Rα Between Human and Mouse : 75% (identity)

Fig. 26A
```

Knock-out mutants -Substitute human (*hu*) residues in segment A,B,C with mouse counterparts muA *huB* *huC*
*huA* muB *huC*
*huA* *huB* muC

Knock-in mutants -Substitute murine (mu) residues in segment A,B,C with human counterparts

*huA* muB muC
muA *huB* muC
muA muB *huC*

Knock-in & Knock-out constructs
```
40 NVNLEYQVKINAPKEDDYETRI 61
              IL5 binding site
N-N---Q                          = NNQ
--------------K--D-E--I          = KDEI
-----------------D-E---          = DE
N-N--------------D-E---          = NNDE
```
- Amino acid sequence of human Segment B1 of the D1 extracellular domain of IL-5Ralpha is shown.
- Residues in *italics* are different beween human and mouse.
- Underlined residues are contributing to ligand binding (Chaiken I., et al. JBC 2004,279).

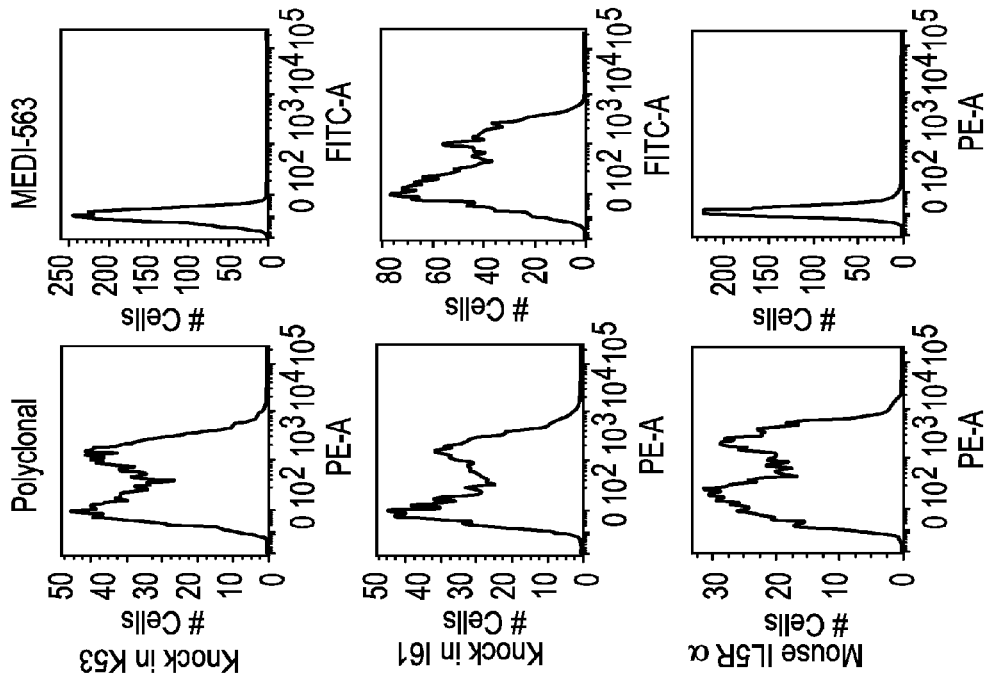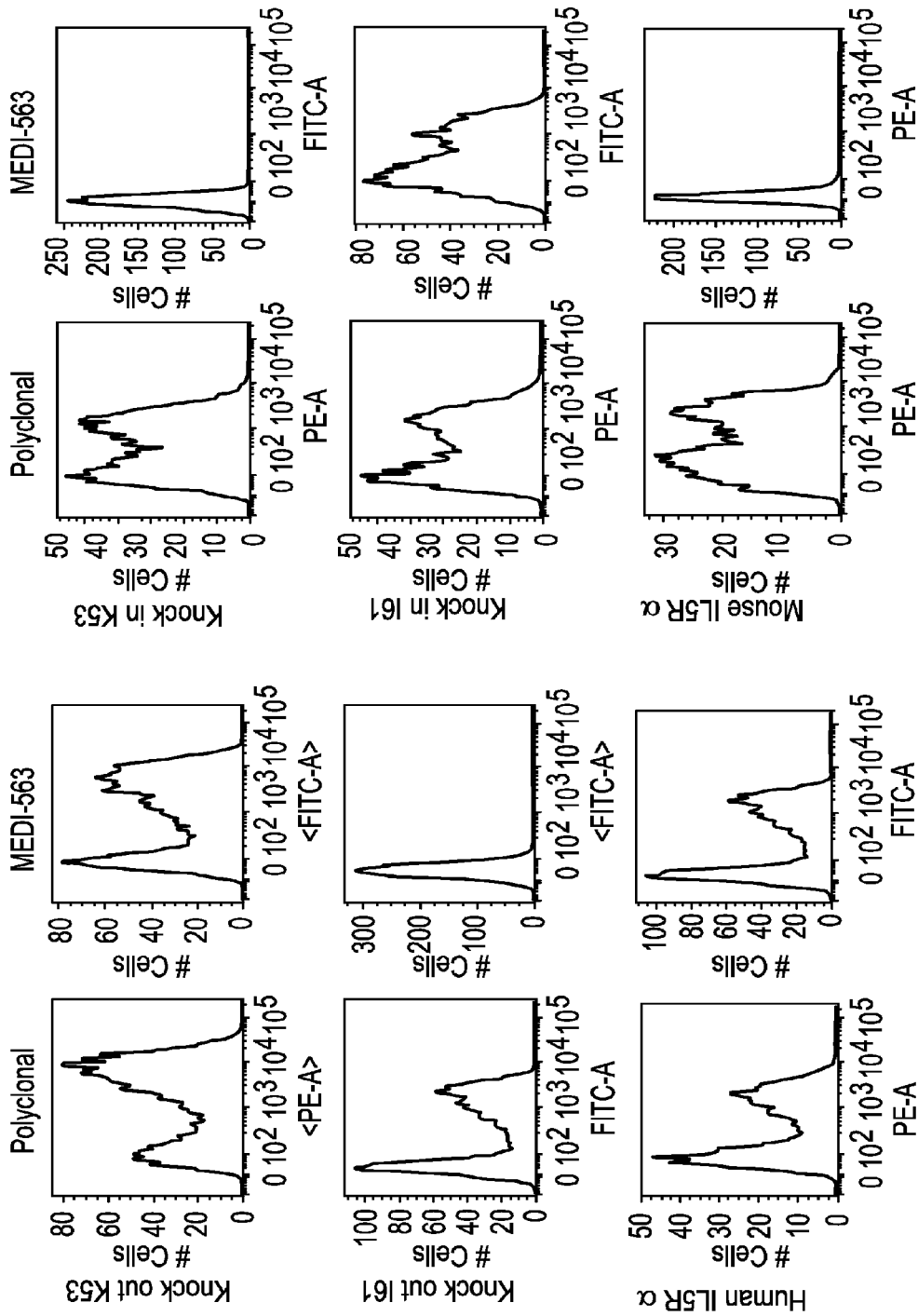

|  | muFcgRIV | muFcgRIII | muFcgRIIb | muFcgRI |
|---|---|---|---|---|
| Hu IgG$_1$ | 253 | 3660 | 1240 | 280 |
| Hu IgG$_1$ afuc | 43 | 3960 | 1260 | 397 |

Fig. 28

SEQUENCE LISTING

```
<160> NUMBER OF SEQ ID NOS: 6

<210> SEQ ID NO 1
<211> LENGTH: 107
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Gly Thr Ser Glu Asp Ile Ile Asn Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Tyr
                85                  90                  95

Thr Phe Gly Gln Gly Thr Lys Val Glu Ile Lys
            100                 105

<210> SEQ ID NO 2
<211> LENGTH: 214
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gly Thr Ser Glu Asp Ile Ile Asn Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 3
<211> LENGTH: 121
<212> TYPE: PRT
<213> ORGANISM: Homo sapiens

<400> SEQUENCE: 3

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile His Trp Val Arg Gln Arg Pro Gly Gln Gly Leu Ala Trp Met
        35                  40                  45

Gly Tyr Ile Asn Pro Tyr Asn Asp Gly Thr Lys Tyr Asn Glu Arg Phe
    50                  55                  60

Lys Gly Lys Val Thr Ile Thr Ser Asp Arg Ser Thr Ser Thr Val Tyr
65                  70                  75                  80

Met Glu Leu Ser Ser Leu Arg Ser Glu Asp Thr Ala Val Tyr Leu Cys
                85                  90                  95

Gly Arg Glu Gly Ile Arg Tyr Tyr Gly Leu Leu Gly Asp Tyr Trp Gly
            100                 105                 110

Gln Gly Thr Leu Val Thr Val Ser Ser
            115                 120

<210> SEQ ID NO 4
<211> LENGTH: 451
<212> TYPE: PRT
<213> ORGANISM: Homo sapiens

<400> SEQUENCE: 4

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile His Trp Val Arg Gln Arg Pro Gly Gln Gly Leu Ala Trp Met
        35                  40                  45

Gly Tyr Ile Asn Pro Tyr Asn Asp Gly Thr Lys Tyr Asn Glu Arg Phe
    50                  55                  60

Lys Gly Lys Val Thr Ile Thr Ser Asp Arg Ser Thr Ser Thr Val Tyr
65                  70                  75                  80

Met Glu Leu Ser Ser Leu Arg Ser Glu Asp Thr Ala Val Tyr Leu Cys
                85                  90                  95

Gly Arg Glu Gly Ile Arg Tyr Tyr Gly Leu Leu Gly Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 5
<211> LENGTH: 400
<212> TYPE: PRT
<213> ORGANISM: Homo sapiens

<400> SEQUENCE: 5

Asp Leu Leu Pro Asp Glu Lys Ile Ser Leu Leu Pro Pro Val Asn Phe
1               5                   10                  15

Thr Ile Lys Val Thr Gly Leu Ala Gln Val Leu Leu Gln Trp Lys Pro
                20                  25                  30

Asn Pro Asp Gln Glu Gln Arg Asn Val Asn Leu Glu Tyr Gln Val Lys
            35                  40                  45

Ile Asn Ala Pro Lys Glu Asp Asp Tyr Glu Thr Arg Ile Thr Glu Ser
```

Lys Cys Val Thr Ile Leu His Lys Gly Phe Ser Ala Ser Val Arg Thr
65                  70                  75                  80

Ile Leu Gln Asn Asp His Ser Leu Leu Ala Ser Ser Trp Ala Ser Ala
                85                  90                  95

Glu Leu His Ala Pro Pro Gly Ser Pro Gly Thr Ser Ile Val Asn Leu
            100                 105                 110

Thr Cys Thr Thr Asn Thr Thr Glu Asp Asn Tyr Ser Arg Leu Arg Ser
        115                 120                 125

Tyr Gln Val Ser Leu His Cys Thr Trp Leu Val Gly Thr Asp Ala Pro
    130                 135                 140

Glu Asp Thr Gln Tyr Phe Leu Tyr Tyr Arg Tyr Gly Ser Trp Thr Glu
145                 150                 155                 160

Glu Cys Gln Glu Tyr Ser Lys Asp Thr Leu Gly Arg Asn Ile Ala Cys
                165                 170                 175

Trp Phe Pro Arg Thr Phe Ile Leu Ser Lys Gly Arg Asp Trp Leu Ala
            180                 185                 190

Val Leu Val Asn Gly Ser Ser Lys His Ser Ala Ile Arg Pro Phe Asp
        195                 200                 205

Gln Leu Phe Ala Leu His Ala Ile Asp Gln Ile Asn Pro Pro Leu Asn
    210                 215                 220

Val Thr Ala Glu Ile Glu Gly Thr Arg Leu Ser Ile Gln Trp Glu Lys
225                 230                 235                 240

Pro Val Ser Ala Phe Pro Ile His Cys Phe Asp Tyr Glu Val Lys Ile
                245                 250                 255

His Asn Thr Arg Asn Gly Tyr Leu Gln Ile Glu Lys Leu Met Thr Asn
            260                 265                 270

Ala Phe Ile Ser Ile Ile Asp Asp Leu Ser Lys Tyr Asp Val Gln Val
        275                 280                 285

Arg Ala Ala Val Ser Ser Met Cys Arg Glu Ala Gly Leu Trp Ser Glu
    290                 295                 300

Trp Ser Gln Pro Ile Tyr Val Gly Asn Asp Glu His Lys Pro Leu Arg
305                 310                 315                 320

Glu Trp Phe Val Ile Val Ile Met Ala Thr Ile Cys Phe Ile Leu Leu
                325                 330                 335

Ile Leu Ser Leu Ile Cys Lys Ile Cys His Leu Trp Ile Lys Leu Phe
            340                 345                 350

Pro Pro Ile Pro Ala Pro Lys Ser Asn Ile Lys Asp Leu Phe Val Thr
        355                 360                 365

Thr Asn Tyr Glu Lys Ala Gly Ser Ser Glu Thr Glu Ile Glu Val Ile
    370                 375                 380

Cys Tyr Ile Glu Lys Pro Gly Val Glu Thr Leu Glu Asp Ser Val Phe
385                 390                 395                 400

<210> SEQ ID NO 6
<211> LENGTH: 398
<212> TYPE: PRT
<213> ORGANISM: Mus musculus

<400> SEQUENCE: 6

Asp Leu Leu Asn His Lys Lys Phe Leu Leu Pro Pro Val Asn Phe
1               5                   10                  15

Thr Ile Lys Ala Thr Gly Leu Ala Gln Val Leu Leu His Trp Asp Pro
            20                  25                  30

-continued

```
Asn Pro Asp Gln Glu Gln Arg His Val Asp Leu Glu Tyr His Val Lys
    35                  40                  45

Ile Asn Ala Pro Gln Asp Glu Tyr Asp Thr Arg Lys Thr Glu Ser
50                  55                  60

Lys Cys Val Thr Pro Leu His Glu Gly Phe Ala Ala Ser Val Arg Thr
65                  70                  75                  80

Ile Leu Lys Ser Ser His Thr Thr Leu Ala Ser Ser Trp Val Ser Ala
                85                  90                  95

Glu Leu Lys Ala Pro Pro Gly Ser Pro Gly Thr Ser Val Thr Asn Leu
                100                 105                 110

Thr Cys Thr Thr His Thr Val Val Ser Ser His Thr His Leu Arg Pro
            115                 120                 125

Tyr Gln Val Ser Leu Arg Cys Thr Trp Leu Val Gly Lys Asp Ala Pro
    130                 135                 140

Glu Asp Thr Gln Tyr Phe Leu Tyr Tyr Arg Phe Gly Val Leu Thr Glu
145                 150                 155                 160

Lys Cys Gln Glu Tyr Ser Arg Asp Ala Leu Asn Arg Asn Thr Ala Cys
                165                 170                 175

Trp Phe Pro Arg Thr Phe Ile Asn Ser Lys Gly Phe Glu Gln Leu Ala
                180                 185                 190

Val His Ile Asn Gly Ser Ser Lys Arg Ala Ala Ile Lys Pro Phe Asp
        195                 200                 205

Gln Leu Phe Ser Pro Leu Ala Ile Asp Gln Val Asn Pro Pro Arg Asn
    210                 215                 220

Val Thr Val Glu Ile Glu Ser Asn Ser Leu Tyr Ile Gln Trp Glu Lys
225                 230                 235                 240

Pro Leu Ser Ala Phe Pro Asp His Cys Phe Asn Tyr Glu Leu Lys Ile
                245                 250                 255

Tyr Asn Thr Lys Asn Gly His Ile Gln Lys Glu Lys Leu Ile Ala Asn
                260                 265                 270

Lys Phe Ile Ser Lys Ile Asp Asp Val Ser Thr Tyr Ser Ile Gln Val
            275                 280                 285

Arg Ala Ala Val Ser Ser Pro Cys Arg Met Pro Gly Arg Trp Gly Glu
    290                 295                 300

Trp Ser Gln Pro Ile Tyr Val Gly Lys Glu Arg Lys Ser Leu Val Glu
305                 310                 315                 320

Trp His Leu Ile Val Leu Pro Thr Ala Ala Cys Phe Val Leu Leu Ile
                325                 330                 335

Phe Ser Leu Ile Cys Arg Val Cys His Leu Trp Thr Arg Leu Phe Pro
                340                 345                 350

Pro Val Pro Ala Pro Lys Ser Asn Ile Lys Asp Leu Pro Val Val Thr
            355                 360                 365

Glu Tyr Glu Lys Pro Ser Asn Glu Thr Lys Ile Glu Val Val His Cys
    370                 375                 380

Val Glu Glu Val Gly Phe Glu Val Met Gly Asn Ser Thr Phe
385                 390                 395
```

METHODS OF REDUCING BASOPHIL LEVELS

CROSS REFERENCE TO RELATED APPLICATIONS

This application is a continuation of U.S. patent application Ser. No. 13/177,221, filed Jul. 6, 2011, said U.S. application Ser. No. 13/177,221 is a continuation of U.S. patent application Ser. No. 12/600,017, filed Jul. 26, 2010, now abandoned, said U.S. application Ser. No. 12/600,017 claims the benefit under 35 U.S.C. §365(a) of International Patent Application No. PCT/US2008/006156, filed May 14, 2008, now published, which claims the benefit under 35 U.S.C. §365(c) of U.S. Provisional Application Nos. 60/924,422, filed May 14, 2007, 60/924,832, filed Jun. 1, 2007, 60/935,005, filed Jul. 20, 2007 and 61/064,612, filed Mar. 14, 2008. Each of the above listed applications is incorporated by reference herein in its entirety for all purposes.

REFERENCE TO THE SEQUENCE LISTING

This application incorporates by reference a Sequence Listing submitted with this application as text file entitled IL5R500US3_sequence_listing created on May 24, 2013 and having a size of 15 kilobytes.

FIELD OF THE INVENTION

The present invention relates to methods of reducing eosinophil levels in human subjects.

BACKGROUND OF THE INVENTION

Eosinophils are implicated in various diseases including allergic diseases, and are thought to play an important role in generating morbidity of allergic diseases, such as chronic bronchial asthma and atopic dermatitis [Adv. Immunol., 39, 177 (1986), Immunol. Today, 13, 501 (1992)]. In addition to the above diseases, eosinophils are also implicated in diseases generally referred to as hypereosinophilic syndrome (HES), such as eosinophilia, eosinophilic enterogastritis, eosinophilic leukemia, eosinophilic granuloma and Kimura's disease [Ann. Intern. Med., 97, 78 (1982)].

Eosinophilic granuloma is nonneoplastic cryptogenic lesion, which is an osteolytic and focal, and is known to be associated with remarkable tissue eosinophilia [U.S. Armed Forces Med. J., 2, 1085 (1951)]. According to the registry of bone tumor patients in Japan (1972-1984), 379 out of 404 bone tumor patients (93.8%) suffered from eosinophilic granuloma. Eosinophilic granuloma at the early stage mainly comprises eosinophils and histiocytes, and the granuloma at the advanced stage comprises fibrosis, or may progress to fibroid lung. Hence, in addition to inflammatory diseases, such as allergy, eosinophils can cause other various diseases.

Interleukin-5 (hereinafter referred to as IL-5), interleukin-3 (hereinafter referred to as IL-3) and granulocyte-macrophage colony-stimulating factor (hereinafter referred to as GM-CSF), which are members of cytokine family, are involved in regulating the differentiation, proliferation and activation of eosinophils. Of these cytokines, IL-5 is known to act specifically on eosinophils and specifically induce the terminal differentiation [Proc. Natl. Acad. Sci. U.S.A., 85, 2288 (1988)].

In vitro, IL-3 and/or GM-CSF can activate eosinophils or prolong their survival [J. Clin. Invest., 81, 1986 (1988)]. Further, IL-3 and/or GM-CSF acts also predominantly on the induction of immature eosinophils from myeloid stem cells [Blood, 76, 1956 (1990)]. Furthermore, chemokines such as eotaxin and RANTES (regulated on activation normal T-cell expressed and secreted), induce the chemotaxis of eosinophils to inflamed site [Clin. Exp. Allergy, 26, 1005 (1996)]. Stem cell factors hereinafter referred to as SCF) are involved in the accumulation of eosinophils in allergic bronchitis. In addition to IL-5, there are many factors affecting function of eosinophils.

Eosinophils are divided into subgroups, normodense eosinophils and hypodense eosinophils. Eosinophils have been shown to be hypodense eosinophils upon activation [Immunology, 47, 531 (1982)]. Hypodense eosinophils are also referred to as activated eosinophils. It has been reported that a qualitative change occurs in addition to a quantitative change in eosinophils in the peripheral blood of an HES patients [Clin. Exp. Immunol., 24, 423 (1976)]. Activated eosinophils have been implicated in the severity of HES symptom [Am. J. Cardiol., 52, 321 (1983)]. Aside from HES patients, activated eosinophils have been also found in the peripheral blood, and in bronchoalveolar lavage fluid (BALE) of a patient with bronchial asthma [Am. Rev. Respir. Dis, 132, 981 (1985)]. Various receptors, such as those of cytokines, are expressed on activated eosinophils (hypodense eosinophils) [J. Immunol., 142, 4416 (1989)]. Compared to normodense eosinophils, these hypodense eosinophils show elevated sensitivities against IL-5 [Clin. Exp. Immunol., 85, 312 (1991); J. Exp. Med., 172, 1347 (1990)].

The above-mentioned activated eosinophils are also known to survive in vitro without the cytokines inducing in the differentiation and proliferation of eosinophils [J. Exp. Med., 170, 343 (1989)]. Thus, the properties of activated eosinophils are similar to those of eosinophils, which infiltrate tissues, such as alveoli [Int. Arch. Allergy Immunol., 120, 91 (1999)]. A detailed explanation of why activated eosinophils become cytokine-independent remains unknown, however, their degranulation and prolonged survival are likely to be induced by various vital functional molecules other than IL-5.

Substances having inhibition activity on cytokines or chemokines that are involved in the differentiation or proliferation of eosinophils have been considered as agents that inhibit the eosinophil functions. However, in most cases these agents do not act on cytokine-independent eosinophils that have been activated and infiltrated into inflamed areas. Hence, eosinophil-specific inhibition and the induction of cellular death of activated eosinophils are necessary to inhibit the functions of any eosinophil. However, no anti-inflammatory agent, so far, has been known to induce apoptosis of activated eosinophils.

Currently, treatment for patients with eosinophilic diseases consists of administration of steroids. However, steroid administration is often associated with side effects. Specifically, the treatment has some other problems, such that patient's pathological condition may return to the original state when steroid administration is discontinued, and prolonged steroid administration may induce steroid resistance. Accordingly, there is a need for safe and effective treatments for eosinophil mediated diseases and disorders.

SUMMARY OF THE INVENTION

The invention provides a method of reducing the numbers of eosinophils in a human subject comprising administration to said patient an IL-5R binding molecule that comprises (a) a region that specifically binds to the IL-5R and (b) an immunoglobulin Fc region.

BRIEF DESCRIPTION OF THE FIGURES

For the purpose of illustrating the invention, there are depicted in the drawings certain embodiments on the invention. However, the invention is not limited to the precise arrangements and instrumentalities of the embodiments depicted in the drawings.

FIG. 10. MEDI-563 binding to rhuIL-5Rα: binding affinity of MEDI-563 to recombinant human IL-5Rα was measured by surface plasmon resonance in three separate experiments and is summarized in this figure.

FIG. 11. MEDI-563 binding to rhuFcγRs: binding affinity of MEDI-563 to recombinant human FcγRs of several different lots was measured as compared to a isotype-matched fucosylated control antibody and is summarized in this figure. Note that MEDI-563 binds with 5-10 fold higher affinity to huFcγRIIIa and muFcγRIV.

FIG. 16. FACS Analysis of Leukocytes from IL-5 Transgenic Mice: flow cytometry analysis was performed on leukocytes from IL-5 transgenic mice as described in Example 7.

FIG. 28. Chimeric anti-mouse IL-5Rα (H7) binding to murine FcγRs: binding affinity of chimeric anti-mouse IL-5Rα (H7) to recombinant murine FcγRs was measured as compared to an isotype-matched fucosylated control antibody and is summarized in this figure. Dissociation constants are shown (nM). Measurements were done by surface plasmon resonance.

DETAILED DESCRIPTION OF THE INVENTION

Figure 1:
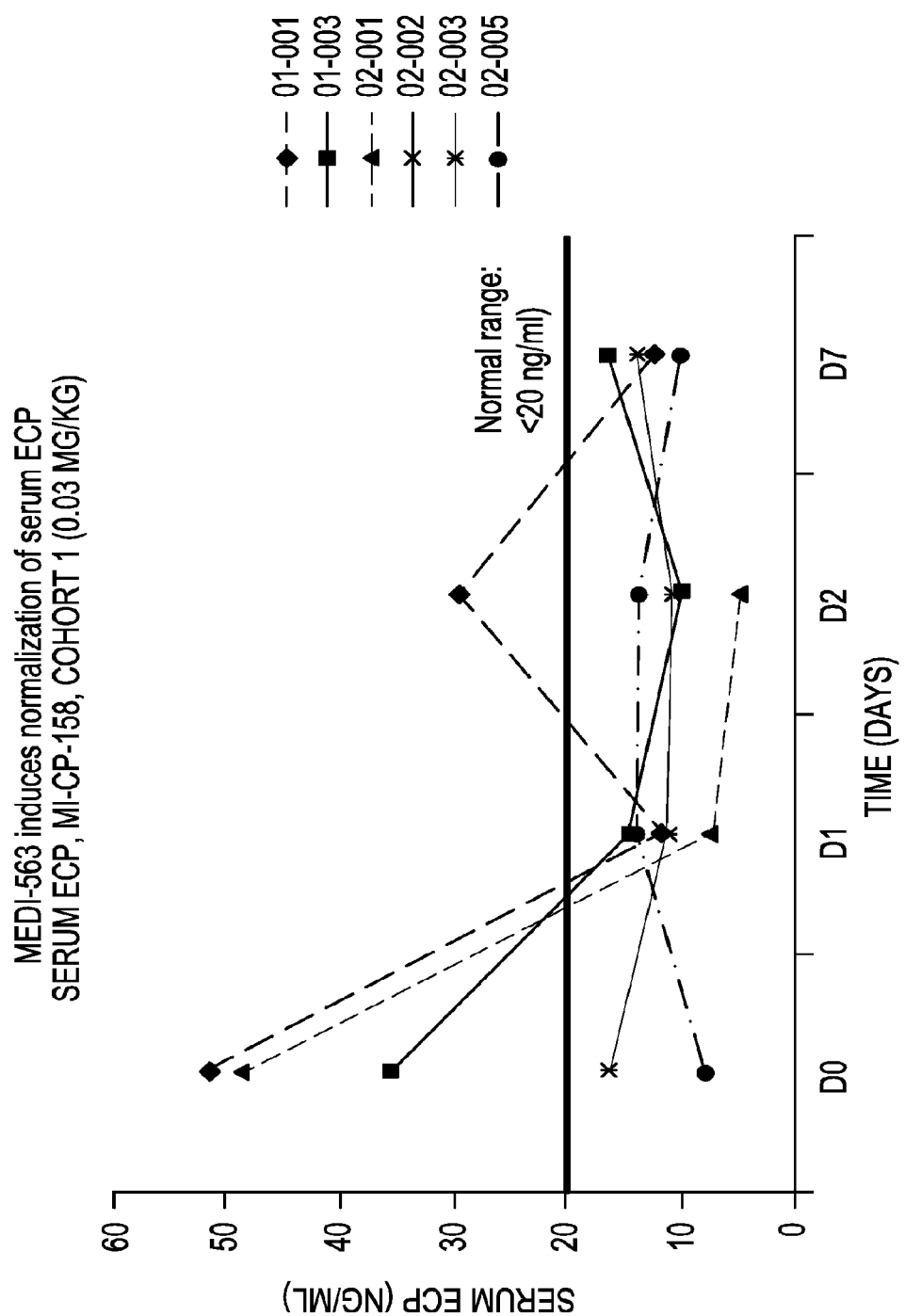
FIG. 1. Decrease in serum eosinophil cationic protein (ECP): ECP is a marker produced by eosinophils. In patient cohort 1, this decrease in ECP levels tracks the decrease in eosinophils observed in FIG. 1. The y-axis summarizes ECP levels (ng/ml) and x-axis summarizes time (in days).
Figure 2:
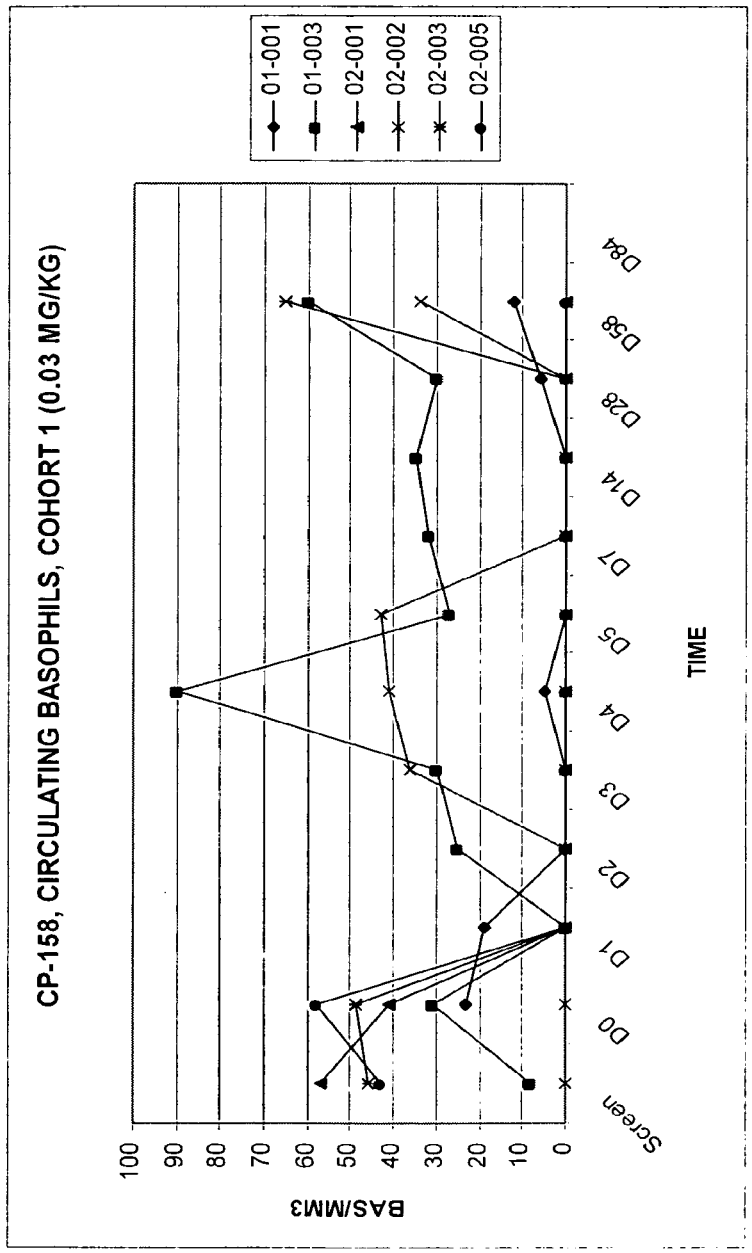
FIG. 2. Reversible peripheral basophil depletion: circulating basophils were measured in patient cohort 1. The y-axis summarizes basophil counts (basophils/mm3) and x-axis summarizes time (in days). Rapid reduction of basophils in the periphery was observed by 24 hours post-administration.
Figure 3:
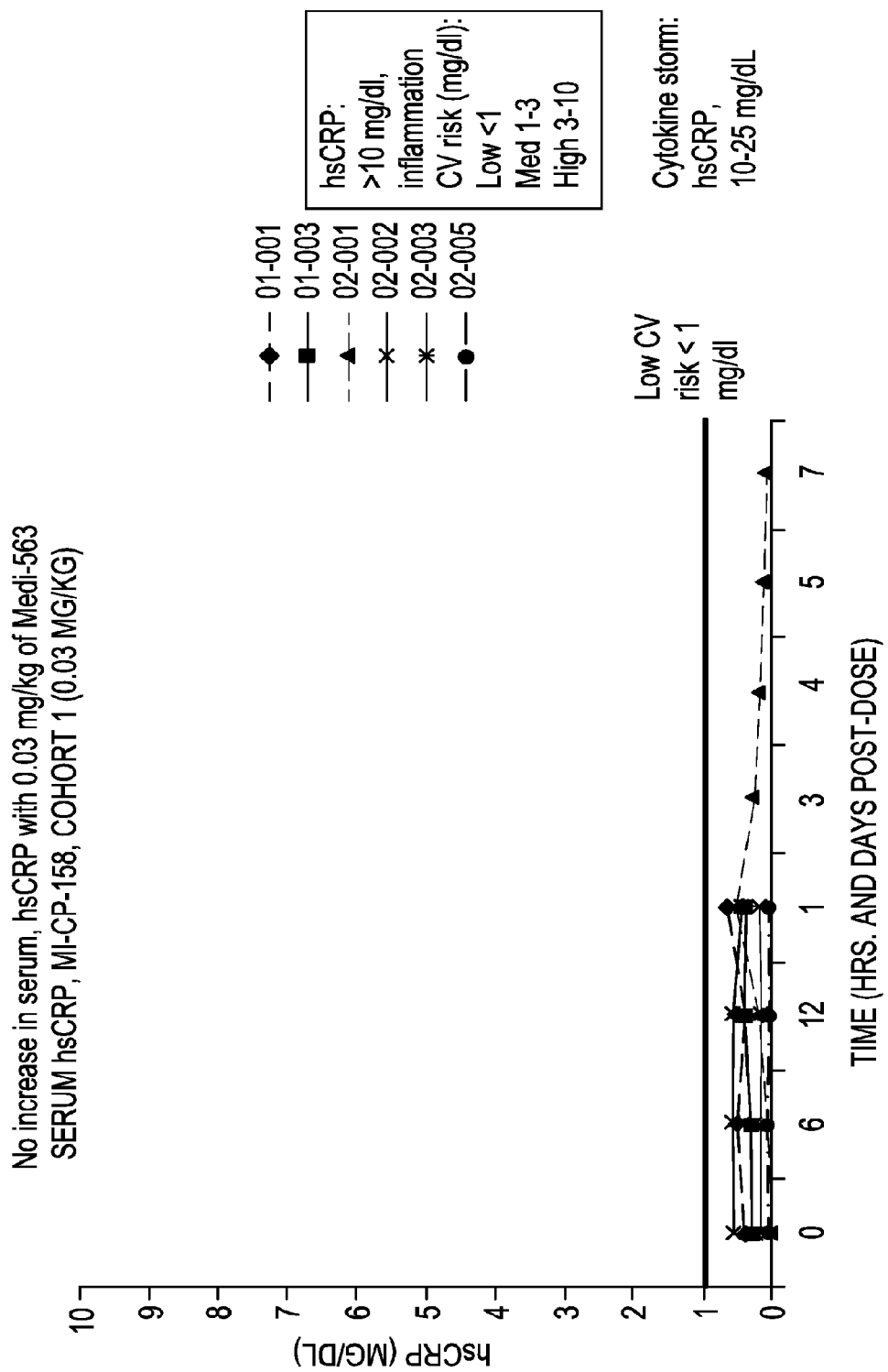
FIG. 3. Increased (reversible) hsCRP (high sensitivity c-reactive protein) in subjects with eosinophilia at baseline. Measurement of this marker in patient cohort 1 demonstrates that the expected immune mediated response against cells expressing the IL-5R is occurring. The y-axis summarizes hsCRP levels (mg/dl) and x-axis summarizes time (in days).
Figure 4:
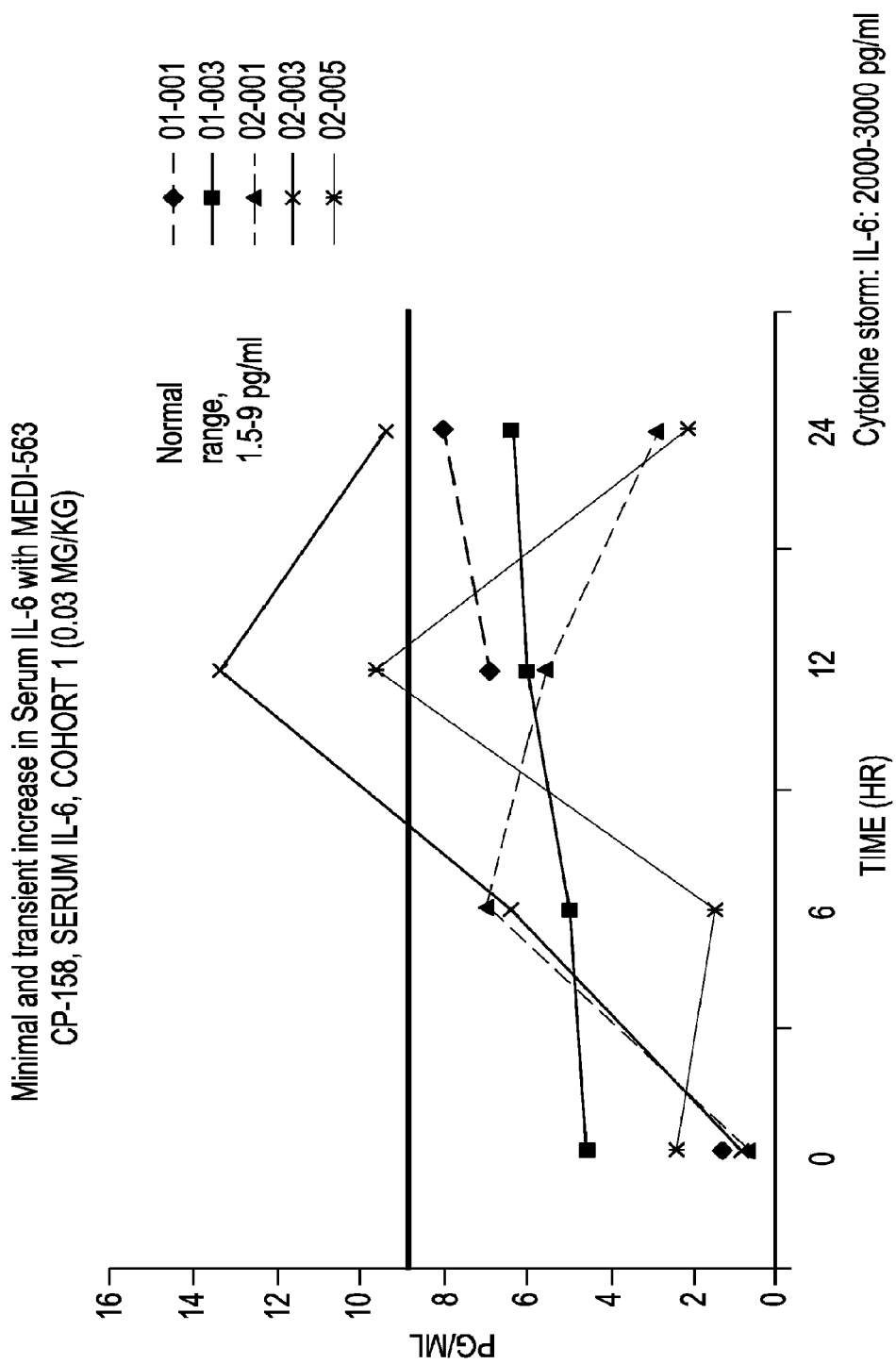
FIG. 4. Minimal increase in serum IL-6. Measurement of the IL-6 cytokine in patient cohort 1 is summarized. The y-axis summarizes IL-6 levels (pg/ml) and x-axis summarizes time (in hours).
Figure 5:
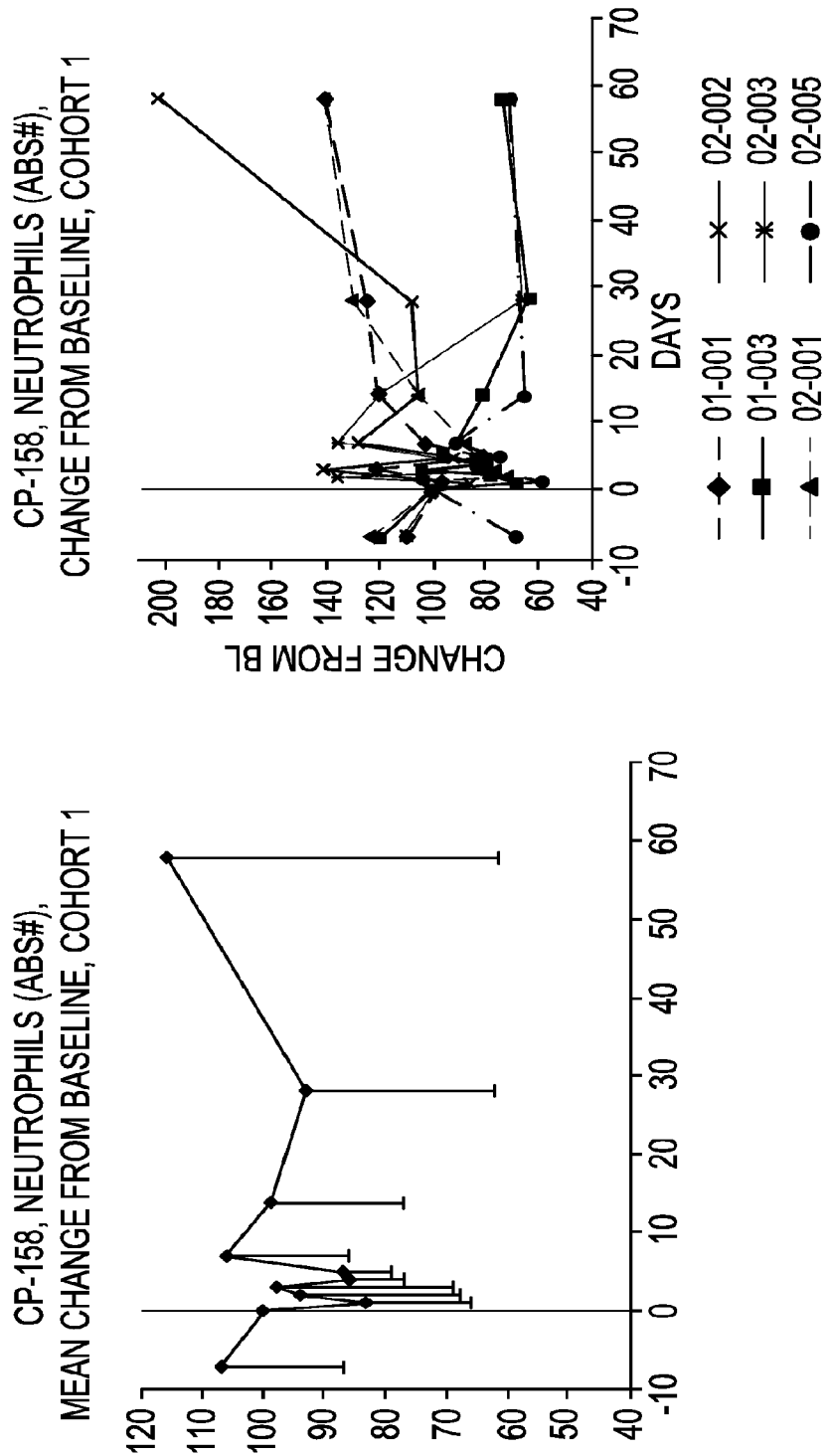
FIG. 5. Variable decrease of circulating neutrophils. Neutrophil levels in patient cohort 1 were measured and are summarized in both panels.
Figure 6:
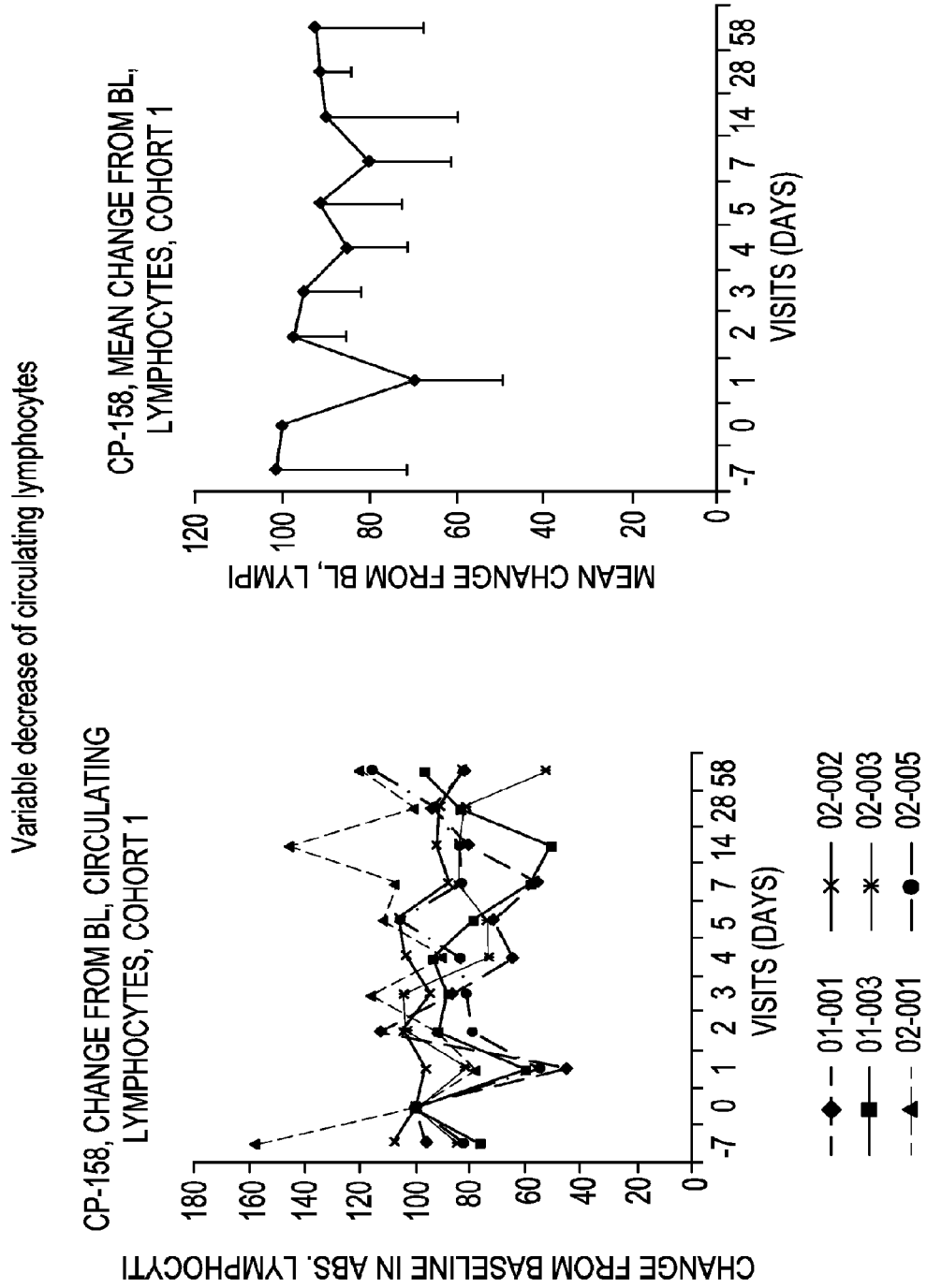
FIG. 6. Variable decrease of circulating lymphocytes. Lymphocyte levels in patient cohort 1 were measured and are summarized in both panels.
Figure 7:
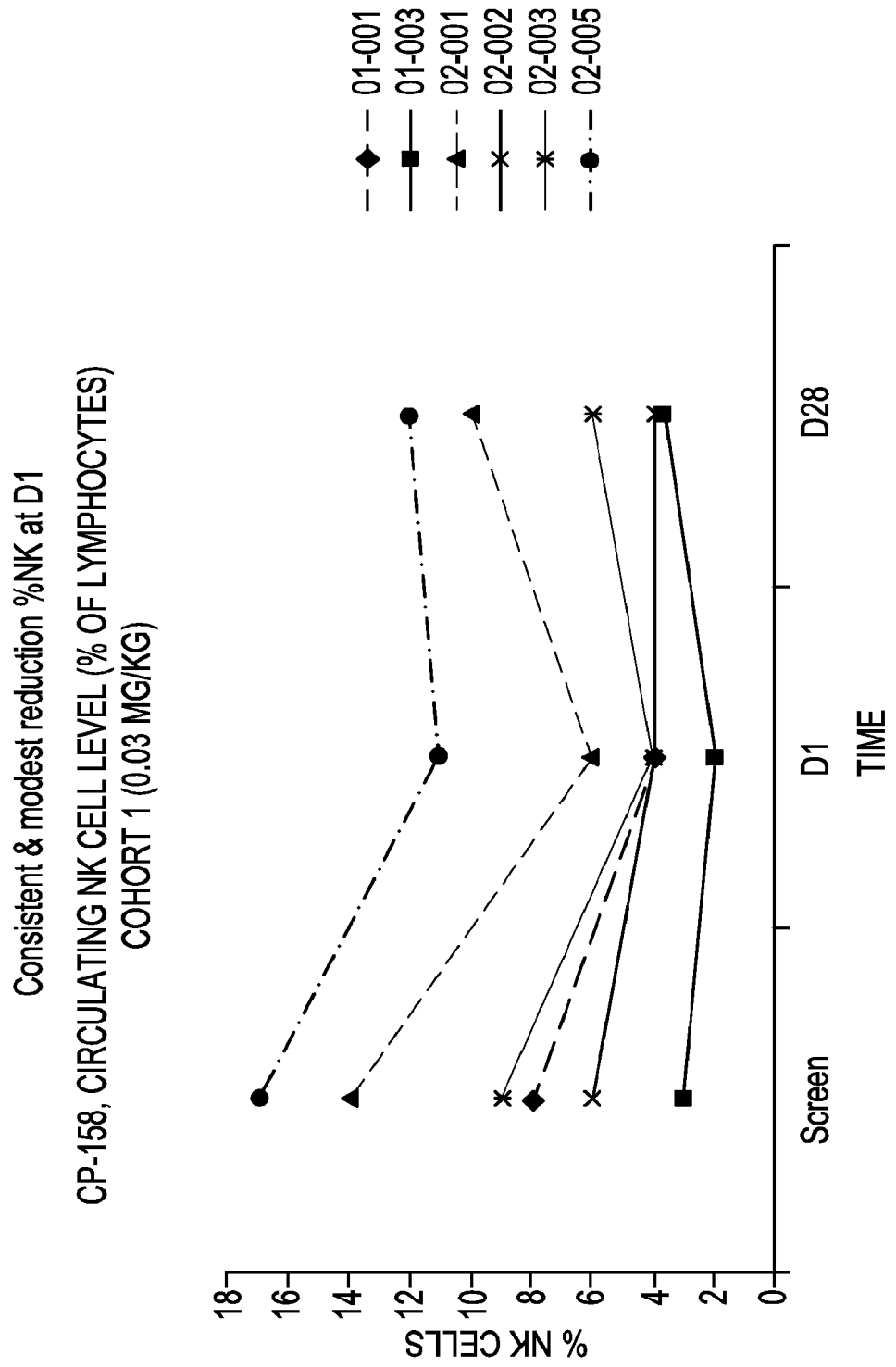
FIG. 7. Consistent and modest reduction of % NK at Day 1. NK cell levels in patient cohort 1 were measured prior to treatment, at day 1 post-administration, and at day 28 post-administration.
Figure 8:
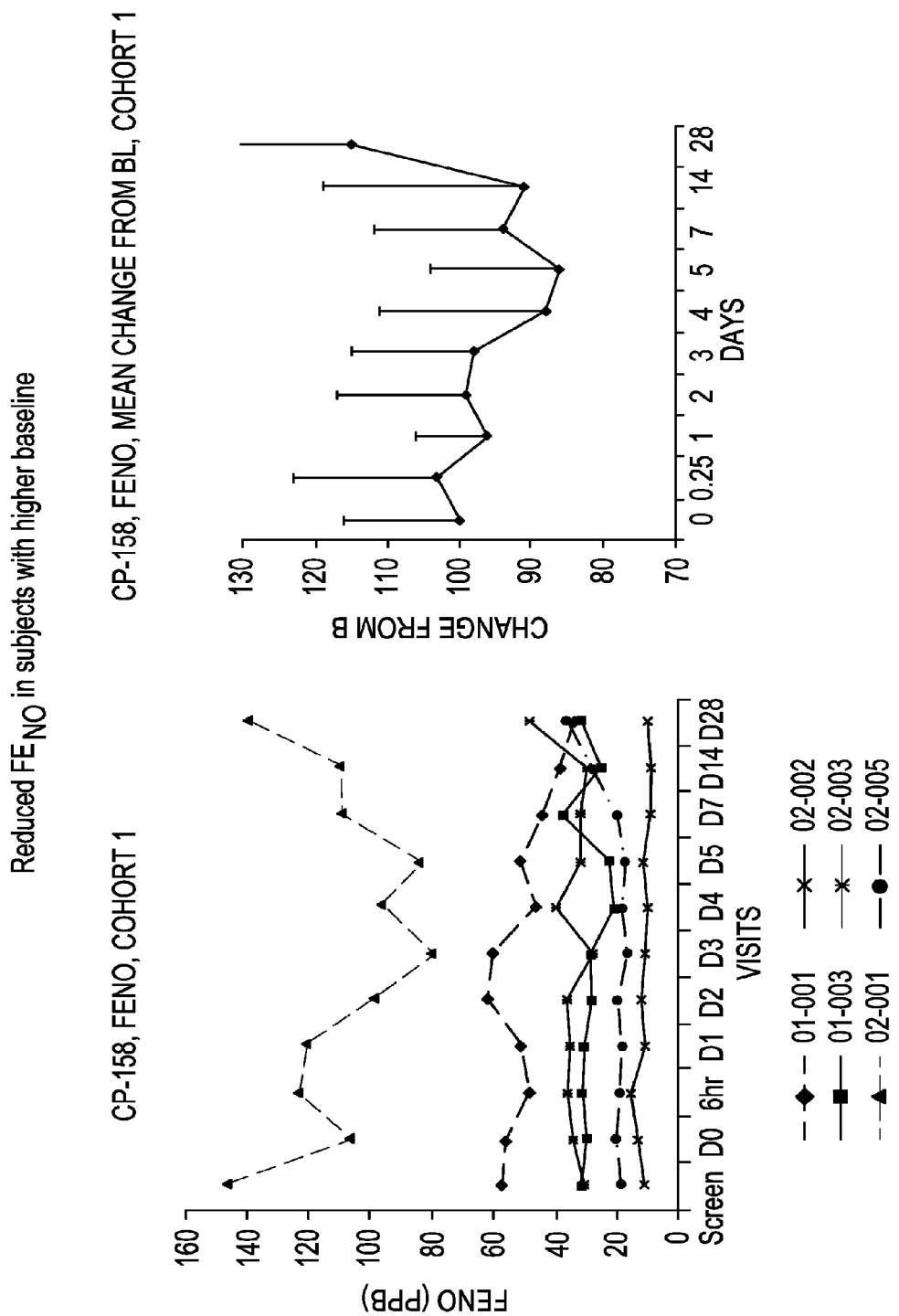
FIG. 8. Reduced $FE_{NO}$ in subjects with higher baseline. The fraction of exhaled nitric oxide was measured in patient cohort 1. This assay is a noninvasive measurement of lung inflammation, with the data indicating a trend towards reduction in inflammation.

As discussed herein above and not being bound by a particular hypothesis or theory, eosinophils have been implicated in the pathogenesis of numerous diseases and disorders. Many of these diseases or disorders are characterized by an overabundance of eosinophils (eosinophilia), and are termed hypereosinophilic syndromes.

Nonlimiting examples of diseases and disorders in which eosinophils play a role are: asthma, immunoglobulin (IgE)-mediated food allergy, eosinophilic esophagitis (inflammation of the esophagus), inflammatory bowel disease, COPD, allergic colitis, astro-esophageal reflux, eosinophilic gastrointestinal disease (EGID), eosinophilic gastroenteritis, endomyocardial fibrosis, Loeffler's endocarditis, Davies disease, Episodic Angioedema Associated With Eosinophilia, Eosinophilia-Myalgia Syndrome/Spanish Toxic Oil Syndrome, liver cirrhosis, dermatitis herpetiformis, Bullous pemphigoid, Churg-Strauss syndrome, Acute myelogenous eosinophilic leukemia, Acute lymphocytic eosinophilic leukemia, Systemic mastocytosis with eosinophilia, Allergic rhinitis, Eczema, Wegener's granulomatosis, Polyarteritis nodosa, Eosinophilic fasiculitis, and Rheumatoid arthritis.

Accordingly, the invention provides a method of reducing the numbers of eosinophils in a human subject comprising administration to said patient an IL-5R binding molecule that comprises (a) a region that specifically binds to the IL-5R and (b) an immunoglobulin Fc region.

In one embodiment, the invention provides methods of reducing the number of eosinophils in a human subject comprising administration to said patient an IL-5R binding molecule that comprises (a) a region that specifically binds to the IL-5R and (b) an immunoglobulin Fc region. In a specific embodiment, a method of the invention reduces the number of eosinophils in blood, bone marrow, gastrointestinal tract (e.g., esophagus, stomach, small intestine and colon), or lung. In another specific embodiment, a method of the invention reduces the number of blood eosinophils. In a further specific embodiment, a method of the invention reduces the number of lung eosinophils. In a specific embodiment, a method of the invention reduces the number of eosinophil precursor cells.

In another embodiment, a method of the invention reduces the number of eosinophils by at least about 10%, at least about 20%, at least about 30%, at least about 40%, at least about 50%, at least about 60%, at least about 70%, at least about 80%, at least about 90%, at least about 95% or at least about 99%. In a specific embodiment, a method of the invention reduces the number of eosinophils below the limit of detection.

In another embodiment, a method of the invention reduces the number of eosinophil precursors by at least about 10%, at least about 20%, at least about 30%, at least about 40%, at least about 50%, at least about 60%, at least about 70%, at least about 80%, at least about 90%, at least about 95% or at least about 99%. In a specific embodiment, a method of the invention reduces the number of eosinophil precursors below the limit of detection.

In a further embodiment, a method of the invention eliminates all detectable eosinophils following a single administration of an IL-5R binding molecule. In a specific embodiment, a single administration of an IL-5R binding molecule eliminates all detectable eosinophils for at least about 1 day, at least about 2 days, at least about 3 days, at least about 4 days, at least about 5 days, at least about 6 days, at least about 7 days, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 12 weeks, at least about 14 weeks, at least about 16 weeks, at least about 20 weeks, or at least about 25 weeks.

In a further embodiment, a method of the invention eliminates all detectable eosinophil precursors following a single administration of an IL-5R binding molecule. In a specific embodiment, a single administration of an IL-5R binding molecule eliminates all detectable eosinophil precursors for at least about 1 day, at least about 2 days, at least about 3 days, at least about 4 days, at least about 5 days, at least about 6 days, at least about 7 days, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 12 weeks, at least about 14 weeks, at least about 16 weeks, at least about 20 weeks, or at least about 25 weeks.

In a specific embodiment, method of the invention comprises the administration to a subject a single dose of 0.03 mg/kg of an IL-5R binding molecule that comprises (a) a region that specifically binds to the IL-5R and (b) an immunoglobulin Fc region, wherein the administration of the IL-5R binding molecule leads to depletion of at least about 99% of eosinophils from the subject's circulation, wherein the depletion is complete by 24 hrs after dosing, and wherein the depletion lasts for at least about 28 days after dosing.

In a specific embodiment, method of the invention comprises the administration to a subject a single dose of 0.1 mg/kg of an IL-5R binding molecule that comprises (a) a region that specifically binds to the IL-5R and (b) an immunoglobulin Fc region, wherein the administration of the IL-5R binding molecule leads to depletion of at least about 99% of eosinophils from the subject's circulation, wherein the depletion is complete by 24 hrs after dosing, and wherein the depletion lasts for at least about 84 days after dosing.

In one embodiment, the IL-5R binding molecules of the present invention include fusion proteins. In certain embodiments, the fusion proteins comprise a polypeptide region that specifically binds to the IL-5R, and further comprise an immunoglobulin Fc region. Nonlimiting examples of a polypeptide region that specifically bind to the IL-5R can be found in U.S. Pat. Nos. 7,109,299 and 5,677,280, U.S. Patent Application Publication No. 2006/0014680 A1. In other embodiments, the polypeptide region that specifically binds to the IL-5R is human IL-5 (see, for example, Tanabi et al., Journal of Biological Chemistry, 1987, Vol. 262, No. 34, pp. 16580-16584), or fragments, derivatives or variants thereof (see, for example, U.S. Pat. No. 6,465,616).

In one embodiment, the IL-5R binding molecules of the present invention comprise antibodies. Antibodies of the present invention include, but are not limited to, monoclonal antibodies, synthetic antibodies, multispecific antibodies (including bi-specific antibodies), human antibodies, humanized antibodies, chimeric antibodies, single-chain Fvs (scFv) (including bi-specific scFvs), single chain antibodies, Fab fragments, F(ab') fragments, disulfide-linked Fvs (sdFv), and epitope-binding fragments of any of the above. In particular, antibodies of the present invention include immunoglobulin molecules and immunologically active portions of immunoglobulin molecules, i.e., molecules that contain an antigen binding site that specifically bind to an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

The antibodies useful in the present invention may be from any animal origin including birds and mammals (for example, but not limited to, human, murine, donkey, sheep, rabbit, goat, guinea pig, camel, horse, or chicken). In specific embodiments, the antibodies are human or humanized monoclonal antibodies.

The antibodies useful in the present invention may be monospecific, bispecific, trispecific or of greater multispecificity. Multispecific antibodies may specifically bind to different epitopes of a polypeptide or may specifically bind to both a polypeptide as well a heterologous epitope, such as a heterologous polypeptide or solid support material. See, e.g., International Publication Nos. WO 93/17715, WO 92/08802, WO 91/00360, and WO 92/05793; Tutt, et al., 1991, J. Immunol. 147:60-69; U.S. Pat. Nos. 4,474,893, 4,714,681, 4,925,648, 5,573,920, and 5,601,819; and Kostelny et al., 1992, J. Immunol. 148:1547-1553.

The antibodies useful in the present invention can be single-chain antibodies. The design and construction of a single-chain antibody is described in Marasco et al, 1993, Proc Natl Acad Sci 90:7889-7893.

Nonlimiting examples of antibodies of the invention can be found in U.S. Pat. Nos. 7,179,464, 6,538,111, 6,018,032, and U.S. Patent Application Publication Nos. 2004/0136996A1, 2005/0226867A1.

In one embodiment, the IL-5R binding molecules of the present invention comprise antibodies. In a further embodiment, an IL-5R binding molecule of the present invention is an antibody comprising any one of the amino acid sequence of SEQ ID NO: 1-4. In a specific embodiment, an IL-5R binding molecule of the present invention is an antibody comprising the amino acid sequence of SEQ ID NO: 1 and 3. In a specific embodiment, an IL-5R binding molecule of the present invention is an antibody comprising the amino acid sequence of SEQ ID NO: 2 and 4.

In one embodiment, an IL-5R binding molecule of the present invention is an antibody that specifically binds to the same epitope as MEDI-563. In a specific embodiment, the antibody is MEDI-563. In a further specific embodiment, an IL-5R binding molecule of the present invention is an antibody that specifically binds to the same epitope as MEDI-563 provided that the antibody is not MEDI-563.

In one embodiment, an IL-5R binding molecule of the present invention is an antibody that specifically binds to an epitope comprising residues 1-102 of SEQ ID NO:5. In a specific embodiment, the antibody is MEDI-563. In a further specific embodiment, an IL-5R binding molecule of the present invention is an antibody that specifically binds to an epitope comprising residues 1-102 of SEQ ID NO:5 provided that the antibody is not MEDI-563.

In one embodiment, an IL-5R binding molecule of the present invention is an antibody that specifically binds to an epitope comprising residues 40-67 of SEQ ID NO:5. In a specific embodiment, the antibody is MEDI-563. In a further specific embodiment, an IL-5R binding molecule of the present invention is an antibody that specifically binds to an epitope comprising residues 40-67 of SEQ ID NO:5 provided that the antibody is not MEDI-563.

In one embodiment, an IL-5R binding molecule of the present invention is an antibody that specifically binds to an epitope comprising residues 52-67 of SEQ ID NO:5. In a specific embodiment, the antibody is MEDI-563. In a further specific embodiment, an IL-5R binding molecule of the present invention is an antibody that specifically binds to an epitope comprising residues 52-67 of SEQ ID NO:5 provided that the antibody is not MEDI-563.

In one embodiment, an IL-5R binding molecule of the present invention is an antibody that specifically binds to an epitope comprising residue 61 of SEQ ID NO:5. In a specific embodiment, the antibody is MEDI-563. In a further specific embodiment, an IL-5R binding molecule of the present invention is an antibody that specifically binds to an epitope comprising residue 61 of SEQ ID NO:5 provided that the antibody is not MEDI-563.

In one embodiment, an IL-5R binding molecule of the present invention is an antibody that specifically binds to a first antigen comprising residues 1-102 of SEQ ID NO:5 but does not specifically bind to a second antigen comprising a variant of residues 1-102 of SEQ ID NO:5 wherein the variant comprises the I61K substitution. In a specific embodiment, the antibody is MEDI-563. In a further specific embodiment, an IL-5R binding molecule of the present invention is an antibody that specifically binds to a first antigen comprising residues 1-102 of SEQ ID NO:5 but does not specifically bind to a second antigen comprising a variant of residues 1-102 of SEQ ID NO:5 wherein the variant comprises the I61K substitution, provided that the antibody is not MEDI-563.

In one embodiment, an IL-5R binding molecule of the present invention is an antibody that specifically binds to a first antigen comprising residues 40-67 of SEQ ID NO:5 but does not specifically bind to a second antigen comprising a variant of residues 40-67 of SEQ ID NO:5 wherein the variant comprises the I61K substitution. In a specific embodiment, the antibody is MEDI-563. In a further specific embodiment, an IL-5R binding molecule of the present invention is an antibody that specifically binds to a first antigen comprising residues 40-67 of SEQ ID NO:5 but does not specifically bind to a second antigen comprising a variant of residues 40-67 of SEQ ID NO:5 wherein the variant comprises the I61K substitution, provided that the antibody is not MEDI-563.

In one embodiment, an IL-5R binding molecule of the present invention is an antibody that specifically binds to human IL-5Ralpha (SEQ ID NO:5) but does not specifically bind to mutant human IL-5Ralpha (SEQ ID NO:5) comprising the I61K substitution. In a specific embodiment, the antibody is MEDI-563. In a further specific embodiment, an IL-5R binding molecule of the present invention is an antibody that specifically binds to human IL-5Ralpha (SEQ ID NO:5) but does not specifically bind to mutant human IL-5Ralpha (SEQ ID NO:5) comprising the I61K substitution, provided that the antibody is not MEDI-563.

The present invention provides IL-5R binding molecules with increased effector function. Nonlimiting examples of methods for increasing effector function can be found in U.S. Pat. Nos. 5,624,821, 6,602,684, 7,029,872, U.S. Patent Application Publication Nos. 2006/0067930A1, 2005/0272128A1, 2005/0079605A1, 2005/0123546A1, 2004/0072290A1, 2006/0257399A1, 2004/0261148A1, 2007/0092521, 2006/0040325A1, and 2006/0039904A1, and International Patent Application Publication Nos. WO 04/029207, WO03011878, WO05044859, WO 06071856, and WO 06071280.

Methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for FcγRIIB as compared with the binding affinity for FCγRIIA; see, also, PCT Publication Nos. WO 99/58572 to Armour et al., WO 99/51642 to Idusogie et al., and U.S. Pat. No. 6,395,272 to Deo et al.; the disclosures of which are incorporated herein in their entireties). Methods of modifying the Fc region to decrease binding affinity to FcγRIIB are also known in the art (e.g., U.S. Patent Publication No. 20010036459 and PCT Publication No. WO 01/79299, both to Ravetch et al., the disclosures of which are incorporated herein in their entireties). Modified antibodies having variant Fc regions with enhanced binding affinity for FcγRIIIA and/or FcγRIIA as compared with a wildtype Fc region have also been described (e.g., PCT Publication Nos. WO 2004/063351, to Stavenhagen et al., the disclosure of which is incorporated herein in its entirety).

Antibody effector function may also be modified through the generation of antibodies with altered glycosylation patterns. For example, an antibody can be made that has an altered type of glycosylation, such as an afucosylated/hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnIII)) such that antibodies expressed in the engineered cell lines exhibit increased bisecting GlcNac structures which results in increased ADCC activity of the antibodies (see also Umana et al. (1999) Nat. Biotech. 17:176-180).

Methods for generating antibodies with altered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003; J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49. Antibodies with altered fucosylation pattern may also be prepared by post-translational removal of fucose (e.g. with a fucosidase enzyme), The present invention provides for antibodies and antibody fragments that specifically bind to IL-5R which have an extended half-life in vivo. In particular, the present invention provides antibodies and antibody fragments which have a half-life in a mammal (for example, but not limited to, a human), of greater than 3 days, greater than 7 days, greater than 10 days, greater than 15 days, greater than 25 days, greater than 30 days, greater than 35 days, greater than 40 days, greater than 45 days, greater than 2 months, greater than 3 months, greater than 4 months, or greater than 5 months.

To prolong the serum circulation of antibodies (for example, but not limited to, monoclonal antibodies and single chain antibodies) or antibody fragments (for example, but not limited to, Fab fragments) in vivo, for example, inert polymer molecules such as high molecular weight polyethyleneglycol (PEG) can be attached to the antibodies (including antibody fragments thereof) with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies (including antibody fragments thereof) can be tested for binding activity as well as for in vivo efficacy using methods known to those of skill in the art, for example, by immunoassays described herein.

Antibodies having an increased half-life in vivo can also be generated introducing one or more amino acid modifications (i.e., substitutions, insertions or deletions) into an IgG constant domain, or FcRn binding fragment thereof (e.g., Fc or hinge Fc domain fragment). See, e.g., International Publication No. WO 98/23289; International Publication No. WO 97/34631; and U.S. Pat. No. 6,277,375, each of which is incorporated herein by reference in its entirety.

Further, antibodies (including antibody fragments thereof) can be conjugated to albumin in order to make the antibody (including antibody fragment thereof) more stable in vivo or have a longer half life in vivo. The techniques are well known in the art, see e.g., International Publication Nos. WO 93/15199, WO 93/15200, and WO 01/77137; and European Patent No. EP 413, 622, all of which are incorporated herein by reference.

The present invention provides IL-5R binding molecules that specifically bind to IL-5R, where the binding molecules are recombinantly fused or chemically conjugated (including both covalent and non-covalent conjugations) to a heterologous protein or polypeptide (or fragment of a polypeptide of at least 10, at least 20, at least 30, at least 40, at least 50, at least 60, at least 70, at least 80, at least 90 or at least 100 amino acids) to generate fusion proteins. In particular, the invention provides formulations of fusion proteins comprising an antigen-binding fragment of an antibody described herein (for example, but not limited to, a Fab fragment, Fd fragment, Fv fragment, $F(ab)_2$ fragment, a VH domain, a VH CDR, a VL domain or a VL CDR) and a heterologous protein, polypeptide, or peptide. Methods for fusing or conjugating proteins, polypeptides, or peptides to an antibody (including antibody fragment thereof) are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341 (said references are incorporated herein by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (for example, but not limited to, antibodies or fragments thereof with higher affinities and lower dissociation rates). See, generally, U.S. Pat. Nos. 5,605,793, 5,811, 238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies (including antibody fragments thereof), or the encoded antibodies or fragments thereof, may be altered by being subjected to random mutagenesis by error-prone PCR, random nucleotide insertion or other methods prior to recombination. A polynucleotide encoding an antibody (including antibody fragment thereof) thereof may be recombined with one or more components, motifs, sections, parts, domains, fragments, etc. of one or more heterologous molecules.

Moreover, the antibodies (including antibody fragments thereof) can be fused to marker sequences, such as a peptide to facilitate purification. The marker amino acid sequence may be a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder (for example, but not limited to, an autoimmune disorder) as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In,), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Sn; and positron emitting metals using various positron emission tomographies, and noradioactive paramagnetic metal ions.

Alternatively, an antibody can be conjugated to a second antibody to form an antibody heteroconjugate as described by Segal in U.S. Pat. No. 4,676,980, which is incorporated herein by reference in its entirety.

The therapeutic moiety or drug conjugated to an antigen of interest (e.g. IL-5R) or fragment thereof should be chosen to achieve the desired prophylactic or therapeutic effect(s) for a particular disease or disorder, for example, a disease or disorder associated with or characterized by aberrant expression and/or activity of an interferon alpha polypeptide, a disease or disorder associated with or characterized by aberrant expression and/or activity of the interferon alpha receptor or one or more subunits thereof, an autoimmune disease, an autoimmune disease, transplant rejection, graft versus host disease, or one or more symptoms thereof, in a subject. A clinician or other medical personnel should consider the following when deciding on what to conjugate to an antibody of interest, for example, an antibody that specifically binds to an interferon alpha polypeptide or fragment thereof: the nature of the disease, the severity of the disease, and the condition of the subject.

The antibodies (including antibody fragments thereof) that specifically bind to an antigen can be produced by any method known in the art for the synthesis of antibodies, in particular, by chemical synthesis or by recombinant expression techniques (see, US Patent Publication 2007/0014724A1).

Polyclonal antibodies specific for an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T Cell Hybridomas 563 681 (Elsevier, N.Y., 1981), and Harlow et al., Using Antibodies: A laboratory Manual, Cold Spring Harbor Laboratory Press (1999) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a non-murine antigen and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization multiple sites) technique can be used to immunize an animal (Kilpatrack et al., 1997, Hybridoma 16:381-9, incorporated herein by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

The present invention provides methods of generating monoclonal antibodies as well as antibodies produced by the method comprising culturing a hybridoma cell secreting an antibody of the invention wherein the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments which recognize specific particular epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; International application No. PCT/GB91/01134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, 5,969,108, 6,33,187, 5,824,520, and 5,702,892; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. The vectors for expressing the VH or VL domains may comprise an EF-1α promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, for example, but not limited to, IgG, using techniques known to those of skill in the art.

For some uses, including in vivo use of antibodies in humans and in vitro detection assays, it may be appropriate to use humanized antibodies or chimeric antibodies. Completely human antibodies and humanized antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65 93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633, 425, 5,569,825, 5,661,016, 5,545,806, 5,814,318, and 5,939, 598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331, 415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')2, Fabc, Fv) in which all or substantially all of the CDR regions correspond to those of a non human immunoglobulin (i.e., donor antibody) and all or substantially all of the framework regions are those of a human immunoglobulin consensus sequence. In one embodiment, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and greater than 95%. Humanized antibody can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678 84 (1997), Roguska et al., Protein Eng. 9(10):895 904 (1996), Couto et al., Cancer Res. 55 (23 Supp):5973s 5977s (1995), Couto et al., Cancer Res. 55(8):1717 22 (1995), Sandhu J S, Gene 150(2):409 10 (1994), and Pedersen et al., J. Mol. Biol. 235(3):959 73 (1994). Often, framework residues in the framework regions will be substituted with the corresponding residue from the CDR donor antibody to alter, preferably improve, antigen binding. These framework substitutions are identified by methods well known in the art, for example, but not limited to, by modeling of the interactions of the CDR and framework residues to identify framework residues important for antigen binding and sequence comparison to identify unusual framework residues at particular positions (see, e.g., Queen et al., U.S. Pat. No. 5,585,089; and Riechmann et al., 1988, Nature 332:323, which are incorporated herein by reference in their entireties).

Single domain antibodies, for example, antibodies lacking the light chains, can be produced by methods well-known in the art. See Riechmann et al., 1999, J. Immuno. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that specifically bind to an antigen (e.g. IL-5R) can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

Recombinant expression of an antibody of the invention (e.g., a heavy or light chain of an antibody of the invention or a fragment thereof or a single chain antibody of the invention) may require construction of an expression vector containing a polynucleotide that encodes the antibody. Once a polynucleotide encoding an antibody molecule, heavy or light chain of an antibody, or fragment thereof has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody (including antibody fragment thereof), or a heavy or light chain CDR, operably linked to a promoter. Such vectors may include the nucleotide sequence encoding the constant region of the antibody molecule (see, e.g., International Publication No. WO 86/05807; International Publication No. WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or fragment thereof, or a single chain antibody of the invention, operably linked to a heterologous promoter. In specific embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (for example, but not limited to, E. coli and B. subtilis) transformed with recombinant bacteriophage DNA, plasmid DNA or cosmid DNA expression vectors containing antibody coding sequences; yeast (for example, but not limited to, Saccharomyces Pichia) transformed with recombinant yeast expression vectors containing antibody coding sequences; insect cell systems infected with recombinant virus expression vectors (for example, but not limited to, baculovirus) containing antibody coding sequences; plant cell systems infected with recombinant virus expression vectors (for example, but not limited to, cauliflower mosaic virus, CaMV; tobacco mosaic virus, TMV) or transformed with recombinant plasmid expression vectors (for example, but not limited to, Ti plasmid) containing antibody coding sequences; or mammalian cell systems (for example, but not limited to, COS, CHO, BHK, 293, NS0, and 3T3 cells) harboring recombinant expression constructs containing promoters derived from the genome of mammalian cells (for example, but not limited to, metallothionein promoter) or from mammalian viruses (for example, but not limited to, the adenovirus late promoter; the vaccinia virus 7.5K promoter). Bacterial cells such as Escherichia coli, and eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding antibodies of the invention, derivative, analog, or fragment thereof is regulated by a constitutive promoter, inducible promoter or tissue specific promoter.

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified may be desirable. Such vectors include, but are not limited to, the E. coli expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (for example, but not limited to, glycosylation) and processing (for example, but not limited to, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression is may be used. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

In one embodiment, the cell line used to express the IL-5R binding molecule is a cell that does not fucosylate the Fc region of the IL-5R binding molecule. Nonlimiting examples of these types of cells are found in U.S. Pat. No. 6,946,292, and U.S. Patent Application Publication Nos. 2006/0078991A1, 2004/0110282A1, 2006/0024800A1, 2005/0216958A1, 2004/0132140, and 2004/0259150. In a specific embodiment, the IL-5R binding molecule is a humanized, afucosylated IgG1 anti-IL-5R cc chain monoclonal antibody. In a further specific embodiment, the antibody is MEDI-563 (also known as BIW-8405). In yet a further specific embodiment, the antibody is not MEDI-563.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk−, hgprt− or aprt− cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62: 191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

For the IL-5R binding molecules (e.g. antibodies, proteins, polypeptides, peptides and fusion proteins) encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In a specific embodiment, the dosage of IL-5R binding molecule administered to prevent, treat, manage, and/or ameliorate a disease or one or more symptoms thereof in a patient is 150 µg/kg or less, preferably 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of a patient's body weight. In another embodiment, the dosage of the IL-5R binding molecules of the invention administered to prevent, treat, manage, and/or ameliorate a hyperproliferative disease, or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

In other embodiments, a subject is administered one or more doses of an effective amount of one or therapies of the invention, wherein the dose of an effective amount achieves a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml of the therapies of the invention. In yet other embodiments, a subject is administered a dose of an effective amount of one of the IL-5R binding molecule of the invention to achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml of the IL-5R binding molecule and a subsequent dose of an effective amount of one or more IL-5R binding molecule of the invention is administered to maintain a serum titer of at least 0.1 µg/ml, 0.5 µg/ml, 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml. In accordance with these embodiments, a subject may be administered 1, 2, 3, 4, 5, 6, 7, 8, 9, 10, 11, 12 or more subsequent doses.

In a specific embodiment, the invention provides methods of preventing, treating, managing, or ameliorating an eosinophil mediated disease or one or more symptoms thereof, said method comprising administering to a subject in need thereof a dose of at least 10 µg, preferably at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, at least 100 µg, at least 105 µg, at least 110 µg, at least 115 µg, or at least 120 µg of one or more therapies (e.g., therapeutic or prophylactic agents), combination therapies, or compositions of the invention. In another embodiment, the invention provides a method of preventing, treating, managing, and/or ameliorating an eosinophil mediated disease or disorder or one or more symptoms thereof, said methods comprising administering to a subject in need thereof a dose of at least 10 µg, preferably at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 pig, at least 95 µg, at least 100 µg, at least 105 µg, at least 110 µg, at least 115 µg, or at least 120 µg of one or more IL-5R binding molecules, combination therapies, or compositions of the invention once every 3 days, preferably, once every 4 days, once every 5 days, once every 6 days, once every 7 days, once every 8 days, once every 10 days, once every two weeks, once every three weeks, or once a month.

The present invention provides methods of preventing, treating, managing, or preventing an eosinophil mediated disorder or disease or one or more symptoms thereof, said method comprising: (a) administering to a subject in need thereof one or more doses of a prophylactically or therapeutically effective amount of one or more IL-5R binding molecules, combination therapies, or compositions of the invention; and (b) monitoring the plasma level/concentration of the said administered IL-5R binding molecules in said subject after administration of a certain number of doses of the said therapies (e.g., therapeutic or prophylactic agents). Moreover, preferably, said certain number of doses is 1, 2, 3, 4, 5, 6, 7, 8, 9, 10, 11, or 12 doses of a prophylactically or therapeutically effective amount one or more IL-5R binding molecules, compositions, or combination therapies of the invention.

In a specific embodiment, the invention provides a method of preventing, treating, managing, and/or ameliorating an eosinophil mediated disorder or disease or one or more symptoms thereof, said method comprising: (a) administering to a subject in need thereof a dose of at least 10 µg (preferably at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg) of one or more therapies (e.g., therapeutic or prophylactic agents) of the invention; and (b) administering one or more subsequent doses to said subject when the plasma level of the IL-5R binding molecule administered in said subject is less than 0.1 µg/ml, preferably less than 0.25 µg/ml, less than 0.5 µg/ml, less than 0.75 µg/ml, or less than 1 µg/ml. In another embodiment, the invention provides a method of preventing, treating, managing, and/or ameliorating an eosinophil mediated disorder or disease or one or more symptoms thereof, said method comprising: (a) administering to a subject in need thereof one or more doses of at least 10 µg (preferably at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg) of one or more IL-5R binding molecules of the invention; (b) monitoring the plasma level of the administered IL-5R binding molecules in said subject after the administration of a certain number of doses; and (c) administering a subsequent dose of IL-5R binding molecules of the invention when the plasma level of the administered IL-5R binding molecule in said subject is less than 0.1 µg/ml, preferably less than 0.25 µg/ml, less than 0.5 µg/ml, less than 0.75 µg/ml, or less than 1 µg/ml. In certain embodiments, said certain number of doses is 1, 2, 3, 4, 5, 6, 7, 8, 9, 10, 11, or 12 doses of an effective amount of one or more IL-5R binding molecules of the invention.

Therapies (e.g., prophylactic or therapeutic agents), other than the IL-5R binding molecules of the invention, which have been or are currently being used to prevent, treat, manage, and/or ameliorate a hyperproliferative disease or one or more symptoms thereof can be administered in combination with one or more IL-5R binding molecules according to the methods of the invention to treat, manage, prevent, and/or ameliorate an eosinophil mediated disorder or disease or one or more symptoms thereof. Preferably, the dosages of prophylactic or therapeutic agents used in combination therapies of the invention are lower than those which have been or are currently being used to prevent, treat, manage, and/or ameliorate an eosinophil mediated disorder or disease or one or more symptoms thereof. The recommended dosages of agents currently used for the prevention, treatment, management, or amelioration of a hyperproliferative disease or one or more symptoms thereof can be obtained from any reference in the art including, but not limited to, Hardman et al., eds., 2001, Goodman & Gilman's The Pharmacological Basis Of Basis Of Therapeutics, 10th ed., Mc-Graw-Hill, New York; Physician's Desk Reference (PDR) 58th ed., 2004, Medical Economics Co., Inc., Montvale, N.J., which are incorporated herein by reference in its entirety.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In other embodiments, two or more therapies are administered within the same patient visit.

In certain embodiments, one or more IL-5R binding molecules of the invention and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same IL-5R binding molecule of the invention may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than an IL-5R binding molecule of the invention may be repeated and the administration may be separated by at least at least 1 day, 2 days, 3 days, 5 days, 10 days, 15 days, 30 days, 45 days, 2 months, 75 days, 3 months, or at least 6 months.

In a specific embodiment, the IL-5R binding molecule is administered as a single intravenous dose of 0.03 mg/kg.

The present invention provides methods of preventing, treating, managing, or preventing an eosinophil mediated disorder or disease or one or more symptoms thereof, said method comprising: (a) administering to a subject in need thereof one or more doses of a prophylactically or therapeutically effective amount of one or more IL-5R binding molecules, combination therapies, or compositions of the invention; and (b) monitoring at least one disease indicator or symptom in the subject prior to and following the administration of one or more doses of said therapies (e.g., therapeutic or prophylactic agents).

In one embodiment, the subject suffers from COPD.

In one embodiment, the subject suffers from mild persistent or mild intermittent asthma as defined by the by the 2002 Expert Panel report of the NAEPP.

In one embodiment, the disease indicator or symptom in the subject is monitored prior to and following the administration of a single dose of one or more IL-5R binding molecules. In another embodiment, the disease indicator or symptom in the subject is monitored prior to and following the administration of multiple doses of one or more IL-5R binding molecules.

In one embodiment, the disease indicator or symptom is a self-assessed Asthma Symptom Score. A non-limiting example of an Asthma Symptom Score is a self-assessed score recorded daily by the subject at home. The score grades asthma symptoms for the past 24 hours, based on the severity of morning, nocturnal, and daytime symptoms. The symptoms and assigned scores are described in Table 1. The daily maximum score is 9, minimum is 0. Subjects self-assess and record on a continuous basis.

TABLE 1

Asthma Symptom Score key: Nocturnal lasts from going to bed until awakening in the morning. Morning lasts from awakening until 1 hour after awakening. Daytime begins 1 hour after awakening and ends at bedtime.

| | Nocturnal symptoms |
|---|---|
| 0 | I did not wake up because of breathing problems. |
| 1 | I awoke once because of my breathing problems, but did not use my rescue medication. |
| 2 | I awoke once because of my breathing problems, but my rescue medication controlled my symptoms. |
| 3 | I awoke more than once because of my breathing problems, but my rescue medication controlled my symptoms. |
| 4 | I had difficulty sleeping because of my breathing problems even though I used my rescue medications. |
| | Morning symptoms |
| 0 | No |
| 1 | Yes |
| | Daytime symptoms |
| 0 | No symptoms at all; unrestricted activity |
| 1 | Symptoms caused little or no discomfort; unrestricted activity |
| 2 | Symptoms caused some discomfort; at times limiting strenuous activity |
| 3 | Symptoms caused moderate discomfort; at times limiting routine activity |
| 4 | Symptoms occurred at rest, caused marked discomfort, and usually limited routine activity |

In one embodiment, a subject has an Asthma Symptom Score of X prior to the administration of the one or more doses of one or more IL-5R binding molecules and an Asthma Symptom Score of X-Y following the administration of the one or more doses of one or more IL-5R binding molecules, wherein X is 1, 2, 3, 4, 5, 6, 7, 8, or 9, wherein Y is 1, 2, 3, 4, 5, 6, 7, 8, or 9, and wherein the post-administration Score is never below 0.

In one embodiment, a subject has an Asthma Symptom Score of between 0 and 9 prior to the administration of the one or more doses of one or more IL-5R binding molecules. In one embodiment, a subject has an Asthma Symptom Score between 0 and 3, between 1 and 4, between 2 and 5, between 3 and 5, between 4 and 7, between 5 and 8 or between 6 and 9 prior to the administration of the one or more doses of one or more IL-5R binding molecules. In one embodiment, a subject has an Asthma Symptom Score of 1, 2, 3, 4, 5, 6, 7, 8 or 9 prior to the administration of the one or more doses of one or more IL-5R binding molecules. In one embodiment, a subject has an Asthma Symptom Score of I prior to the administration of the one or more doses of one or more IL-5R binding molecules. In one embodiment, a subject has an Asthma Symptom Score of 2 prior to the administration of the one or more doses of one or more IL-5R binding molecules. In one embodiment, a subject has an Asthma Symptom Score of 3 prior to the administration of the one or more doses of one or more IL-5R binding molecules. In one embodiment, a subject has an Asthma Symptom Score of 4 prior to the administration of the one or more doses of one or more IL-5R binding molecules. In one embodiment, a subject has an Asthma Symptom Score of 5 prior to the administration of the one or more doses of one or more IL-5R binding molecules. In one embodiment, a subject has an Asthma Symptom Score of 6 prior to the administration of the one or more doses of one or more IL-5R binding molecules. In one embodiment, a subject has an Asthma Symptom Score of 7 prior to the administration of the one or more doses of one or more IL-5R binding molecules. In one embodiment, a subject has an Asthma Symptom Score of 8 prior to the administration of the one or more doses of one or more IL-5R binding molecules. In one embodiment, a subject has an Asthma Symptom Score of 9 prior to the administration of the one or more doses of one or more IL-5R binding molecules.

In one embodiment, a subject has an Asthma Symptom Score of between 0 and 9 following the administration of the one or more doses of one or more IL-5R binding molecules. In one embodiment, a subject has an Asthma Symptom Score between 0 and 3, between 1 and 4, between 2 and 5, between 3 and 5, between 4 and 7, between 5 and 8 or between 6 and 9 following the administration of the one or more doses of one or more IL-5R binding molecules. In one embodiment, a subject has an Asthma Symptom Score of 1, 2, 3, 4, 5, 6, 7, 8 or 9 following the administration of the one or more doses of one or more IL-5R binding molecules. In one embodiment, a subject has an Asthma Symptom Score of I following the administration of the one or more doses of one or more IL-5R binding molecules. In one embodiment, a subject has an Asthma Symptom Score of 2 following the administration of the one or more doses of one or more IL-5R binding molecules. In one embodiment, a subject has an Asthma Symptom Score of 3 following the administration of the one or more doses of one or more IL-5R binding molecules. In one embodiment, a subject has an Asthma Symptom Score of 4 following the administration of the one or more doses of one or more IL-5R binding molecules. In one embodiment, a subject has an Asthma Symptom Score of 5 following the administration of the one or more doses of one or more IL-5R binding molecules. In one embodiment, a subject has an Asthma Symptom Score of 6 following the administration of the one or more doses of one or more IL-5R binding molecules. In one embodiment, a subject has an Asthma Symptom Score of 7 following the administration of the one or more doses of one or more IL-5R binding molecules. In one embodiment, a subject has an Asthma Symptom Score of 8 following the administration of the one or more doses of one or more IL-5R binding molecules. In one embodiment, a subject has an Asthma Symptom Score of 9 following the administration of the one or more doses of one or more IL-5R binding molecules.

In one embodiment, the Asthma Symptom Score of a subject is lower following the administration of one or more doses of one or more IL-5R binding molecules than prior to the administration of one or more doses of one or more IL-5R binding molecules wherein the post-administration Score is never lower than 0. In a specific embodiment, the Asthma Symptom Score is 1 point lower. In a specific embodiment, the Asthma Symptom Score is 9 point lower. In a specific embodiment, the Asthma Symptom Score is 2 point lower. In a specific embodiment, the Asthma Symptom Score is 3 point lower. In a specific embodiment, the Asthma Symptom Score is 4 point lower. In a specific embodiment, the Asthma Symptom Score is 5 point lower. In a specific embodiment, the Asthma Symptom Score is 6 point lower. In a specific embodiment, the Asthma Symptom Score is 7 point lower. In a specific embodiment, the Asthma Symptom Score is 8 point lower. In a specific embodiment, the Asthma Symptom Score is at least 1 point lower. In a specific embodiment, the Asthma Symptom Score is at least 9 point lower. In a specific embodiment, the Asthma Symptom Score is at least 2 point lower. In a specific embodiment, the Asthma Symptom Score is at least 3 point lower. In a specific embodiment, the Asthma Symptom Score is at least 4 point lower. In a specific embodiment, the Asthma Symptom Score is at least 5 point lower. In a specific embodiment, the Asthma Symptom Score is at least 6 point lower. In a specific embodiment, the Asthma Symptom Score is at least 7 point lower. In a specific embodiment, the Asthma Symptom Score is at least 8 point lower.

In one embodiment, the disease indicator or symptom is Fractional Exhaled Nitric Oxide (FENO). FENO may be measured according to the combined recommendations of the European Respiratory Society and the American Thoracic Society (American Thoracic Society, European Respiratory Society. (2005) ATS/ERS Recommendations for Standardized Procedures for the Online and Offline Measurements of Exhaled Lower Respiratory Nitric Oxide and Nasal Nitric Oxide, 2005. Am J Respir Crit Care Med. 171: 912-930). The FENO measurements may be performed using the NIOX at a 50 ml/s flow rate (ATS standard).

In one embodiment, a subject has a FENO of between 20 and 500 ppb prior to the administration of the one or more doses of one or more IL-5R binding molecules. In one embodiment, a subject has a FENO between 20 and 500 ppb, between 20 and 400 ppb, between 20 and 300 ppb, between 20 and 200 ppb, between 50 and 500 ppb, between 100 and 500 ppb, between 150 and 500 ppb, between 200 and 500 ppb, between 20 and 50 ppb, between 50 and 100 ppb, between 100 and 200 ppb, between 200 and 300 ppb, between 300 and 500 ppb prior to the administration of the one or more doses of one or more IL-5R binding molecules. In one embodiment, a subject has a FENO of at least 50 ppb, at least 100 ppb, at least 150 ppb, at least 200 ppb, at least 250 ppb, at least 300 ppb, at least 350 ppb, at least 400 ppb prior to the administration of the one or more doses of one or more IL-5R binding molecules. In one embodiment, a subject has a FENO of 50 ppb prior to the administration of the one or more doses of one or more IL-5R binding molecules. In one embodiment, a subject has a FENO of 100 ppb prior to the administration of the one or more doses of one or more IL-5R binding molecules. In one embodiment, a subject has a FENO of 150 ppb prior to the administration of the one or more doses of one or more IL-5R binding molecules. In one embodiment, a subject has a FENO of 200 ppb prior to the administration of the one or more doses of one or more IL-5R binding molecules. In one embodiment, a subject has a FENO of 250 ppb prior to the administration of the one or more doses of one or more IL-5R binding molecules. In one embodiment, a subject has a FENO of 300 ppb prior to the administration of the one or more doses of one or more IL-5R binding molecules. In one embodiment, a subject has a FENO of 350 ppb prior to the administration of the one or more doses of one or more IL-5R binding molecules. In one embodiment, a subject has a FENO of 400 ppb prior to the administration of the one or more doses of one or more IL-5R binding molecules.

In one embodiment, a subject has a FENO of between 20 and 500 ppb following the administration of the one or more doses of one or more IL-5R binding molecules. In one embodiment, a subject has a FENO between 20 and 500 ppb, between 20 and 400 ppb, between 20 and 300 ppb, between 20 and 200 ppb, between 50 and 500 ppb, between 100 and 500 ppb, between 150 and 500 ppb, between 200 and 500 ppb, between 20 and 50 ppb, between 50 and 100 ppb, between 100 and 200 ppb, between 200 and 300 ppb, between 300 and 500 ppb following the administration of the one or more doses of one or more IL-5R binding molecules. In one embodiment, a subject has a FENO of at most 50 ppb, at most 100 ppb, at most 150 ppb, at most 200 ppb, at most 250 ppb, at most 300 ppb, at most 350 ppb, at most 400 ppb following the administration of the one or more doses of one or more IL-5R binding molecules. In one embodiment, a subject has a FENO of at most 20 ppb following the administration of the one or more doses of one or more IL-5R binding molecules. In one embodiment, a subject has a FENO of at most 50 ppb following the administration of the one or more doses of one or more IL-5R binding molecules. In one embodiment, a subject has a FENO of at most 100 ppb following the administration of the one or more doses of one or more IL-5R binding molecules. In one embodiment, a subject has a FENO of at most 150 ppb following the administration of the one or more doses of one or more IL-5R binding molecules. In one embodiment, a subject has a FENO of at most 200 ppb following the administration of the one or more doses of one or more IL-5R binding molecules. In one embodiment, a subject has a FENO of at most 250 ppb following the administration of the one or more doses of one or more IL-5R binding molecules. In one embodiment, a subject has a FENO of at most 300 ppb following the administration of the one or more doses of one or more IL-5R binding molecules. In one embodiment, a subject has a FENO of at most 350 ppb following the administration of the one or more doses of one or more IL-5R binding molecules. In one embodiment, a subject has a FENO of at most 400 ppb following the administration of the one or more doses of one or more IL-5R binding molecules.

In one embodiment, the FENO of a subject is lower following the administration of one or more doses of one or more IL-5R binding molecules than prior to the administration of one or more doses of one or more IL-5R binding molecules, wherein the FENO is never below 0 ppb. In a specific embodiment, the FENO is at least 50 ppb lower. In a specific embodiment, the FENO is at least 100 ppb lower. In a specific embodiment, the FENO is at least 150 ppb lower. In a specific embodiment, the FENO is at least 200 ppb lower. In a specific embodiment, the FENO is at least 250 ppb lower. In a specific embodiment, the FENO is at least 300 ppb lower. In a specific embodiment, the FENO is at least 10% lower. In a specific embodiment, the FENO is at least 20% lower. In a specific embodiment, the FENO is at least 30% lower. In a specific embodiment, the FENO is at least 40% lower. In a specific embodiment, the FENO is at least 50% lower. In a specific embodiment, the FENO is at least 60% lower. In a specific embodiment, the FENO is at least 70% lower. In a specific embodiment, the FENO is at least 80% lower. In a specific embodiment, the FENO is at least 90% lower. In a specific embodiment, the FENO is 10% lower. In a specific embodiment, the FENO is 20% lower. In a specific embodiment, the FENO is 30% lower. In a specific embodiment, the FENO is 40% lower. In a specific embodiment, the FENO is 50% lower. In a specific embodiment, the FENO is 60% lower. In a specific embodiment, the FENO is 70% lower. In a specific embodiment, the FENO is 80% lower. In a specific embodiment, the FENO is 90% lower.

In one embodiment, the disease indicator or symptom is Eosinophil Cationic Protein (ECP). Serum ECP levels may be assessed using any methods known to one of skill in the art, for example, but not limited to ELISA assay, radioimmunoassay. Serum ECP levels may be measured by any one of the commercially available assays.

In one embodiment, a subject has a serum ECP of between 20 and 500 ng/ml prior to the administration of the one or more doses of one or more IL-5R binding molecules. In one embodiment, a subject has a serum ECP between 20 and 200 ng/ml, between 20 and 150 ng/ml, between 20 and 100 ng/ml, between 20 and 50 ng/ml, between 30 and 200 ng/ml, between 40 and 200 ng/ml, between 50 and 200 ng/ml, between 30 and 100 ng/ml, between 30 and 80 ng/ml, between 30 and 70 ng/ml, between 20 and 80 ng/ml, between 20 and 70 ng/ml, between 20 and 60 ng/ml prior to the administration of the one or more doses of one or more IL-5R binding molecules. In one embodiment, a subject has a serum ECP of at least 20 ng/ml, at least 30 ng/ml, at least 40 ng/ml, at least 50 ng/ml, at least 60 ng/ml, at least 100 ng/ml, at least 150 ng/ml, at least 200 ng/ml prior to the administration of the one or more doses of one or more IL-5R binding molecules. In one embodiment, a subject has a serum ECP of 25 ng/ml prior to the administration of the one or more doses of one or more IL-5R binding molecules. In one embodiment, a subject has a serum ECP of 30 ng/ml prior to the administration of the one or more doses of one or more IL-5R binding molecules. In one embodiment, a subject has a serum ECP of 35 ng/ml prior to the administration of the one or more doses of one or more IL-5R binding molecules. In one embodiment, a subject has a serum ECP of 40 ng/ml prior to the administration of the one or more doses of one or more IL-5R binding molecules. In one embodiment, a subject has a serum ECP of 50 ng/ml prior to the administration of the one or more doses of one or more IL-5R binding molecules. In one embodiment, a subject has a serum ECP of 60 ng/ml prior to the administration of the one or more doses of one or more IL-5R binding molecules. In one embodiment, a subject has a serum ECP of 70 ng/ml prior to the administration of the one or more doses of one or more IL-5R binding molecules. In one embodiment, a subject has a serum ECP of 80 ng/ml prior to the administration of the one or more doses of one or more IL-5R binding molecules. In one embodiment, a subject has a serum ECP of 100 ng/ml prior to the administration of the one or more doses of one or more IL-5R binding molecules. In one embodiment, a subject has a serum ECP of 150 ng/ml prior to the administration of the one or more doses of one or more IL-5R binding molecules. In one embodiment, a subject has a serum ECP of 200 ng/ml prior to the administration of the one or more doses of one or more IL-5R binding molecules.

In one embodiment, a subject has no detectable serum ECP following the administration of the one or more doses of one or more IL-5R binding molecules. In one embodiment, a subject has a serum ECP of between 1 and 500 ng/ml following the administration of the one or more doses of one or more IL-5R binding molecules. In one embodiment, a subject has a serum ECP between 1 and 200 ng/ml, between 1 and 150 ng/ml, between 1 and 100 ng/ml, between 1 and 50 ng/ml, between 1 and 20 ng/ml, between 10 and 200 ng/ml, between 10 and 100 ng/ml, between 10 and 50 ng/ml, between 20 and 100 ng/ml, between 20 and 50 ng/ml following the administration of the one or more doses of one or more IL-5R binding molecules. In one embodiment, a subject has a serum ECP of at most 1 ng/ml, at most 5 ng/ml, at most 10 ng/ml, at most 20 ng/ml, at most 30 ng/ml, at most 50 ng/ml following the administration of the one or more doses of one or more IL-5R binding molecules. In one embodiment, a subject has a serum ECP of at most 1 ng/ml following the administration of the one or more doses of one or more IL-5R binding molecules. In one embodiment, a subject has a serum ECP of at most 5 ng/ml following the administration of the one or more doses of one or more IL-5R binding molecules. In one embodiment, a subject has a serum ECP of at most 10 ng/ml following the administration of the one or more doses of one or more IL-5R binding molecules. In one embodiment, a subject has a serum ECP of at most 15 ng/ml following the administration of the one or more doses of one or more IL-5R binding molecules. In one embodiment, a subject has a serum ECP of at most 20 ng/ml following the administration of the one or more doses of one or more IL-5R binding molecules. In one embodiment, a subject has a serum ECP of at most 25 ng/ml following the administration of the one or more doses of one or more IL-5R binding molecules. In one embodiment, a subject has a serum ECP of at most 30 ng/ml following the administration of the one or more doses of one or more IL-5R binding molecules.

In one embodiment, the serum ECP of a subject is lower following the administration of one or more doses of one or more IL-5R binding molecules than prior to the administration of one or more doses of one or more IL-5R binding molecules, wherein the serum ECP is never below 0 ng/ml. In a specific embodiment, the serum ECP is at least 50 ng/ml lower. In a specific embodiment, the serum ECP is at least 100 ng/ml lower. In a specific embodiment, the serum ECP is at least 150 ng/ml lower. In a specific embodiment, the serum ECP is at least 200 ng/ml lower. In a specific embodiment, the serum ECP is at least 250 ng/ml lower. In a specific embodiment, the serum ECP is at least 300 ng/ml lower. In a specific embodiment, the serum ECP is at least 10% lower. In a specific embodiment, the serum ECP is at least 20% lower. In a specific embodiment, the serum ECP is at least 30% lower. In a specific embodiment, the serum ECP is at least 40% lower. In a specific embodiment, the serum ECP is at least 50% lower. In a specific embodiment, the serum ECP is at least 60% lower. In a specific embodiment, the serum ECP is at least 70% lower. In a specific embodiment, the serum ECP is at least 80% lower. In a specific embodiment, the serum ECP is at least 90% lower. In a specific embodiment, the serum ECP is at least 95% lower. In a specific embodiment, the serum ECP is 10% lower. In a specific embodiment, the serum ECP is 20% lower. In a specific embodiment, the serum ECP is 30% lower. In a specific embodiment, the serum ECP is 40% lower. In a specific embodiment, the serum ECP is 50% lower. In a specific embodiment, the serum ECP is 60% lower. In a specific embodiment, the serum ECP is 70% lower. In a specific embodiment, the serum ECP is 80% lower. In a specific embodiment, the serum ECP is 90% lower. In a specific embodiment, the serum ECP is 95% lower. In a specific embodiment, the serum ECP is 99% lower.

In one embodiment, a subject has no detectable serum ECP following the administration of the one or more doses of one or more IL-5R binding molecules. In a specific embodiment, the serum ECP level remains undetectable for at least about 1 day, at least about 2 days, at least about 3 days, at least about 4 days, at least about 5 days, at least about 6 days, at least about 7 days, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 12 weeks, at least about 14 weeks, at least about 16 weeks, at least about 20 weeks, or at least about 25 weeks.

In one embodiment, the disease indicator or symptom is Methacholine Challenge Test (MCT) MCT may be performed according to American Thoracic Society (ATS) guidelines (Guidelines for Methacholine and Exercise Testing—1999. (2000) Am J Respir Crit Care Med. 161:309-329) in the presence of a physician who is experienced in the management of bronchospasm and with appropriate therapeutic agents immediately available. Briefly, the spirometer used is calibrated according to the guidelines of the ATS. The nebulizer used must produce a particle size with mass median aerodynamic diameter (MMAD) of 1-4 microns and flow of 0.13±10% mL/min. Methacholine from an FDA approved source is used and diluted with sterile normal saline. Inhalation challenge may be conducted using either 2 minutes of tidal breathing or the five-breath dosimeter method as described in the referenced publication. Concentrations of methacholine are administered according to the established practice of the investigator, but within the range of 0.06 mg/dL to 25.0 mg/dL. $FEV_1$ is measured 30 and 90 seconds after completion of each dose and the higher of the two values recorded. Increasing concentrations is administered until the $FEV_1$ has been seen to fall at least 20% from the baseline value. PC20 is the concentration of methacholine that leads to at least 20% fall in $FEV_1$ from the baseline value. After completion of the final dose the subject may be given albuterol by metered-dose inhaler or nebulizer at the discretion of the Principal Investigator.

In one embodiment, a subject has a PC20 of between 0.06 and 25 mg/dL prior to the administration of the one or more doses of one or more IL-5R binding molecules. In one embodiment, a subject has a PC20 between 0.06 and 25 mg/dL, between 0.1 and 10 mg/dL, between 0.06 and 3 mg/dL, between 0.06 and 2 mg/dL, between 0.06 and 1 mg/dL, between 0.1 and 3 mg/dL, between 0.1 and 2 mg/dL, between 0.1 and 1 mg/dL, between 0.2 and 10 mg/dL, between 0.5 and 10 mg/dL, between 1 and 10 mg/dL, between 0.1 and 5 mg/dL, between 0.2 and 5 mg/dL, between 0.5 and 5 mg/dL, between 0.1 and 2 mg/dL, between 0.2 and 2 mg/dL, between 0.5 and 2 mg/dL, between 0.06 and 0.1 mg/dL, between 0.1 and 0.2 mg/dL, between 0.2 and 0.5 mg/dL, between 0.5 and 1 mg/dL, between 1 and 2 mg/dL, between 2 and 5 mg/dL, between 5 and 10 mg/dL prior to the administration of the one or more doses of one or more IL-5R binding molecules. In one embodiment, a subject has a PC20 of at most 0.1 mg/dL, at most 0.2 mg/dL, at most 0.4 mg/dL, at most 0.5 mg/dL, at most 1 mg/dL, at most 2 mg/dL, at most 5 mg/dL, at most 10 mg/dL prior to the administration of the one or more doses of one or more IL-5R binding molecules. In one embodiment, a subject has a PC20 of 10 mg/dL prior to the administration of the one or more doses of one or more IL-5R binding molecules. In one embodiment, a subject has a PC20 of 5 mg/dL prior to the administration of the one or more doses of one or more IL-5R binding molecules. In one embodiment, a subject has a PC20 of 2 mg/dL prior to the administration of the one or more doses of one or more IL-5R binding molecules. In one embodiment, a subject has a PC20 of 1 mg/dL prior to the administration of the one or more doses of one or more IL-5R binding molecules. In one embodiment, a subject has a PC20 of 0.5 mg/dL prior to the administration of the one or more doses of one or more IL-5R binding molecules. In one embodiment, a subject has a PC20 of 0.2 mg/dL prior to the administration of the one or more doses of one or more IL-5R binding molecules. In one embodiment, a subject has a PC20 of 0.1 mg/dL prior to the administration of the one or more doses of one or more IL-5R binding molecules.

In one embodiment, a subject has a PC20 of between 0.5 and 25 mg/dL following the administration of the one or more doses of one or more IL-5R binding molecules. In one embodiment, a subject has a PC20 between 1 and 25 mg/dL, between 2 and 25 mg/dL, between 5 and 25 mg/dL, between 10 and 25 mg/dL, between 1 and 10 mg/dL, between 2 and 10 mg/dL, between 2 and 10 mg/dL following the administration of the one or more doses of one or more IL-5R binding molecules. In one embodiment, a subject has a PC20 of at least 1 mg/dL, at least 2 mg/dL, at least 5 mg/dL, at least 10 mg/dL, at least 20 mg/dL following the administration of the one or more doses of one or more IL-5R binding molecules. In one embodiment, a subject has a PC20 of at least 0.2 mg/dL following the administration of the one or more doses of one or more IL-5R binding molecules. In one embodiment, a subject has a PC20 of at least 0.3 mg/dL following the administration of the one or more doses of one or more IL-5R binding molecules. In one embodiment, a subject has a PC20 of at least 0.4 mg/dL following the administration of the one or more doses of one or more IL-5R binding molecules. In one embodiment, a subject has a PC20 of at least 0.5 mg/dL following the administration of the one or more doses of one or more IL-5R binding molecules. In one embodiment, a subject has a PC20 of at least 0.7 mg/dL following the administration of the one or more doses of one or more IL-5R binding molecules. In one embodiment, a subject has a PC20 of at least 1 mg/dL following the administration of the one or more doses of one or more IL-5R binding molecules. In one embodiment, a subject has a PC20 of at least 2 mg/dl, following the administration of the one or more doses of one or more IL-5R binding molecules. In one embodiment, a subject has a PC20 of at least 5 mg/dL following the administration of the one or more doses of one or more IL-5R binding molecules. In one embodiment, a subject has a PC20 of at least 10 mg/dL following the administration of the one or more doses of one or more IL-5R binding molecules. In one embodiment, a subject has a PC20 of at least 20 mg/dL following the administration of the one or more doses of one or more IL-5R binding molecules. In one embodiment, a subject has a PC20 of at least 25 mg/dL following the administration of the one or more doses of one or more IL-5R binding molecules.

In one embodiment, the PC20 of a subject is higher following the administration of one or more doses of one or more IL-5R binding molecules than prior to the administration of one or more doses of one or more IL-5R binding molecules. In a specific embodiment, the PC20 is at least 0.3 mg/dL higher. In a specific embodiment, the PC20 is at least 0.5 mg/dL higher. In a specific embodiment, the PC20 is at least 0.7 mg/dL higher. In a specific embodiment, the PC20 is at least 1 mg/dL higher. In a specific embodiment, the PC20 is at least 3 mg/dL higher. In a specific embodiment, the PC20 is at least 5 mg/dL higher. In a specific embodiment, the PC20 is at least 10 mg/dL higher. In a specific embodiment, the PC20 is at least 15 mg/dL higher. In a specific embodiment, the PC20 is at least 20 mg/dL higher. In a specific embodiment, the PC20 is at least 2 fold higher. In a specific embodiment, the PC20 is at least 4 fold higher. In a specific embodiment, the PC20 is at least 8 fold higher. In a specific embodiment, the PC20 is at least 10 higher. In a specific embodiment, the PC20 is at least 12 fold higher. In a specific embodiment, the PC20 is at least 15 fold higher. In a specific embodiment, the PC20 is at least 20 fold higher. In a specific embodiment, the PC20 is 2 fold higher. In a specific embodiment, the PC20 is 4 fold higher. In a specific embodiment, the PC20 is 8 fold higher. In a specific embodiment, the PC20 is 10 fold higher. In a specific embodiment, the PC20 is 15 fold higher. In a specific embodiment, the PC20 is 60% higher. In a specific embodiment, the PC20 is 20 fold higher.

In one embodiment, the disease indicator or symptom is circulating eosinophil count. Circulating eosinophil count may be assessed using any methods known to one of skill in the art, for example, but not limited to histology, flow cytometry. Circulating eosinophil count may be measured by any one of the commercially available kits.

In one embodiment, a subject has a circulating eosinophil count of between 50 and 1000 cells/microL prior to the administration of the one or more doses of one or more IL-5R binding molecules. In one embodiment, a subject has a circulating eosinophil count between 50 and 1000 cells/microL, between 100 and 1000 cells/microL, between 150 and 1000 cells/microL, between 200 and 1000 cells/microL, between 250 and 1000 cells/microL, between 300 and 1000 cells/microL, between 400 and 1000 cells/microL, between 500 and 1000 cells/microL, between 50 and 500 cells/microL, between 100 and 500 cells/microL, between 100 and 400 cells/microL, between 150 and 500 cells/microL, between 200 and 500 cells/microL prior to the administration of the one or more doses of one or more IL-5R binding molecules. In one embodiment, a subject has a circulating eosinophil count of at least 50 cells/microL, at least 100 cells/microL, at least 150 cells/microL, at least 200 cells/microL, at least 250 cells/microL, at least 300 cells/microL, at least 400 cells/microL, at least 500 cells/microL prior to the administration of the one or more doses of one or more IL-5R binding molecules. In one embodiment, a subject has a circulating eosinophil count of 50 cells/microL prior to the administration of the one or more doses of one or more IL-5R binding molecules. In one embodiment, a subject has a circulating eosinophil count of 100 cells/microL prior to the administration of the one or more doses of one or more IL-5R binding molecules. In one embodiment, a subject has a circulating eosinophil count of 150 cells/microL prior to the administration of the one or more doses of one or more IL-5R binding molecules. In one embodiment, a subject has a circulating eosinophil count of 200 cells/microL prior to the administration of the one or more doses of one or more IL-5R binding molecules. In one embodiment, a subject has a circulating eosinophil count of 250 cells/microL prior to the administration of the one or more doses of one or more IL-5R binding molecules. In one embodiment, a subject has a circulating eosinophil count of 300 cells/microL prior to the administration of the one or more doses of one or more IL-5R binding molecules. In one embodiment, a subject has a circulating eosinophil count of 350 cells/microL prior to the administration of the one or more doses of one or more IL-5R binding molecules. In one embodiment, a subject has a circulating eosinophil count of 400 cells/microL prior to the administration of the one or more doses of one or more IL-5R binding molecules. In one embodiment, a subject has a circulating eosinophil count of 500 cells/microL prior to the administration of the one or more doses of one or more IL-5R binding molecules.

In one embodiment, a subject has a circulating eosinophil count of between 1 and 400 cells/microL following the administration of the one or more doses of one or more IL-5R binding molecules. In one embodiment, a subject has a circulating eosinophil count between 1 and 200 cells/microL, between 1 and 100 cells/microL, between 1 and 50 cells/microL, between 1 and 40 cells/microL, between 10 and 200 cells/microL, between 10 and 100 cells/microL, between 10 and 40 cells/microL, between 20 and 200 cells/microL, between 20 and 100 cells/microL, between 20 and 50 cells/microL following the administration of the one or more doses of one or more IL-5R binding molecules. In one embodiment, a subject has a circulating eosinophil count of at most 1 cells/microL, at most 5 cells/microL, at most 10 cells/microL, at most 20 cells/microL, at most 30 cells/microL, at most 40 cells/microL, at most 50 cells/microL, at most 60 cells/microL, at most 80 cells/microL, at most 100 cells/microL following the administration of the one or more doses of one or more IL-5R binding molecules. In one embodiment, a subject has a circulating eosinophil count of at most 1 cells/microL following the administration of the one or more doses of one or more IL-5R binding molecules. In one embodiment, a subject has a circulating eosinophil count of at most 5 cells/microL following the administration of the one or more doses of one or more IL-5R binding molecules. In one embodiment, a subject has a circulating eosinophil count of at most 10 cells/microL following the administration of the one or more doses of one or more IL-5R binding molecules. In one embodiment, a subject has a circulating eosinophil count of at most 20 cells/microL following the administration of the one or more doses of one or more IL-5R binding molecules. In one embodiment, a subject has a circulating eosinophil count of at most 30 cells/microL following the administration of the one or more doses of one or more IL-5R binding molecules. In one embodiment, a subject has a circulating eosinophil count of at most 40 cells/microL following the administration of the one or more doses of one or more IL-5R binding molecules. In one embodiment, a subject has a circulating eosinophil count of at most 50 cells/microL following the administration of the one or more doses of one or more IL-5R binding molecules. In one embodiment, a subject has a circulating eosinophil count of at most 60 cells/microL following the administration of the one or more doses of one or more IL-5R binding molecules. In one embodiment, a subject has a circulating eosinophil count of at most 80 cells/microL following the administration of the one or more doses of one or more IL-5R binding molecules.

In one embodiment, the circulating eosinophil count of a subject is lower following the administration of one or more doses of one or more IL-5R binding molecules than prior to the administration of one or more doses of one or more IL-5R binding molecules, wherein the circulating eosinophil count is never below 0 cells/microL. In a specific embodiment, the circulating eosinophil count is at least 50 cells/microL lower. In a specific embodiment, the circulating eosinophil count is at least 100 cells/microL lower. In a specific embodiment, the circulating eosinophil count is at least 150 cells/microL lower. In a specific embodiment, the circulating eosinophil count is at least 200 cells/microL lower. In a specific embodiment, the circulating eosinophil count is at least 250 cells/microL lower. In a specific embodiment, the circulating eosinophil count is at least 300 cells/microL lower. In a specific embodiment, the circulating eosinophil count is at least 10% lower. In a specific embodiment, the circulating eosinophil count is at least 20% lower. In a specific embodiment, the circulating eosinophil count is at least 30% lower. In a specific embodiment, the circulating eosinophil count is at least 40% lower. In a specific embodiment, the circulating eosinophil count is at least 50% lower. In a specific embodiment, the circulating eosinophil count is at least 60% lower. In a specific embodiment, the circulating eosinophil count is at least 70% lower. In a specific embodiment, the circulating eosinophil count is at least 80% lower. In a specific embodiment, the circulating eosinophil count is at least 90% lower. In a specific embodiment, the circulating eosinophil count is at least 95% lower. In a specific embodiment, the circulating eosinophil count is at least 99% lower. In a specific embodiment, the circulating eosinophil count is 10% lower. In a specific embodiment, the circulating eosinophil count is 20% lower. In a specific embodiment, the circulating eosinophil count is 30% lower. In a specific embodiment, the circulating eosinophil count is 40% lower. In a specific embodiment, the circulating eosinophil count is 50% lower. In a specific embodiment, the circulating eosinophil count is 60% lower. In a specific embodiment, the circulating eosinophil count is 70% lower. In a specific embodiment, the circulating eosinophil count is 80% lower. In a specific embodiment, the circulating eosinophil count is 90% lower. In a specific embodiment, the circulating eosinophil count is 95% lower. In a specific embodiment, the circulating eosinophil count is 99% lower.

In one embodiment, a subject has no detectable circulating eosinophil count following the administration of the one or more doses of one or more IL-5R binding molecules. In a specific embodiment, the circulating eosinophil count level remains undetectable for at least about 1 day, at least about 2 days, at least about 3 days, at least about 4 days, at least about 5 days, at least about 6 days, at least about 7 days, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 12 weeks, at least about 14 weeks, at least about 16 weeks, at least about 20 weeks, or at least about 25 weeks.

In one embodiment, the disease indicator or symptom is % eosinophil in induced sputum. % eosinophil in induced sputum may be assessed using any methods known to one of skill in the art, for example, but not limited to the methods described in Belda et al. (2000) *Am J Respir Crit Care Med* 161:475-478. % eosinophil in induced sputum may be determined by any one of the commercially available kits.

In one embodiment, a subject has a % eosinophil in induced sputum of between 0.1% and 10% prior to the administration of the one or more doses of one or more IL-5R binding molecules. In one embodiment, a subject has a % eosinophil in induced sputum between 0.1% and 2%, between 0.1% and 5%, between 0.5% and 2%, between 0.5% and 5%, between 0.5% and 10%, between 1% and 2%, between 1% and 5%, between 1% and 10%, between 2% and 5%, between 2% and 10%, between 3% and 5%, between 3% and 10%, between 1.5% and 5%, between 2.5% and 5%, prior to the administration of the one or more doses of one or more IL-5R binding molecules. In one embodiment, a subject has a % eosinophil in induced sputum of at least 0.1%, at least 0.5%, at least 1%, at least 1.5%, at least 2%, at least 2.5%, at least 3%, at least 4%, at least 5%, at least 6%, at least 7%, at least 8%, at least 9%, at least 10% prior to the administration of the one or more doses of one or more IL-5R binding molecules. In one embodiment, a subject has a % eosinophil in induced sputum of 0.5% prior to the administration of the one or more doses of one or more IL-5R binding molecules. In one embodiment, a subject has a % eosinophil in induced sputum of 1% prior to the administration of the one or more doses of one or more IL-5R binding molecules. In one embodiment, a subject has a % eosinophil in induced sputum of 1.5% prior to the administration of the one or more doses of one or more IL-5R binding molecules. In one embodiment, a subject has a % eosinophil in induced sputum of 2% prior to the administration of the one or more doses of one or more IL-5R binding molecules. In one embodiment, a subject has a % eosinophil in induced sputum of 2.5% prior to the administration of the one or more doses of one or more IL-5R binding molecules. In one embodiment, a subject has a % eosinophil in induced sputum of 3% prior to the administration of the one or more doses of one or more IL-5R binding molecules. In one embodiment, a subject has a % eosinophil in induced sputum of 4% prior to the administration of the one or more doses of one or more IL-5R binding molecules. In one embodiment, a subject has a % eosinophil in induced sputum of 5% prior to the administration of the one or more doses of one or more IL-5R binding molecules. In one embodiment, a subject has a % eosinophil in induced sputum of 6% prior to the administration of the one or more doses of one or more IL-5R binding molecules. In one embodiment, a subject has a % eosinophil in induced sputum of 7% prior to the administration of the one or more doses of one or more IL-5R binding molecules. In one embodiment, a subject has a % eosinophil in induced sputum of 8% prior to the administration of the one or more doses of one or more IL-5R binding molecules. In one embodiment, a subject has a % eosinophil in induced sputum of 9% prior to the administration of the one or more doses of one or more IL-5R binding molecules. In one embodiment, a subject has a % eosinophil in induced sputum of 10% prior to the administration of the one or more doses of one or more IL-5R binding molecules.

In one embodiment, a subject has a % eosinophil in induced sputum of between 0.1% and 5% following the administration of the one or more doses of one or more IL-5R binding molecules. In one embodiment, a subject has a % eosinophil in induced sputum between 0.1% and 3%, between 0.1% and 2%, between 0.1% and 1.5%, between 0.5% and 5%, between 0.5% and 3%, between 0.5% and 1%, between 1% and 5%, between 1% and 3%, between 2% and 5%, between 3% and 5%, between 2.5% and 5% following the administration of the one or more doses of one or more IL-5R binding molecules. In one embodiment, a subject has a % eosinophil in induced sputum of at most 1%, at most 2%, at most 3%, at most 4%, at most 5%, at most 6%, at most 7%, at most 8%, at most 9%, at most 10% following the administration of the one or more doses of one or more IL-5R binding molecules. In one embodiment, a subject has a % eosinophil in induced sputum of at most 1% following the administration of the one or more doses of one or more IL-5R binding molecules. In one embodiment, a subject has a % eosinophil in induced sputum of at most 2% following the administration of the one or more doses of one or more IL-5R binding molecules. In one embodiment, a subject has a % eosinophil in induced sputum of at most 3% following the administration of the one or more doses of one or more. IL-5R binding molecules. In one embodiment, a subject has a % eosinophil in induced sputum of at most 4% following the administration of the one or more doses of one or more IL-5R binding molecules. In one embodiment, a subject has a % eosinophil in induced sputum of at most 5% following the administration of the one or more doses of one or more IL-5R binding molecules. In one embodiment, a subject has a % eosinophil in induced sputum of at most 6% following the administration of the one or more doses of one or more IL-5R binding molecules. In one embodiment, a subject has a % eosinophil in induced sputum of at most 7% following the administration of the one or more doses of one or more IL-5R binding molecules. In one embodiment, a subject has a % eosinophil in induced sputum of at most 8% following the administration of the one or more doses of one or more IL-5R binding molecules. In one embodiment, a subject has a % eosinophil in induced sputum of at most 9% following the administration of the one or more doses of one or more IL-5R binding molecules. In one embodiment, a subject has a % eosinophil in induced sputum of at most 10% following the administration of the one or more doses of one or more IL-5R binding molecules.

In one embodiment, the % eosinophil in induced sputum of a subject is lower following the administration of one or more doses of one or more IL-5R binding molecules than prior to the administration of one or more doses of one or more IL-5R binding molecules, wherein the % eosinophil in induced sputum is never below 0%. In a specific embodiment, the % eosinophil in induced sputum is by at least 10% lower. In a specific embodiment, the % eosinophil in induced sputum is by at least 9% lower. In a specific embodiment, the % eosinophil in induced sputum is by at least 8% lower. In a specific embodiment, the % eosinophil in induced sputum is by at least 6% lower. In a specific embodiment, the % eosinophil in induced sputum is by at least 5% lower. In a specific embodiment, the % eosinophil in induced sputum is by at least 4% lower. In a specific embodiment, the % eosinophil in induced sputum is by at least 3% lower. In a specific embodiment, the % eosinophil in induced sputum is by at least 2% lower. In a specific embodiment, the % eosinophil in induced sputum is by at least 1% lower.

In one embodiment, a subject has no detectable eosinophil in induced sputum following the administration of the one or more doses of one or more IL-5R binding molecules. In a specific embodiment, the eosinophils in induced sputum remain undetectable for at least about 1 day, at least about 2 days, at least about 3 days, at least about 4 days, at least about 5 days, at least about 6 days, at least about 7 days, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 12 weeks, at least about 14 weeks, at least about 16 weeks, at least about 20 weeks, or at least about 25 weeks.

In one embodiment, the disease indicator or symptom is circulating basophil count. Circulating basophil count may be assessed using any methods known to one of skill in the art, for example, but not limited to histology, flow cytometry. Circulating basophil count may be measured by any one of the commercially available kits.

In one embodiment, a subject has a circulating basophil count of between 5 and 500 cells/microL prior to the administration of the one or more doses of one or more IL-5R binding molecules. In one embodiment, a subject has a circulating basophil count between 50 and 500 cells/microL, between 10 and 500 cells/microL, between 20 and 500 cells/microL, between 30 and 500 cells/microL, between 40 and 500 cells/microL, between 50 and 500 cells/microL, between 10 and 400 cells/microL, between 10 and 300 cells/microL, between 10 and 200 cells/microL, between 10 and 100 cells/microL, between 20 and 100 cells/microL, between 30 and 100 cells/microL, between 10 and 75 cells/microL prior to the administration of the one or more doses of one or more IL-5R binding molecules. In one embodiment, a subject has a circulating basophil count of at least 5 cells/microL, at least 10 cells/microL, at least 15 cells/microL, at least 20 cells/microL, at least 30 cells/microL, at least 50 cells/microL, at least 60 cells/microL, at least 100 cells/microL prior to the administration of the one or more doses of one or more IL-5R binding molecules. In one embodiment, a subject has a circulating basophil count of 5 cells/microL prior to the administration of the one or more doses of one or more IL-5R binding molecules. In one embodiment, a subject has a circulating basophil count of 10 cells/microL prior to the administration of the one or more doses of one or more IL-5R binding molecules. In one embodiment, a subject has a circulating basophil count of 15 cells/microL prior to the administration of the one or more doses of one or more IL-5R binding molecules. In one embodiment, a subject has a circulating basophil count of 20 cells/microL prior to the administration of the one or more doses of one or more IL-5R binding molecules. In one embodiment, a subject has a circulating basophil count of 30 cells/microL prior to the administration of the one or more doses of one or more IL-5R binding molecules. In one embodiment, a subject has a circulating basophil count of 50 cells/microL prior to the administration of the one or more doses of one or more IL-5R binding molecules. In one embodiment, a subject has a circulating basophil count of 60 cells/microL prior to the administration of the one or more doses of one or more IL-5R binding molecules. In one embodiment, a subject has a circulating basophil count of 100 cells/microL prior to the administration of the one or more doses of one or more IL-5R binding molecules.

In one embodiment, a subject has a circulating basophil count of between 1 and 100 cells/microL following the administration of the one or more doses of one or more IL-5R binding molecules. In one embodiment, a subject has a circulating basophil count between 1 and 100 cells/microL, between 1 and 50 cells/microL, between 1 and 30 cells/microL, between 1 and 20 cells/microL, between 1 and 10 cells/microL, between 5 and 100 cells/microL, between 5 and 50 cells/microL, between 5 and 20 cells/microL, between 5 and 10 cells/microL, between 10 and 30 cells/microL following the administration of the one or more doses of one or more IL-5R binding molecules. In one embodiment, a subject has a circulating basophil count of at most 1 cells/microL, at most 5 cells/microL, at most 10 cells/microL, at most 20 cells/microL, at most 30 cells/microL, at most 50 cells/microL, at most 100 cells/microL following the administration of the one or more doses of one or more IL-5R binding molecules. In one embodiment, a subject has a circulating basophil count of at most 1 cells/microL following the administration of the one or more doses of one or more IL-5R binding molecules. In one embodiment, a subject has a circulating basophil count of at most 5 cells/microL following the administration of the one or more doses of one or more IL-5R binding molecules. In one embodiment, a subject has a circulating basophil count of at most 10 cells/microL following the administration of the one or more doses of one or more IL-5R binding molecules. In one embodiment, a subject has a circulating basophil count of at most 20 cells/microL following the administration of the one or more doses of one or more IL-5R binding molecules. In one embodiment, a subject has a circulating basophil count of at most 30 cells/microL following the administration of the one or more doses of one or more IL-5R binding molecules. In one embodiment, a subject has a circulating basophil count of at most 40 cells/microL following the administration of the one or more doses of one or more IL-5R binding molecules. In one embodiment, a subject has a circulating basophil count of at most 50 cells/microL following the administration of the one or more doses of one or more. IL-5R binding molecules.

In one embodiment, the circulating basophil count of a subject is lower following the administration of one or more doses of one or more IL-5R binding molecules than prior to the administration of one or more doses of one or more IL-5R binding molecules, wherein the circulating basophil count is never below 0 cells/microL. In a specific embodiment, the circulating basophil count is at least 10 cells/microL lower. In a specific embodiment, the circulating basophil count is at least 20 cells/microL lower. In a specific embodiment, the circulating basophil count is at least 30 cells/microL lower. In a specific embodiment, the circulating basophil count is at least 50 cells/microL lower. In a specific embodiment, the circulating basophil count is at least 75 cells/microL lower. In a specific embodiment, the circulating basophil count is at least 100 cells/microL lower. In a specific embodiment, the circulating basophil count is at least 10% lower. In a specific embodiment, the circulating basophil count is at least 20% lower. In a specific embodiment, the circulating basophil count is at least 30% lower. In a specific embodiment, the circulating basophil count is at least 40% lower. In a specific embodiment, the circulating basophil count is at least 50% lower. In a specific embodiment, the circulating basophil count is at least 60% lower. In a specific embodiment, the circulating basophil count is at least 70% lower. In a specific embodiment, the circulating basophil count is at least 80% lower. In a specific embodiment, the circulating basophil count is at least 90% lower. In a specific embodiment, the circulating basophil count is at least 95% lower. In a specific embodiment, the circulating basophil count is at least 99% lower. In a specific embodiment, the circulating basophil count is 10% lower. In a specific embodiment, the circulating basophil count is 20% lower. In a specific embodiment, the circulating basophil count is 30% lower. In a specific embodiment, the circulating basophil count is 40% lower. In a specific embodiment, the circulating basophil count is 50% lower. In a specific embodiment, the circulating basophil count is 60% lower. In a specific embodiment, the circulating basophil count is 70% lower. In a specific embodiment, the circulating basophil count is 80% lower. In a specific embodiment, the circulating basophil count is 90% lower. In a specific embodiment, the circulating basophil count is 95% lower. In a specific embodiment, the circulating basophil count is 99% lower.

In one embodiment, a subject has no detectable circulating basophil count following the administration of the one or more doses of one or more IL-5R binding molecules. In a specific embodiment, the circulating basophil count level remains undetectable for at least about 1 day, at least about 2 days; at least about 3 days, at least about 4 days, at least about 5 days, at least about 6 days, at least about 7 days, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 12 weeks, at least about 14 weeks, at least about 16 weeks, at least about 20 weeks, or at least about 25 weeks.

SPECIFIC EMBODIMENTS

1. A method of reducing the numbers of eosinophils in a human subject comprising administration to said subject an IL-5R binding molecule that comprises (a) a region that specifically binds to the IL-5R and (b) an immunoglobulin Fc region.

2. The method of embodiment 1, wherein said IL-5R binding molecule is an antibody.

3. The method of embodiment 2, wherein said antibody is a monoclonal antibody.

4. The method of embodiment 3, wherein said antibody is a chimeric antibody.

5. The method of embodiment 3, wherein said antibody is a humanized antibody.

6. The method of embodiment 3, wherein said antibody is a human antibody.

7. The method of embodiment 1, wherein said region that specifically binds to the IL-5R comprises the amino acid sequence of IL-5, or fragments, substitutions, or derivatives thereof.

8. The method of embodiment 7, wherein said region that specifically binds to the IL-5R comprises a nonfunctional variant of IL-5.

9. The method of any of embodiments 1-8, wherein said IL-5R binding molecule specifically binds to the IL-5R ? chain.

10. The method of embodiment 1, wherein said immunoglobulin Fc region is altered in a manner that increases effector function.

11. The method of embodiment 1, wherein said immunoglobulin Fc region comprises reduced levels of fucose.

12. The method of embodiment 11, wherein said immunoglobulin Fc region comprises no fucose.

13. The method of embodiment 1; wherein said immunoglobulin Fc region comprises amino acid substitutions that yield increased effector function.

14. The method of embodiment 1, wherein said amino acid substitutions comprise the inclusion of the following amino acid sequences in the Fc region: 332E, 239D and 330L, as numbered by the EU index as set forth in Kabat.

15. The method of embodiment 1, wherein said reduction in eosinophils occurs in the peripheral blood circulation.

16. The method of embodiment 1, wherein the numbers of eosinophils are reduced to a level that is less than 50 eosinophils/mm3.

17. The method of embodiment 1, wherein the reduction of eosinophils takes place within the first 48 hours after administration.

18. The method of embodiment 1, wherein the reduction of eosinophils takes place within the first 24 hours after administration.

19. The method of embodiment 1, wherein the reduction of eosinophils is reversible.

20. The method of embodiment 1, wherein there is a post-administration reduction in absolute eosinophil count of at least about 25 eosinophils/mm3.

21. The method of embodiment 1, wherein there is a post-administration reduction in absolute eosinophil count of at least about 50 eosinophils/mm3.

22. The method of embodiment 1, wherein there is a post-administration reduction in absolute eosinophil count of at least about 75 eosinophils/mm3.

23. The method of embodiment 1, wherein there is a post-administration reduction in absolute eosinophil count of at least about 100 eosinophils/mm3.

24. The method of embodiment 1, wherein there is a post-administration reduction in absolute eosinophil count of at least about 125 eosinophils/mm3.

25. The method of embodiment 1, wherein there is a post-administration reduction in absolute eosinophil count of at least about 150 eosinophils/mm3.

26. The method of embodiment 1, wherein there is a post-administration reduction in absolute eosinophil count of at least about 175 eosinophils/mm3.

27. The method of embodiment 1, wherein there is a post-administration reduction in absolute eosinophil count of at least about 200 eosinophils/mm3.

28. The method of embodiment 1, wherein there is a post-administration reduction in absolute eosinophil count of at least about 225 eosinophils/mm3.

29. The method of embodiment 1, wherein there is a post-administration reduction in absolute eosinophil count of at least about 250 eosinophils/mm3.

30. The method of embodiment 1, wherein there is a post-administration reduction in absolute eosinophil count of at least about 275 eosinophils/mm3.

31. The method of embodiment 1, wherein there is a post-administration reduction in absolute eosinophil count of at least about 300 eosinophils/mm3.

32. The method of embodiment 1, wherein there is a post-administration reduction in absolute eosinophil count of at least about 325 eosinophils/mm3.

33. The method of embodiment 1, wherein there is a post-administration reduction in absolute eosinophil count of at least about 350 eosinophils/mm3.

34. The method of embodiment 1, wherein there is a post-administration reduction in absolute eosinophil count of at least about 375 eosinophils/mm3.

35. The method of embodiment 1, wherein there is a post-administration reduction in absolute eosinophil count of at least about 400 eosinophils/mm3.

36. The method of embodiment 1, wherein there is a post-administration reduction in absolute eosinophil count of at least about 425 eosinophils/mm3.

37. The method of embodiment 1, wherein there is a post-administration reduction in absolute eosinophil count of at least about 450 eosinophils/mm3.

38. The method of embodiment 1, wherein there is a post-administration reduction in absolute eosinophil count of at least about 475 eosinophils/mm3.

39. The method of embodiment 1, wherein there is a post-administration reduction in absolute eosinophil count of at least about 500 eosinophils/mm3.

40. The method of embodiment 1, wherein there is a post-administration reduction in absolute eosinophil count of between and including about 50 to about 500 eosinophils/mm3.

41. The method of embodiment 1, wherein there is a post-administration reduction in absolute eosinophil count of between and including about 75 to about 250 eosinophils/mm3.

42. The method of embodiment 1, wherein there is a post-administration reduction in absolute eosinophil count of between and including about 100 to about 200 eosinophils/mm3.

43. The method of embodiment 1, wherein there is a post-administration reduction in absolute eosinophil count of between and including about 50 to about 250 eosinophils/mm3.

44. The method of embodiment 1, wherein there is a post-administration reduction in absolute eosinophil count of between and including about 50 to about 200 eosinophils/mm3.

45. The method of embodiment 1, wherein there is a post-administration reduction in absolute eosinophil count of between and including about 50 to about 150 eosinophils/mm3.

46. The method of embodiment 1, wherein the absolute eosinophil count post-administration is less than about 100 eosinophils/mm3.

47. The method of embodiment 1, wherein the absolute eosinophil count post-administration is less than about 75 eosinophils/mm3.

48. The method of embodiment 1, wherein the absolute eosinophil count post-administration is less than about 50 eosinophils/mm3.

49. The method of embodiment 1, wherein the absolute eosinophil count post-administration is less than about 25 eosinophils/mm3.

50. The method of embodiment 1, wherein said subject's pre-administration absolute eosinophil count is between about 50 and about 500 eosinophils/mm3.

51. The method of embodiment 1, wherein said subject's pre-administration absolute eosinophil count is between about 75 and about 475 eosinophils/mm3.

52. The method of embodiment 1, wherein said subject's pre-administration absolute eosinophil count is between about 75 and about 200 eosinophils/mm3.

53. The method of embodiment 1, wherein said subject's pre-administration absolute eosinophil count is between about 100 and about 200 eosinophils/mm3.

54. The method of embodiment 1, wherein said subject's pre-administration absolute eosinophil count is about 25 eosinophils/mm3.

55. The method of embodiment 1, wherein said subject's pre-administration absolute eosinophil count is about 50 eosinophils/mm3.

56. The method of embodiment 1, wherein said subject's pre-administration absolute eosinophil count is about 75 eosinophils/mm3.

57. The method of embodiment 1, wherein said subject's pre-administration absolute eosinophil count is about 100 eosinophils/mm3.

58. The method of embodiment 1, wherein said subject's pre-administration absolute eosinophil count is about 125 eosinophils/mm3.

59. The method of embodiment 1, wherein said subject's pre-administration absolute eosinophil count is about 150 eosinophils/mm3.

60. The method of embodiment 1, wherein said subject's pre-administration absolute eosinophil count is about 175 eosinophils/mm3.

61. The method of embodiment 1, wherein said subject's pre-administration absolute eosinophil count is about 200 eosinophils/mm3.

62. The method of embodiment 1, wherein said subject's pre-administration absolute eosinophil count is about 225 eosinophils/mm3.

63. The method of embodiment 1, wherein said subject's pre-administration absolute eosinophil count is about 250 eosinophils/mm3.

64. The method of embodiment 1, wherein said subject's pre-administration absolute eosinophil count is about 275 eosinophils/mm3.

65. The method of embodiment 1, wherein said subject's pre-administration absolute eosinophil count is about 300 eosinophils/mm3.

66. The method of embodiment 1, wherein said subject's pre-administration absolute eosinophil count is about 325 eosinophils/mm3.

67. The method of embodiment 1, wherein said subject's pre-administration absolute eosinophil count is about 350 eosinophils/mm3.

68. The method of embodiment 1, wherein said subject's pre-administration absolute eosinophil count is about 375 eosinophils/mm3.

69. The method of embodiment 1, wherein said subject's pre-administration absolute eosinophil count is about 400 eosinophils/mm3.

70. The method of embodiment 1, wherein said subject's pre-administration absolute eosinophil count is about 425 eosinophils/mm3.

71. The method of embodiment 1, wherein said subject's pre-administration absolute eosinophil count is about 450 eosinophils/mm3.

72. The method of embodiment 1, wherein said subject's pre-administration absolute eosinophil count is about 475 eosinophils/mm3.

73. The method of embodiment 1, wherein said subject's pre-administration absolute eosinophil count is about 500 eosinophils/mm3.

74. The method of any of embodiments 1-73, wherein said subject's post-administration absolute basophil count is reduced by at least about 5 basophils/mm3.

75. The method of any of embodiments 1-73, wherein said subject's post-administration absolute basophil count is reduced by at least about 10 basophils/mm3.

76. The method of any of embodiments 1-73, wherein said subject's post-administration absolute basophil count is reduced by at least about 15 basophils/mm3.

77. The method of any of embodiments 1-73, wherein said subject's post-administration absolute basophil count is reduced by at least about 20 basophils/mm3.

78. The method of any of embodiments 1-73, wherein said subject's post-administration absolute basophil count is reduced by at least about 25 basophils/mm3.

79. The method of any of embodiments 1-73, wherein said subject's post-administration absolute basophil count is reduced by at least about 30 basophils/mm3.

80. The method of any of embodiments 1-73, wherein said subject's post-administration absolute basophil count is reduced by at least about 35 basophils/mm3.

81. The method of any of embodiments 1-73, wherein said subject's post-administration absolute basophil count is reduced by at least about 40 basophils/mm3.

82. The method of any of embodiments 1-73, wherein said subject's post-administration absolute basophil count is reduced by at least about 45 basophils/mm3.

83. The method of any of embodiments 1-73, wherein said subject's post-administration absolute basophil count is reduced by at least about 50 basophils/mm3.

84. The method of any of embodiments 1-73, wherein said subject's post-administration absolute basophil count is reduced by at least about 55 basophils/mm3.

85. The method of any of embodiments 1-73, wherein said subject's post-administration absolute basophil count is reduced by at least about 60 basophils/mm3.

86. The method of any of embodiments 1-73, wherein said subject's post-administration absolute basophil count is reduced by at least about 65 basophils/mm3.

87. The method of any of embodiments 1-73, wherein said subject's post-administration absolute basophil count is reduced by at least about 70 basophils/mm3.

88. The method of any of embodiments 1-73, wherein said subject's post-administration absolute basophil count is between 0 and about 10 basophils/mm3.

89. The method of any of embodiments 1-73, wherein said subject's post-administration absolute basophil count is about 2 basophils/mm3.

90. The method of any of embodiments 1-73, wherein said subject's post-administration absolute basophil count is about 5 basophils/mm3.

91. The method of any of embodiments 1-73, wherein said subject's post-administration absolute basophil count is about 7 basophils/mm3.

92. The method of any of embodiments 1-73, wherein said subject's post-administration absolute basophil count is about 9 basophils/mm3.

93. The method of any of embodiments 1-73, wherein the basophil reduction occurs within 48 hours post-administration.

94. The method of any of embodiments 1-73, wherein the basophil reduction occurs within 24 hours post-administration.

95. The method of any of embodiments 1-94, wherein said IL-5R binding molecule is administered to said subject at a dose ranging from between about 0.001 to about 100 mg/kg.

96. The method of embodiment 95, wherein said dose is about 0.03 mg/kg.

97. The method of embodiment 95, wherein said dose is 0.03 mg/kg.

98. The method of any of embodiments 1-97, wherein said IL-5R binding molecule is administered parenterally.

99. The method of embodiment 98, wherein said IL-5R binding molecule is administered intravenously.

100. The method of any of embodiments 1-99, with the proviso that the IL-5R binding molecule is not MEDI-563.

101. The method of any of embodiments 1-100, wherein said reduction in eosinophils leads to a reduction in asthma symptoms.

102. The method of any of embodiments 1-100, wherein said reduction in eosinophils leads to a reduction in COPD symptoms.

EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

Example 1

MEDI-563, an Anti-Interleukin-5-Receptor Antibody, is Well Tolerated and Induces Reversible Blood Eosinopenia in Mild Asthmatics in a Phase I Trial Background:

Eosinophils are believed to play a key role in the pathogenesis of asthma. Interleukin-5 (IL-5) is a major cytokine in eosinophil biology, and expression of its receptor (IL-5R) is largely restricted to eosinophils, basophils, and mast cells. The suboptimal efficacy of IL-5-targeted therapies in asthma has been attributed to an incomplete depletion of eosinophils in lung tissue. Complete lung eosinophil depletion should provide additional insight into the role of these cells in asthma and could represent a novel therapeutic strategy.

Objectives:

To assess the safety and biological activity of MEDI-563 (previously known as BIW-8405), a humanized afucosylated IgG1 anti-IL-5R alpha chain monoclonal antibody. MEDI- 563 was developed by BioWa, Inc. through proprietary Potelligent® technology that significantly enhances antibody-dependent cellular cytotoxicity. MEDI-563 neutralizes IL-5 activity and depletes tissue eosinophils in pre-clinical models with an acceptable toxicology profile.

Methods:

Six subjects with mild asthma and absence of corticosteroid therapy were enrolled in the first cohort of study BIW-8405-001, an open-label first-in-human study with MEDI-563. The patients received a single intravenous dose of 0.03 mg/kg MEDI-563 and were followed for 84 days.

Results:

MEDI-563 was well tolerated, and no serious adverse events were reported. All adverse events (AEs) were mild, and the most frequently reported AE was fatigue on the dosing day post administration (3/6 subjects). Circulating eosinophils decreased below detection limits within 24-48 hours of dosing in all 6 subjects (will include mean value prior to dosing). This effect lasted for 8-12 weeks, and eosinophils became detectable in some subjects at Day 58 post dosing and reached ≥70% of baseline levels by Day 84 post dosing in all subjects analyzed. Circulating basophils followed a similar trend. Possibly linked to the expected mechanism of action of MEDI-563, neutrophil levels experienced a slight and transient decrease within 72 hours post dosing, reaching mild neutropenia levels in 2/6 subjects that resolved within 3 days. MEDI-563 administration was associated with immediate (within 6 hrs), modest (<10× baseline) and transient (<1 week duration) increases in serum C-reactive protein (2/6 subjects) and IL-6 (2/3).

Conclusions:

A single 0.03 mg/kg IV dose of MEDI-563 induces a robust blood eosinopenia, with an acceptable safety profile to date.

Example 2

Antibody Dependent Cell-Mediated Cytotoxicity

Figure 9A:
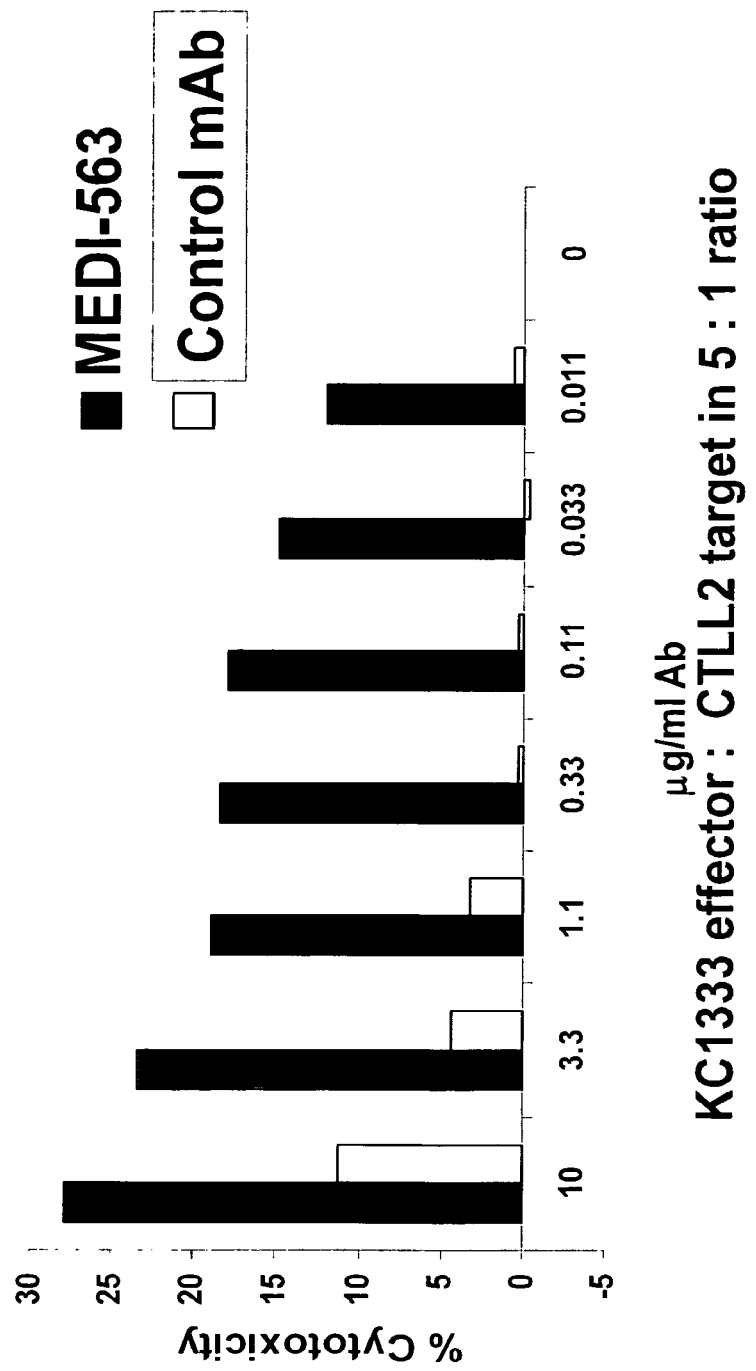
FIG. 9. In vitro cytotoxicity assay: MEDI-563 was assayed in an in vitro cytoxicity assay compared to a control antibody that does not bind IL-5R (A) and also to the additional control of fucosylated MEDI-563 (B). KC1333 effector cells were used in a 5:1 ratio against CTLL2 target cells. Cytotoxicity was measured at 4 hours. The Y axis measures percent cytotoxicity and the X axis is the concentration of antibody.
Figure 9B:
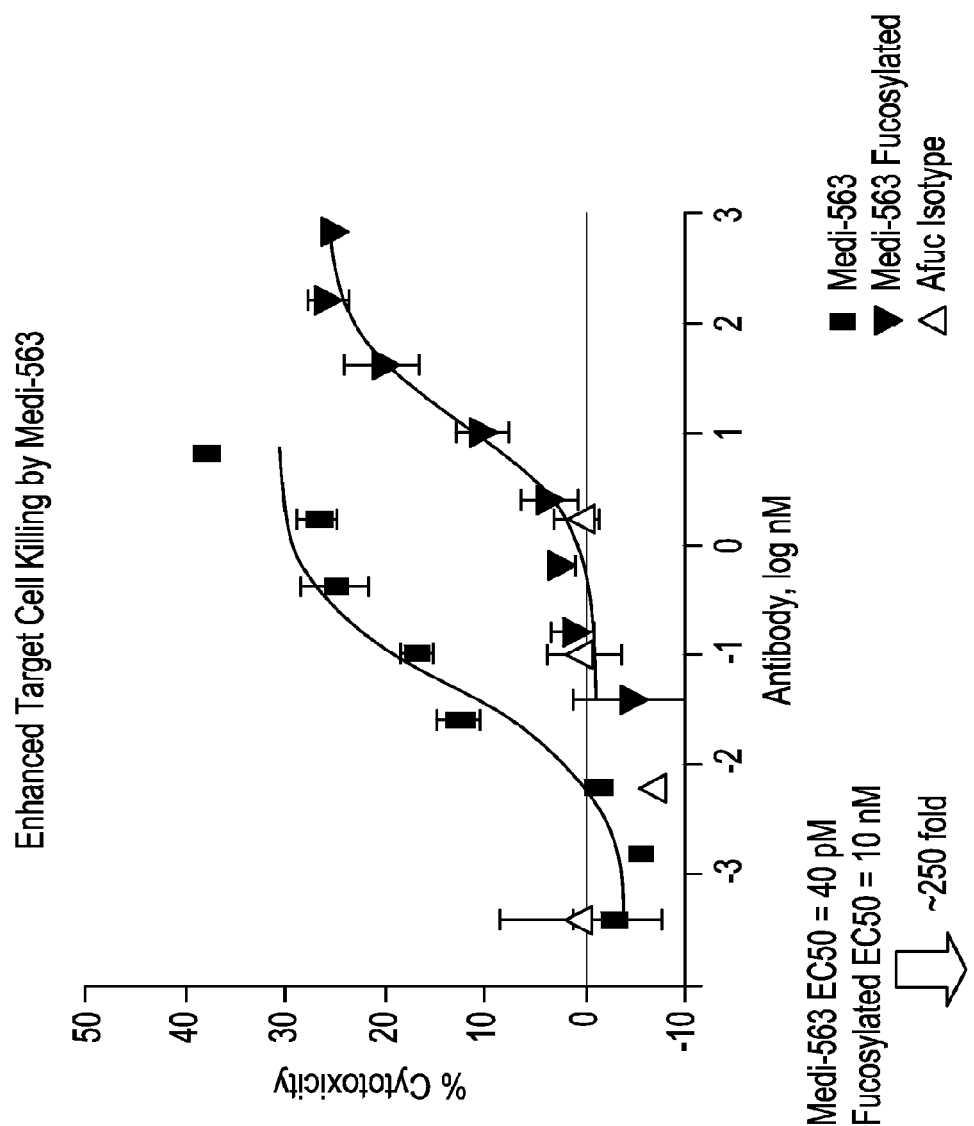

KC1333 effector cells (human NK cell overexpressing human FcgRIIIa and FceRIg) were co-incubated for 4 hours with target CTLL-2 cell line (mouse lymphoma genetically modified to overexpress human IL-5Ra) at a ratio of 5 effectors:1 target, in the presence of MEDI-563 or control antibody. Antibody mediated cytotoxicity was assessed using a Calcein AM cell viability assay. Results are summarized in FIG. 9A. Using a similar methodology, a further control (fucosylated MEDI-563) was analyzed. Results are summarized in FIG. 9B.

Example 3

Surface Plasmon Resonance Evaluation of Equilibrium Binding of MEDI-563 to IL-5R Carrier-free, soluble human IL-5Ra extracellular domain was obtained from a commercial source (R+D Systems). The recombinant huIL-5Ra was directly immobilized to a sensor chip through amine linkages using a standard protocol. The interaction of MEDI-563 with immobilized huIL-5Ra over time was evaluated by the change in refractive index, from which $k_{on}$, $k_{off}$, and $K_D$ values were calculated using standard techniques. Results are summarized in FIG. 10.

Example 4

Surface Plasmon Resonance Evaluation of Equilibrium Binding of MEDI-563 to FcγRs MEDI-563 was directly immobilized to a sensor chip through amine linkages using a standard protocol. The interactions of soluble human FcγRs (MedImmune) with immobilized MEDI-563 over time were evaluated by change in refractive index, from which $k_{on}$, $k_{off}$, and $K_D$ values were calculated using standard techniques. Results are summarized in FIG. 1I.

Example 5

IL-5Rα Immunohistochemistry

Figure 12:
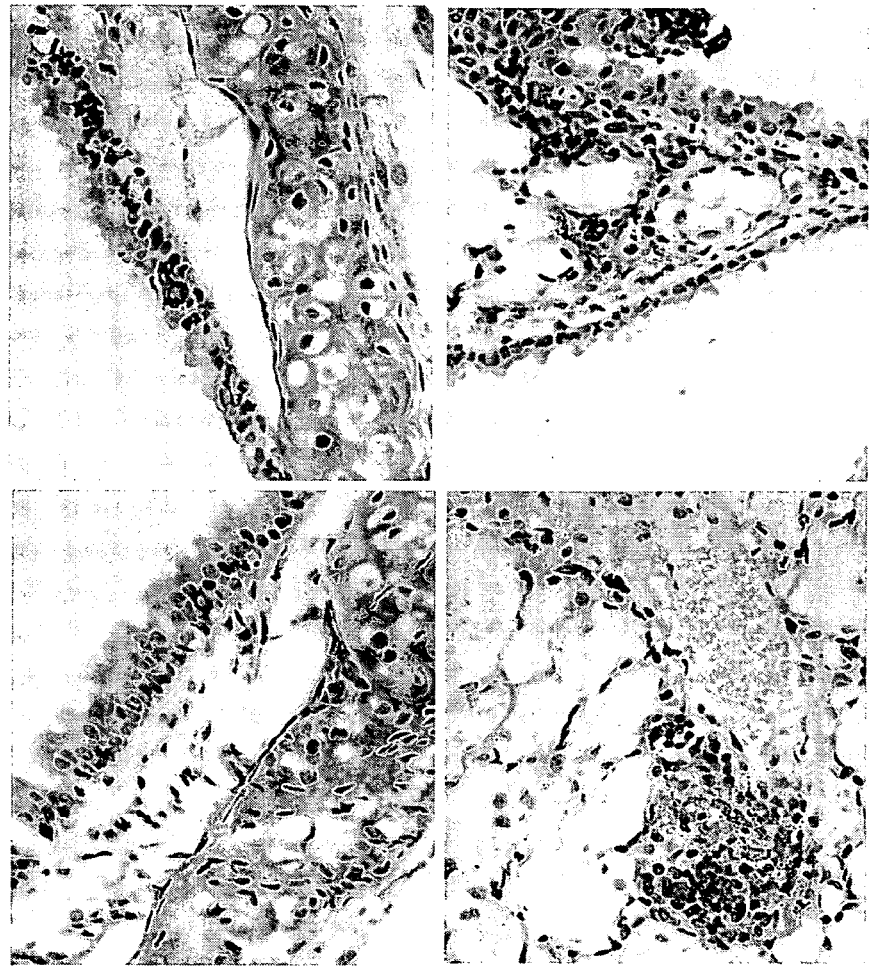
FIG. 12. IL-5Rα expression in the IL-9tg mouse lung was analyzed via immunohistochemistry and is visualized in this figure.
Figure 13:
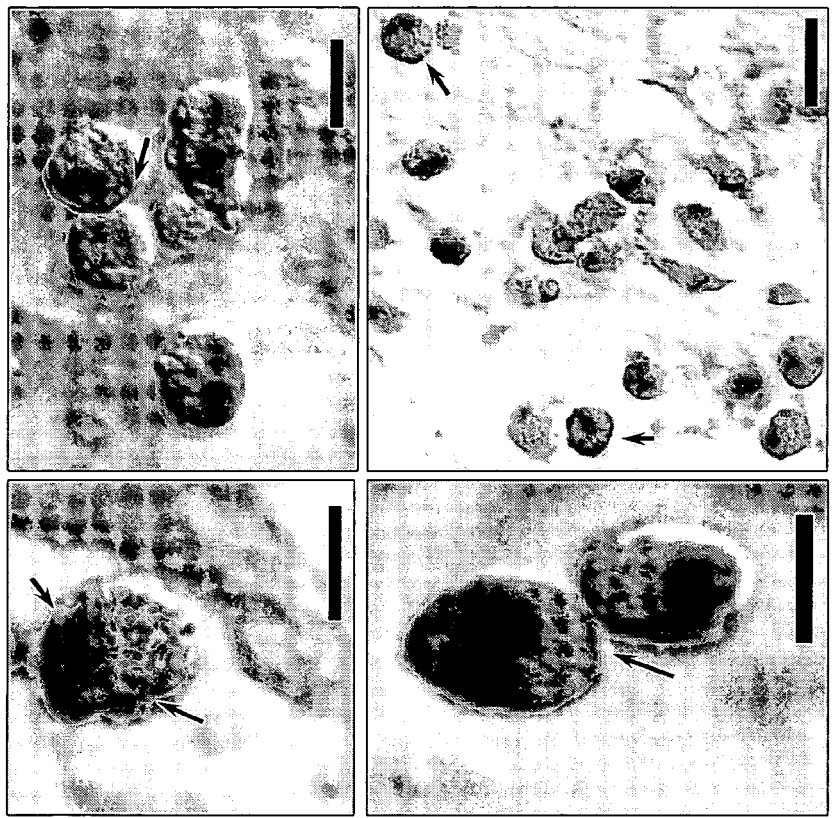
FIG. 13. IL-5Rα expression in nasal polyps was analyzed via immunohistochemistry using MEDI-563 and is visualized in this figure. MEDI-563 stains all eosinophils in nasal polyps.
Figure 14:
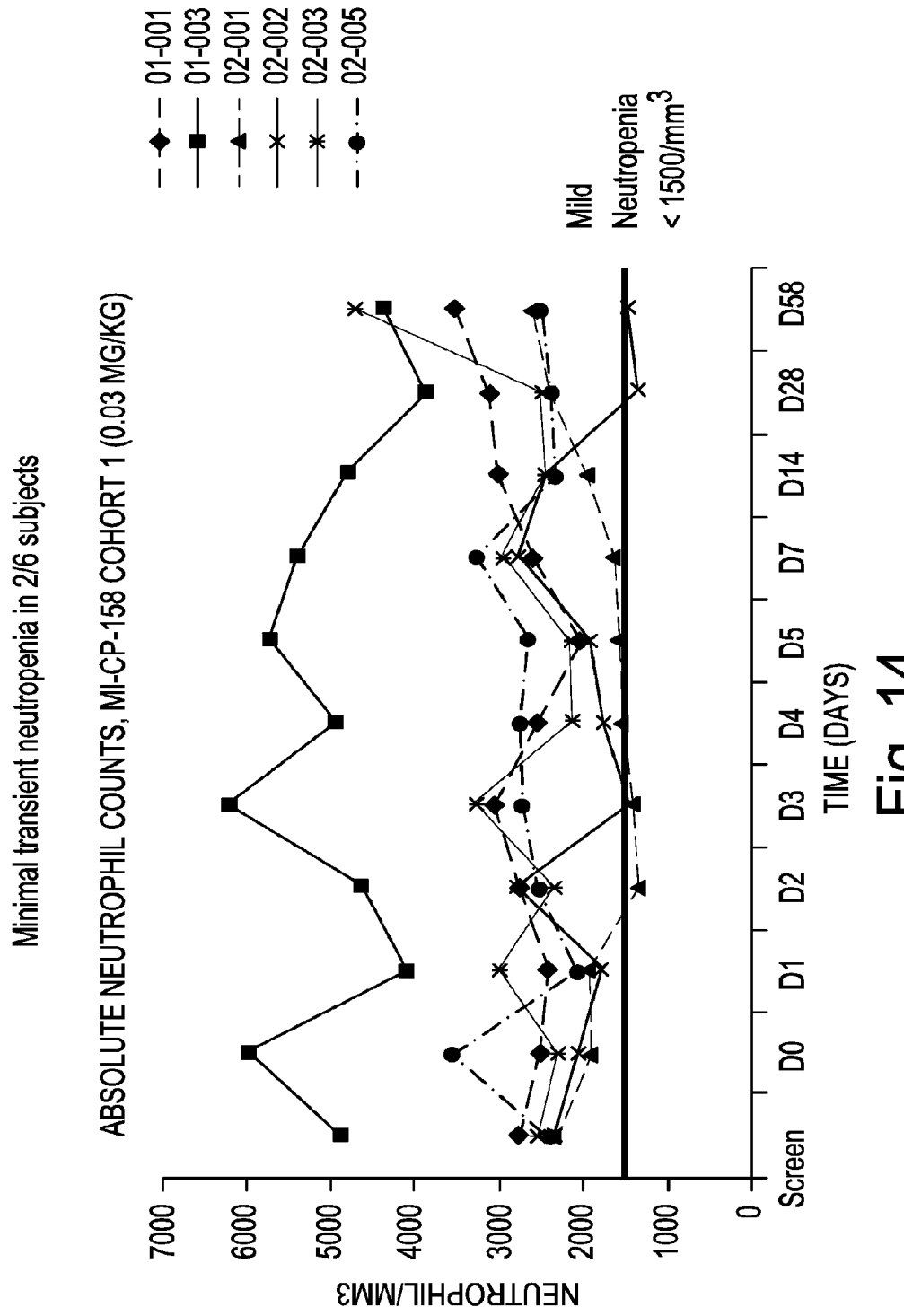
FIG. 14. Minimal Transient Neutropenia in Subjects: absolute neutrophil counts were taken for subjects in cohort 1 and are summarized in this figure. The Y-axis summarizes neutrophil counts (neutrophils/mm$^3$) and the X-axis summarizes time in days.

Resected nasal polyp tissue was fixed in formaldehyde for 24 hours and embedded in paraffin. Consecutive sections were stained for human IL-5Ra, IL-9R, CCR3, and c-kit using commercially available IL-5R directed polyclonal antibodies (R+D Systems, Santa Cruz Biotechnology) using standard techniques. Lung tissue from IL-9 transgenic mice or wild type strain matched FVB control mice were fixed in formaldehyde for 24 hours and embedded in paraffin. Sections were analyzed for IL-9R (pAb, Santa Cruz Biotechnology) and IL-5R (pAb, R+D Systems) expression using standard immunohistochemistry techniques. Results are summarized in FIGS. 12 and 13.

Example 6

Medi-563 Binds to Eosinophils in Whole Blood of Healthy Donors

Figure 15:
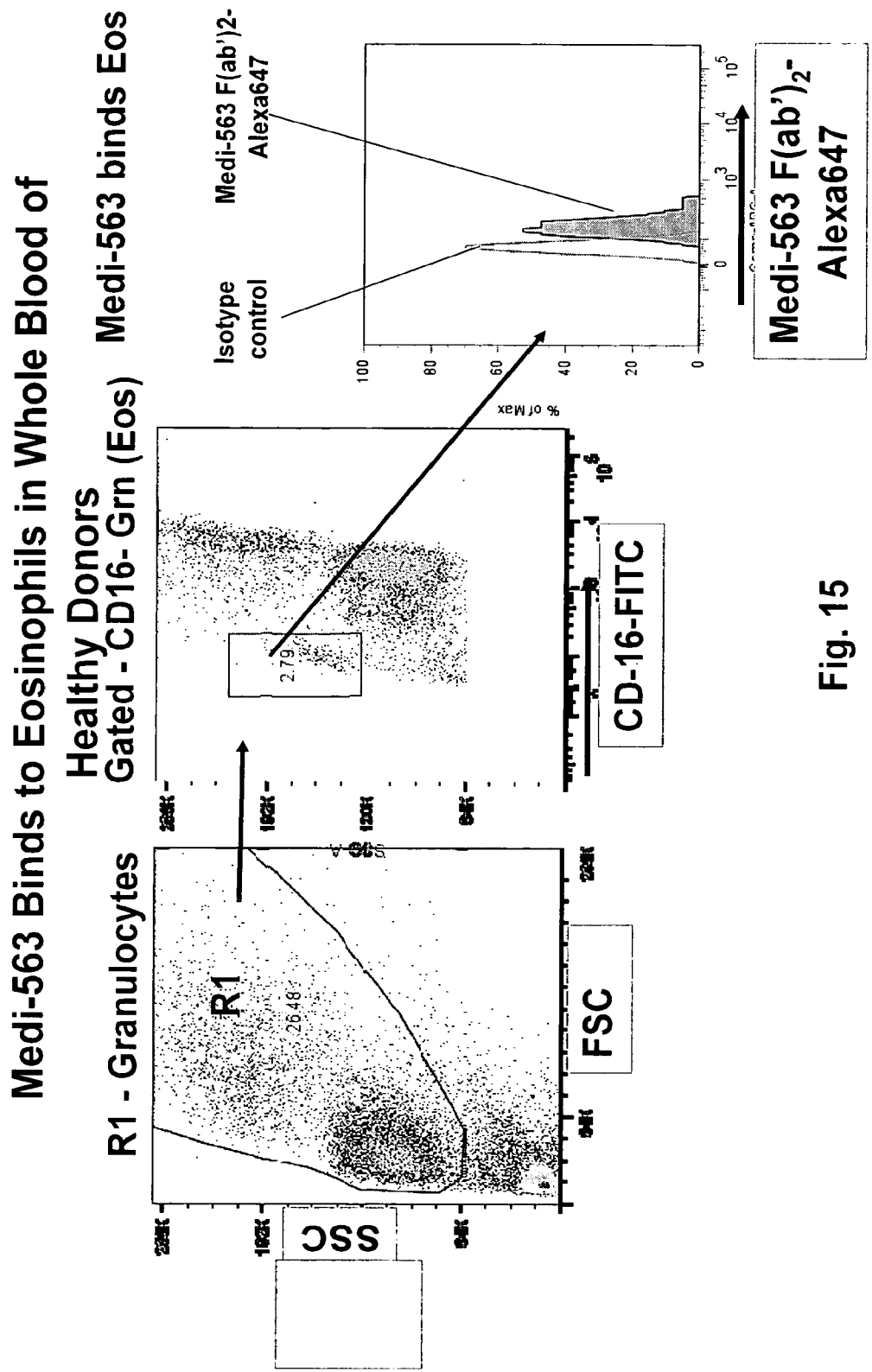
FIG. 15. MEDI-563 Binds to Eosinophils in Whole Blood of Healthy Donors: flow cytometry analysis was performed on whole blood samples as described in Example 6 herein. The three panels of data, particularly the third panel entitled "MEDI-563 Binds Eos," demonstrates by FACS that MEDI-563 binds to eosinophils.

Granulocytes were isolated from human whole blood of normal donors by density gradient centrifugation. Directly labeled primary antibody reagents were used for the analysis of CD16 (FITC fluorochrome) and MEDI-563 F(Ab)'2 (Alexa-647 fluorochrome) expression. A cocktail of CD16-FITC plus MEDI-563-Alexa647, or CD16-FITC plus an Alexa647-labeled isotype control antibody, were added to the granulocyte preparation at 1 microgram per 10^6 cells. After incubation for 45 minutes on ice, cells were washed three times in cold saline, and cell surface antibody binding was assessed by flow cytometry. Eosinophils, which are negative for CD16, were analyzed. The binding of MEDI-563 versus the isotype control antibody in CD16-negative granulocyte population is expressed. Results are summarized in FIG. 15.

Example 7

Mouse Leukocyte IL-5Rα Staining by Flow Cytometry

Figure 16A:
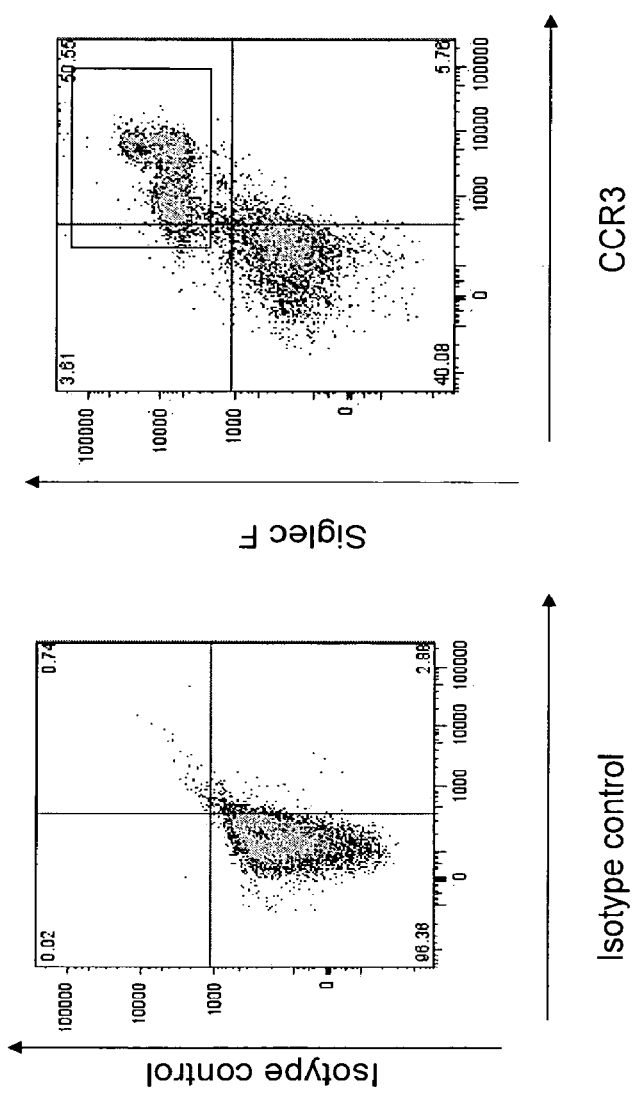
FIG. 16A summarizes FACS analysis of SiglecF+CCR3+ eosinophils.
Figure 16B:
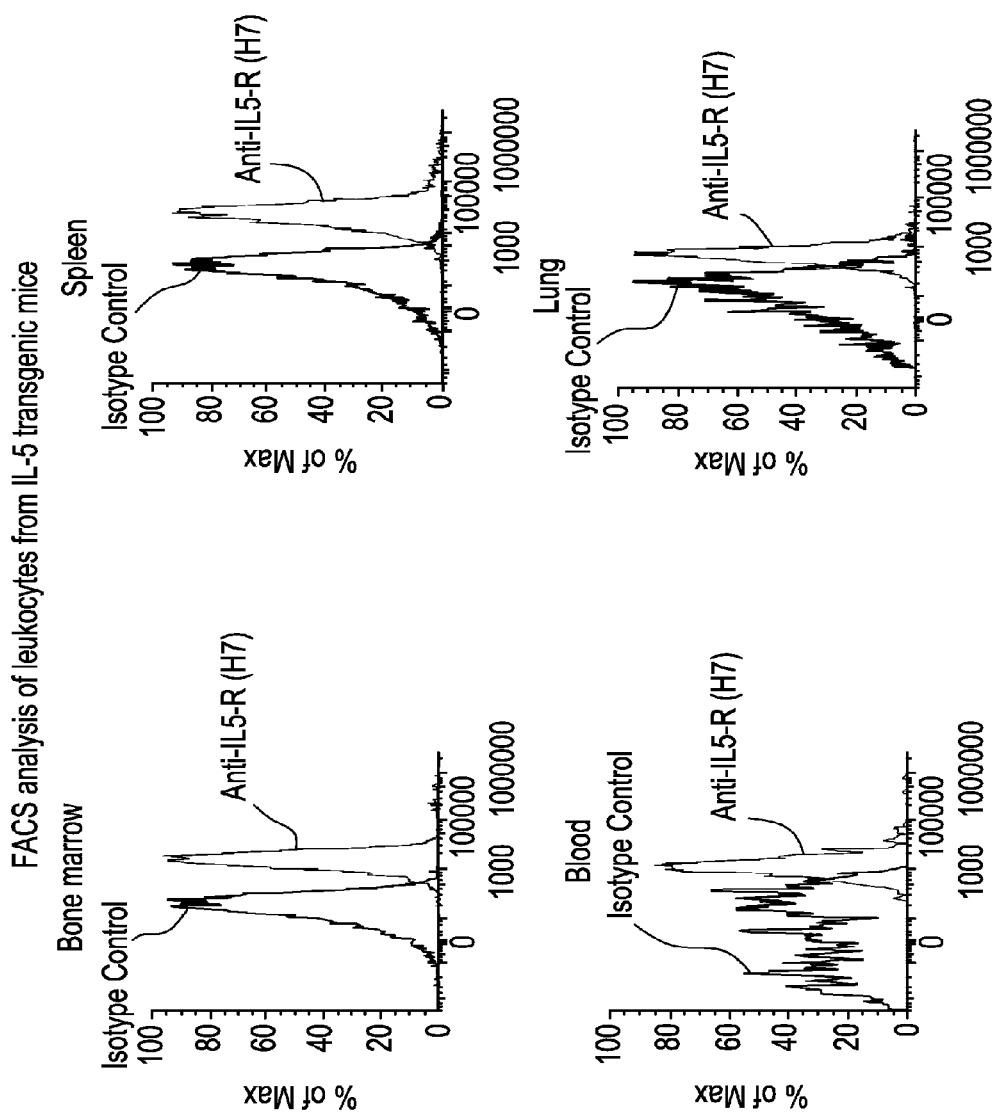
FIG. 16B demonstrates that all eosinophils (SiglecF+CCR3+) in the bone marrow, spleen, blood and lung express IL-5Rα+ using anti-IL-5Rα mAb H7.

Leukocytes were isolated from blood, bone marrow, lungs and spleen of IL-5 transgenic mice. Cell suspensions were stained in PBS containing 1% FCS. To reduce nonspecific binding, cells were incubated with Fc Block (BD Biosciences) for 15 min before staining. The antibodies used were anti-mouse CCR3 (R&D systems), anti-mouse Siglec F (BD Biosciences) and anti-mouse IL-5R(H7). Cells were stained for 30 min on ice, washed twice, and fixed in cytofix buffer (BD Biosciences). Flow cytometric analysis was performed using a LSRII (Becton Dickinson) with FACS Diva software (Becton Dickinson). Results were analyzed using FlowJo Software (TreeStar Inc.). Results are summarized in FIGS. 16A and 16B.

Example 8

Medi-563 Depletes IL-5Ra Positive Mononuclear Cells from Bone Marrow

Figure 17A:
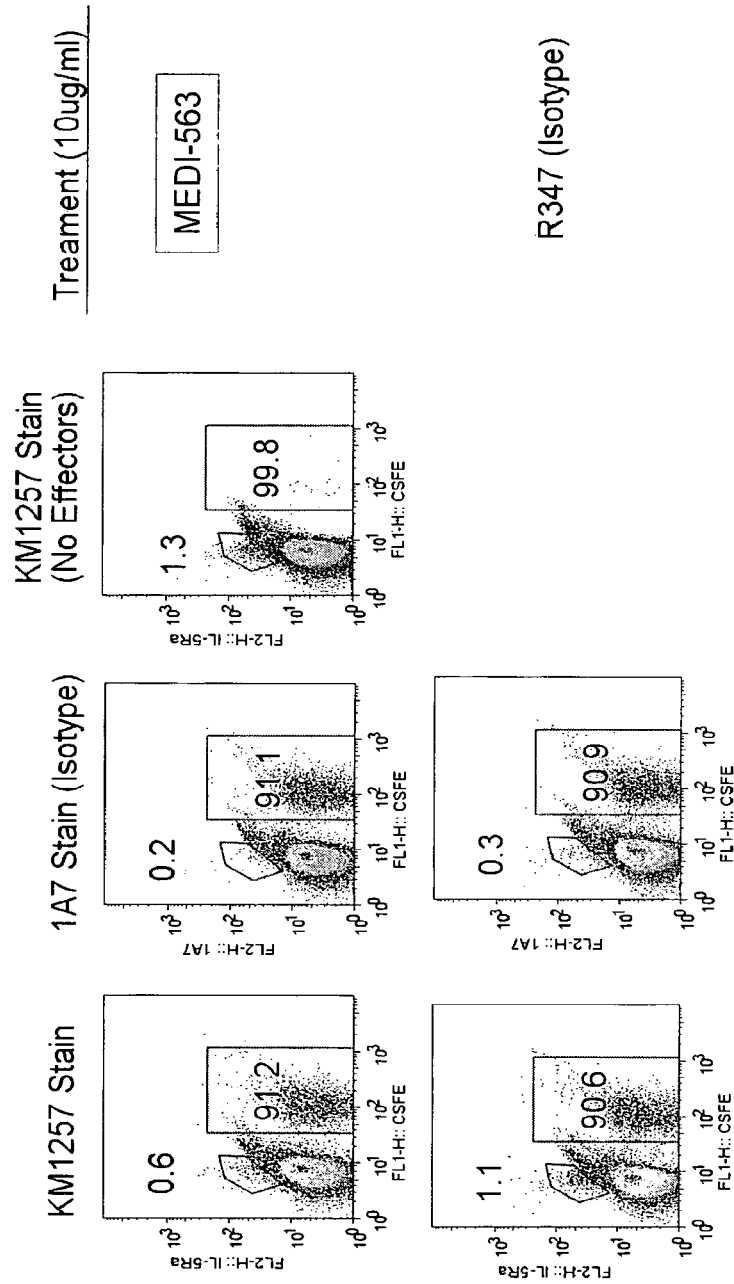
FIG. 17. MEDI-563 depletes IL-5Rα positive mononuclear cells from bone marrow in an in vitro ADCC assay. Isolated non-adherent bone marrow mononuclear cells were exposed to MEDI-563, or isotype control antibody (R347), in the presence of CFSE stained effector cells. IL-5Rα positive cells were visualized by KM1257 antibody/PE conjugated goat anti-Mu IgG. Control staining of samples was done using the 1A7 isotype control antibody/PE conjugated goat anti-Mu IgG. Staining profile of the sample cell populations following MEDI-563 or R347 mediated depletion is displayed as KM1257/PE vs. CFSE or 1A7/PE vs. CFSE dot plots. A comparison of the KM1257/PE vs. CFSE dot plots obtained for MEDI-563 and R347 treated samples reveals that MEDI-563 mediated ADCC depletes substantially all IL-5Rα positive cells from the sample.
Figure 17B:
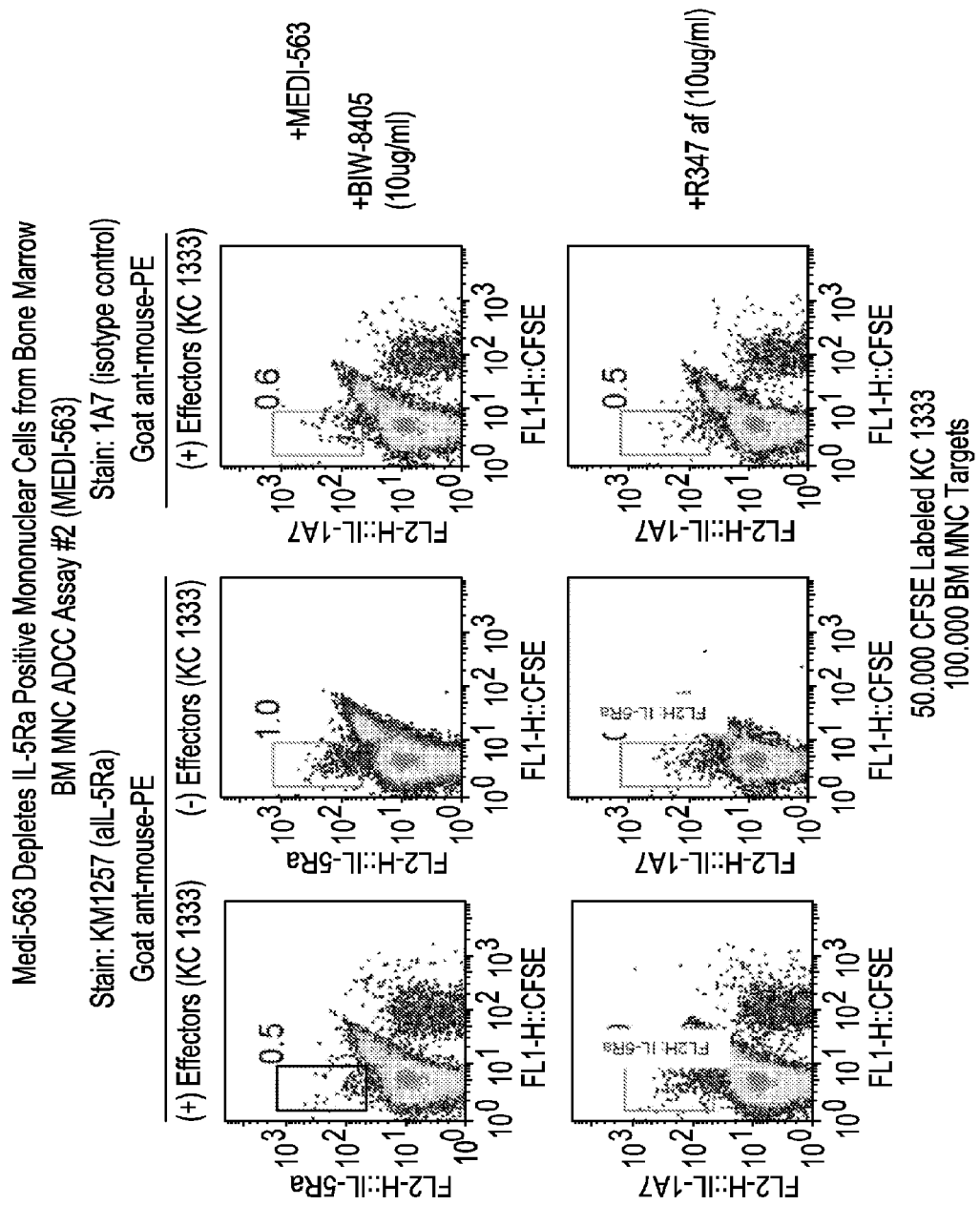

Frozen bone marrow mononuclear cells (BM MNC; Lonza) were thawed, washed, plated, and incubated for 2 hrs at 37° C. Non-adherent bone marrow mononuclear cells (NA BM MNC) were collected from the plates following incubation. ADCC assay was performed by coincubating for 18 hrs 100,000 NA BM MNC and 50,000 KC1333 effector cells per well in 200 ul 10% FBS/RPMI 1640 in 96 well TC plate in the presence of 10 ug/ml Medi-563 antibody. Negative control reactions were performed using the R347 aFuc isotype control antibody of irrelevant specificity. The KC1333 effector cells used in the ADCC assay were painted with CFDA SE. Following the 18 hr incubation, cells from each reaction were washed three times with warm medium and immunostained for flow cytometry. IL-5Ra positive cells were detected by KM1257 primary antibody/PE conjugated goat anti-Mu IgG Fcg specific secondary antibody staining. Control staining of samples was done with the 1A7 isotype matched control primary antibody in combination with the PE conjugated goat anti-Mu IgG Fcg specific secondary antibody. Immunostaining and flow cytometry was performed using standard protocols. The number of IL-5Ra positive cells remaining in a sample following ADCC was ascertained by counting the number of KM1257 positive cells in a lymphocyte gate. The immunostaining and flow cytometry procedures were calibrated using a CTLL-2 cell line expressing a human IL-5Ra transgene. MEDI-563 mediated ADCC depleted substantially all IL-5Ra positive cells from the NA BM MNC samples. Results are summarized in FIGS. 17A and 17B.

Example 9

MEDI-563 Mediated Depletion of Peripheral Blood Eosinophils

Figure 18A:
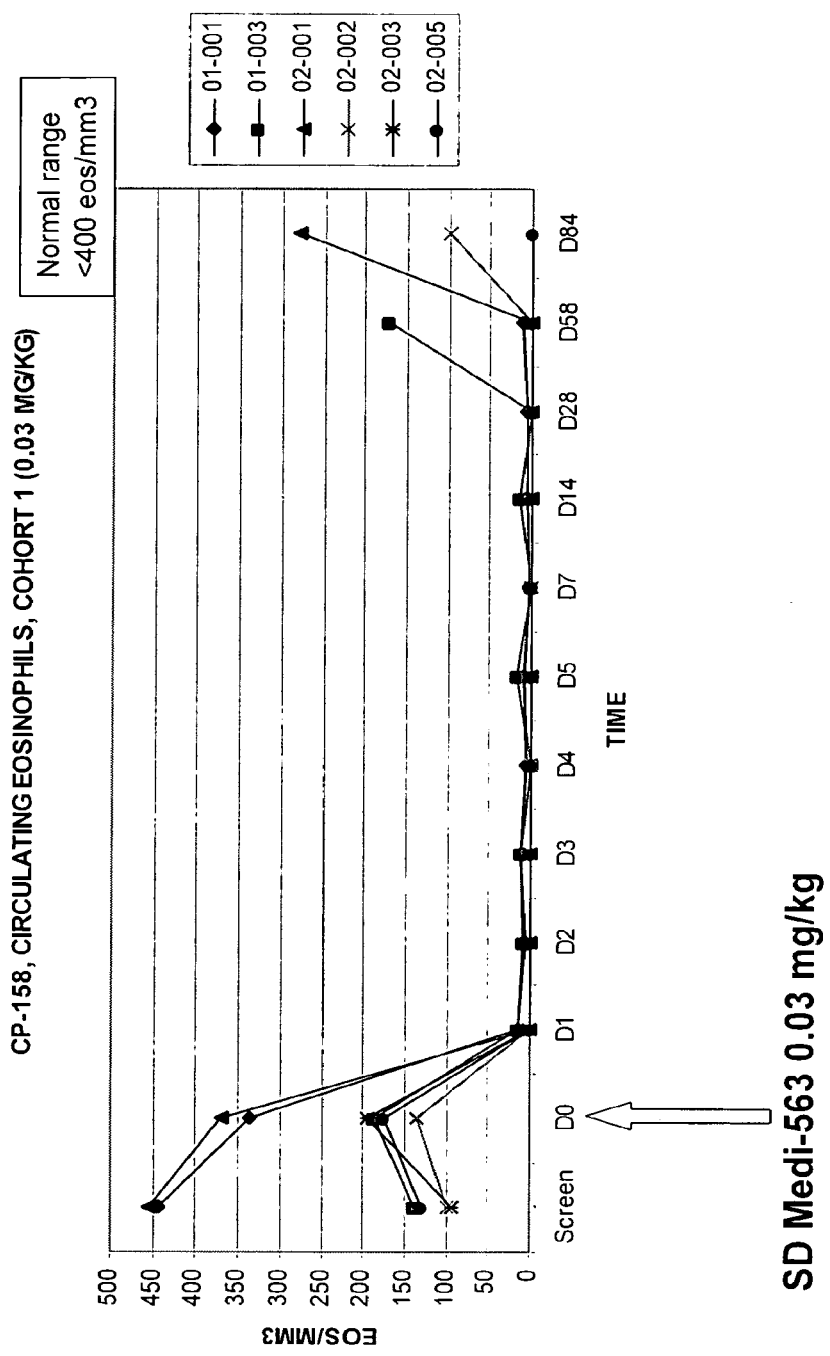
FIG. 18. MEDI-563 reversibly depletes peripheral blood eosinophils in mild asthmatics. Six volunteers with mild atopic asthma received a single IV dose of (A) 0.03 mg/kg or (B) 0.1 mg/kg MEDI-563. Peripheral blood eosinophils were enumerated by flow cytometry at screening, on day 0 prior to dosing, and at regular intervals up to day 84 and at follow-up. The y-axis summarizes eosinophil counts (eosinophils/mm3) and x-axis summarizes time (in days). Rapid reduction of eosinophils in the periphery was observed by 24 hours post-administration. The MEDI-563 induced eosinopenia was reversible.
Figure 18B:
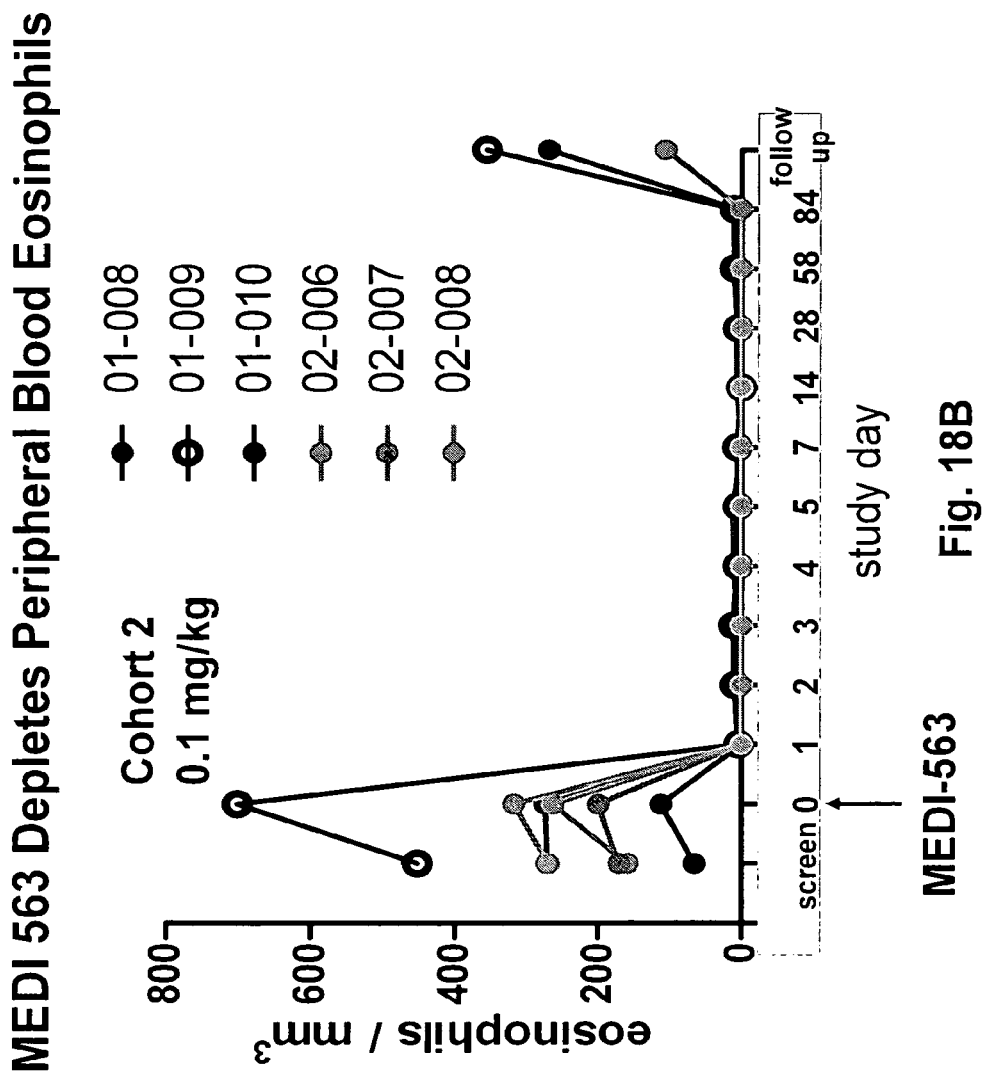

Two cohorts of six subjects with mild asthma were enrolled in an open-label study of MEDI-563. The subjects of cohort 1 and 2 received a single intravenous dose of 0.03 mg/kg and 0.1 mg/kg MEDI-563, respectively, and their peripheral blood eosinophil levels were enumerated at screening, on day 0 prior to dosing, and at regular intervals up to day 84 and at follow-up. Circulating eosinophils were detected by flow cytometry. Circulating eosinophils decreased below the limit of detection within 24 hours of dosing in all 6 subjects of both cohorts. The MEDI-563 induced eosinopenia lasted for 8-12 weeks. In cohort 1, following the administration of a single dose of 0.03 mg/kg MEDI-563, of the five subjects that completed the 84 day study, eosinophils became detectable in 1 subject at day 58, in 3 subjects at day 84; the fifth subject had no detectable circulating eosinophils at day 84. In cohort 2, following the administration of a single dose of 0.1 mg/kg MEDI-563, none of the subjects had detectable circulating eosinophils at day 84. Peripheral blood eosinophils were detectable, however, in all six subjects of cohort 2 at a subsequent follow-up examination. Peripheral blood eosinophils levels detected in cohorts 1 and 2 at various time intervals following the administration of a single dose of MEDI-563 is presented in FIGS. 18A and 18B.

Example 10

IL-5Rα Immunohistochemistry

Figure 19:
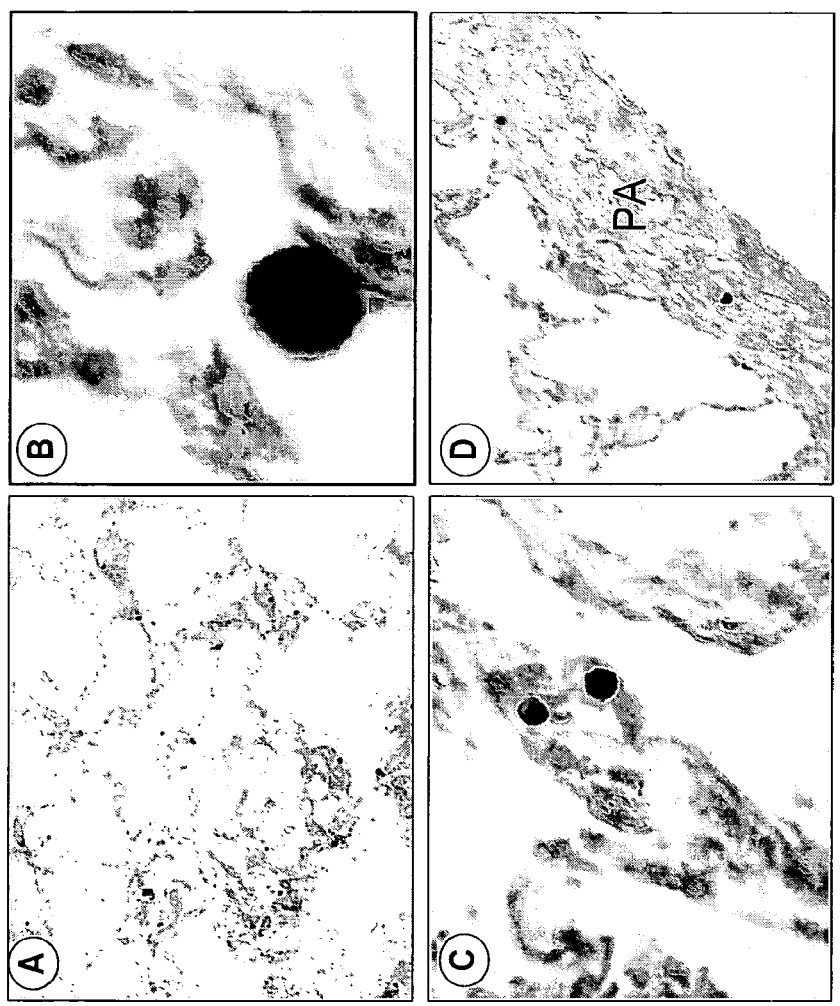
FIG. 19. IL-5Rα is expressed on all eosinophils in normal human lung as analyzed via immunohistochemistry using MEDI-563 and visualized in this figure.

Lung sections from a healthy human subject were stained with MEDI-563 using standard histochemical techniques. Results are summarized in FIG. 19. IL-5R alpha expressing cells appear black in the image.

Figure 20:
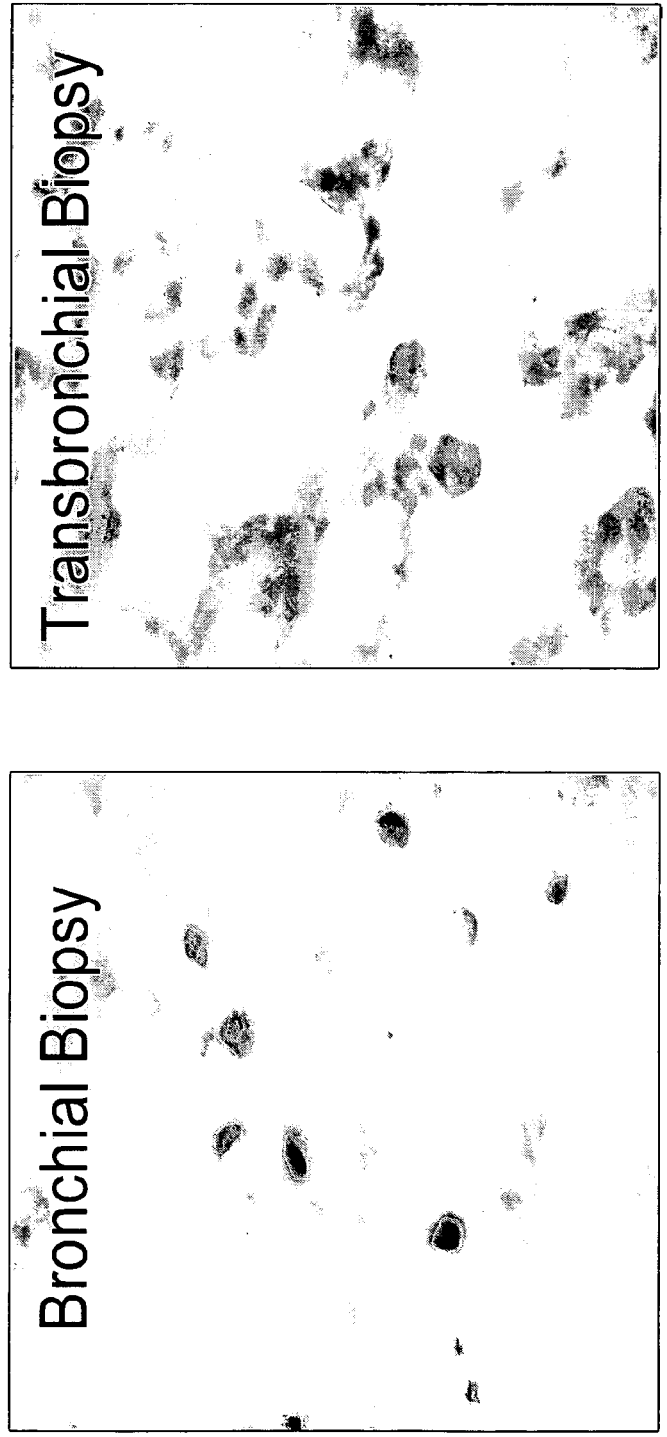
FIG. 20. IL-5Rα is expressed on all eosinophils in lung biopsies from asthmatic human patients as analyzed via immunohistochemistry using MEDI-563 and visualized in this figure.

Lung tissue samples obtained from bronchial or transbronchial biopsy of asthmatic patients were stained with MEDI-563 using standard histochemical techniques. Results are summarized in FIG. 20. IL-5Ralpha expressing cells appear dark grey/black in the image.

Example 11

Figure 21:
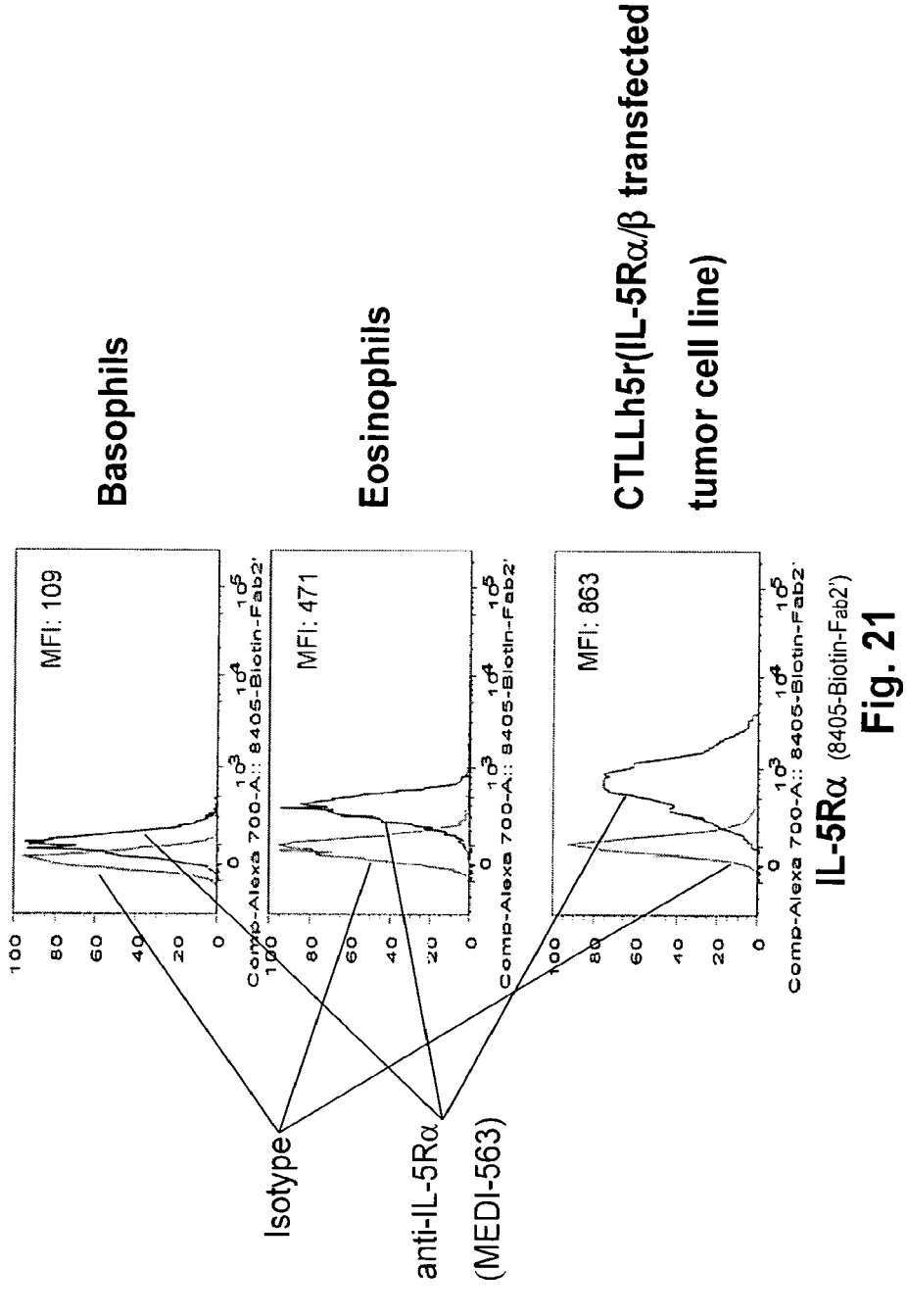
FIG. 21. IL-5Rα expression by primary basophils and eosinophils isolated from healthy donors was analyzed via flow cytometry. Staining profiles obtained using the MEDI 563 anti-IL5Ralpha antibody and an isotype control antibody of irrelevant specificity are shown, CTLLh5r cells (IL-5Ralpha/beta transfected tumor cells) served as a positive control.

MEDI-563 Efficiently Targets Isolated Basophils and Eosinophils in an In Vitro ADCC Assay Basophils and eosinophils were isolated from healthy donors with a commercially available kit (RoboSep™ (automated cell separator) NK/Eosinophil/Basophil Negative Selection Kit, Stem Cell Technologies, Vancouver, Canada). IL-5Ralpha expression of the isolated cells were ascertained by flow cytometry. Cells were stained by MEDI-563 antibody or an isotype control antibody of irrelevant specificity following standard protocols. Immunostained cells were analyzed by flow cytometry. Staining profiles are shown in FIG. 21. Both the isolated basophils and eosinophils displayed a MEDI-563 staining level above that of observed with the isotype control antibody. Staining pattern of a cell line expressing a human IL-5Ralpha/beta transgene is shown as a positive control.

Figure 22:
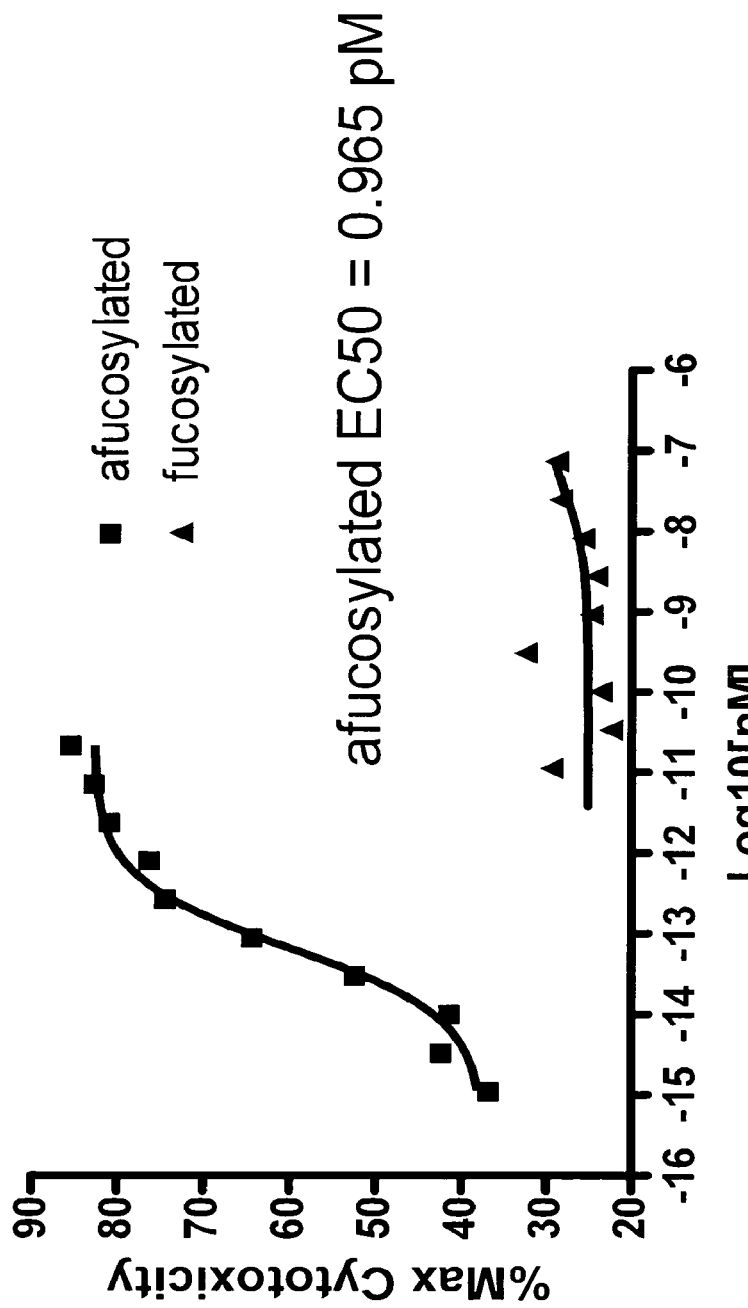
FIG. 22. In vitro antibody dependent cell-mediated cytotoxicity (ADCC) assay: The activity of afucosylated and fucosylated MEDI-563 was compared in an in vitro ADCC assay. Isolated primary NK cells and eosinophils were used as effector and target cells, respectively, at a 5:1 ratio. The assay was performed in the presence of 1 ng/ml human IL-2. Cell death was assessed by flow cytometry based on Annexin V staining. The Y and X axes display percent maximum cytotoxicity and antibody concentration, respectively. The EC50 value for the afucosylated MEDI-563 antibody was 0.965 pM.

The activity of fucosylated and afucosylated MEDI-563 was ascertained in an in vitro ADCC assay using isolated eosinophils and autologous NK cells. Eosinophils and NK cells were isolated from healthy donors using commercially available kits (RoboSep™ (automated cell separator) NK/Eosinophil/Basophil Negative Selection Kit, Stem Cell Technologies, Vancouver, Canada). The ADCC assay was performed with isolated NK cells and eosinophils as effectors and target cells at a 5:1 ratio. Antibody concentrations assayed range from $10^{-15}$ to $10^{-7}$ M. Cytotoxicity was measured after 24 hrs of incubation using a flow cytometry based Annexin V assay. The ADCC activity of afucosylated MEDI-563 was several orders of magnitude higher than that of the fucosylated MEDI-563 antibody. The EC50 value of afucosylated MEDI-563 was 0.965 pM in this assay. The results of a representative experiment are shown in FIG. 22.

Figure 23:
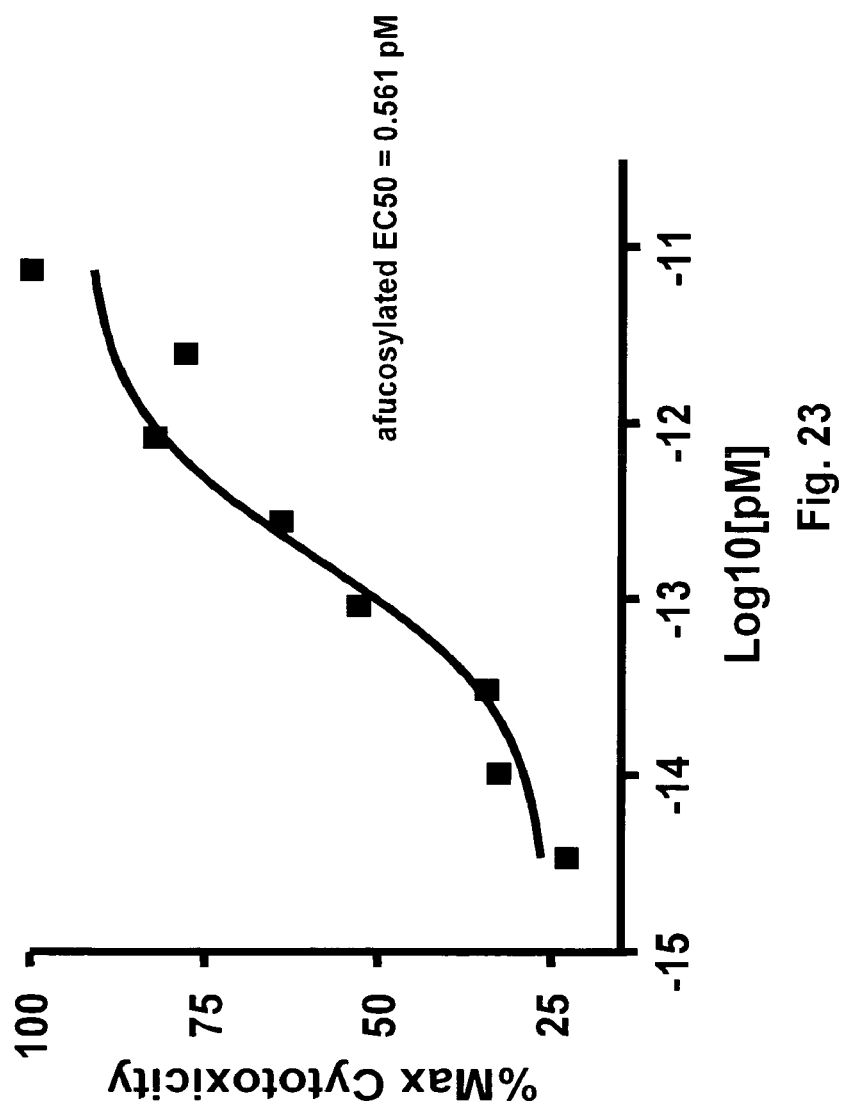
FIG. 23. In vitro antibody dependent cell-mediated cytotoxicity (ADCC) assay: The activity of afucosylated MEDI-563 was analyzed in an in vitro ADCC assay. Isolated primary NK cells and basophils were used as effector and target cells, respectively. The Y and X axes display percent maximum cytotoxicity and antibody concentration, respectively. The EC50 value for the afucosylated MEDI-563 antibody was 0.561 pM in this assay.

The activity of afucosylated MEDI-563 was ascertained in an in vitro ADCC assay using isolated basophils and autologous NK cells. Basophils and NK cells were isolated from healthy donors using commercially available kits (RoboSep™ (automated cell separator) NK/Eosinophil/Basophil Negative Selection Kit, Stem Cell Technologies, Vancouver, Canada). The ADCC assay was performed with isolated NK cells and eosinophils as effectors and target cells at a 5:1 ratio. Antibody concentrations assayed range from $10^{-15}$ to $10^{-11}$ M. Cytotoxicity was measured after 24 hrs of incubation by determining Annexin V positive cells by flow cytometry. The EC50 value of afucosylated MEDI-563 was 0.561 pM in this assay. The results of a representative experiment are shown in FIG. 23.

Example 12

Eosinophils do not Release Cytotoxic Granules in Medi-563 Mediated ADCC Assay

Figure 24:
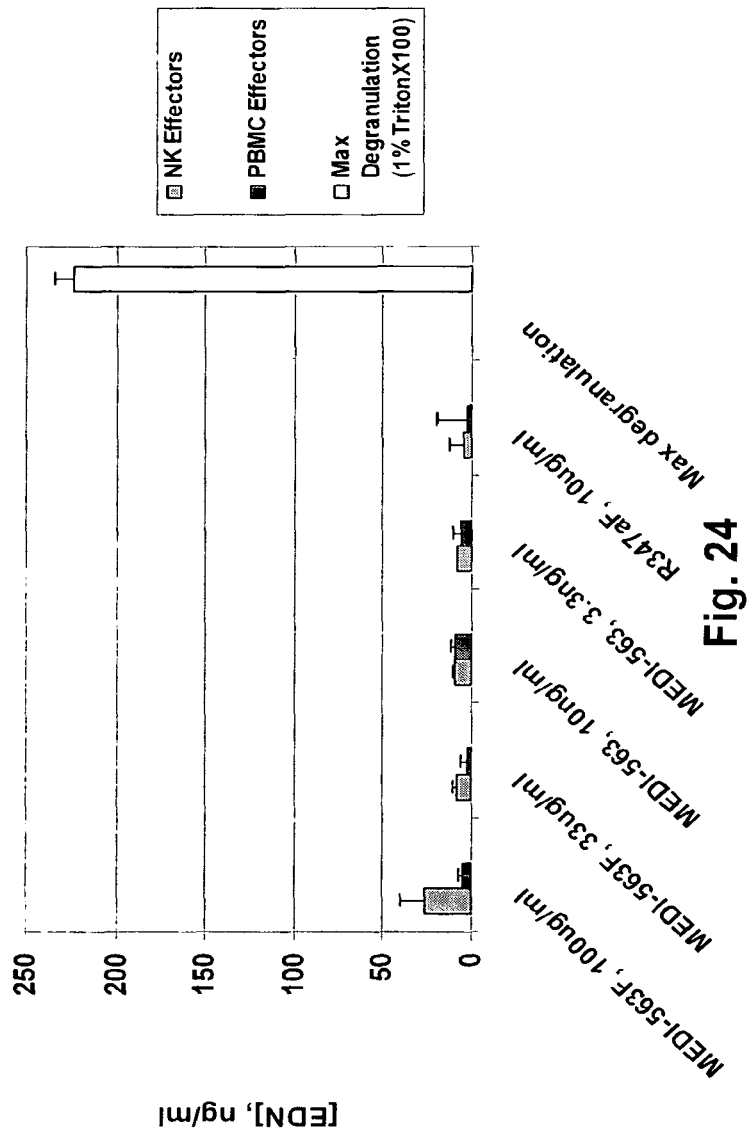
FIG. 24. Eosinophil degranulation in an in vitro antibody dependent cell-mediated cytotoxicity (ADCC) assay: EDN (Eosinophil Derived Neurotoxin) release by eosinophils in an in vitro ADCC assay using various levels of fucosylated (MEDI-563F) and afucosylated (MEDI-563) anti-IL5Ralpha antibody was analyzed. The assay utilized freshly isolated eosinophils and NK or PBMC cells as target and effector cells, respectively. Maximum eosinophil degranulation detected in response to treatment with 1% Triton X-100 is shown for comparison.

Degranulation of eosinophils exposed to MEDI-563 targeted ADCC was ascertained by measuring EDN (eosinophil derived neurotoxin) release into the supernatant. In vitro ADCC conditions used were similar to that of described in Example 11. Eosinophils and NK or PBMC cells isolated from healthy donors were used as target and effector cells, respectively. Assays were performed using fucosylated MEDI-563, afucosylated MEDI-563 or the afucosylated R347 isotyope control antibody. Maximum degranulation was achieved by exposing the eosinophils to 1% triton X-100; EDN concentration >220 ng/ml were detected upon maximum degranulation of the cells. The results of a representative experiment are shown in FIG. 24. EDN levels remained below 25 ng/ml (baseline) following MEDI-563 mediated ADCC. MEDI-563 concentration (33 or 100 μg/ml) or the fucosylation status of the antibody did not significantly affect degranulation levels.

Example 13

MEDI-563 Epitope Mapping

Figure 25A:
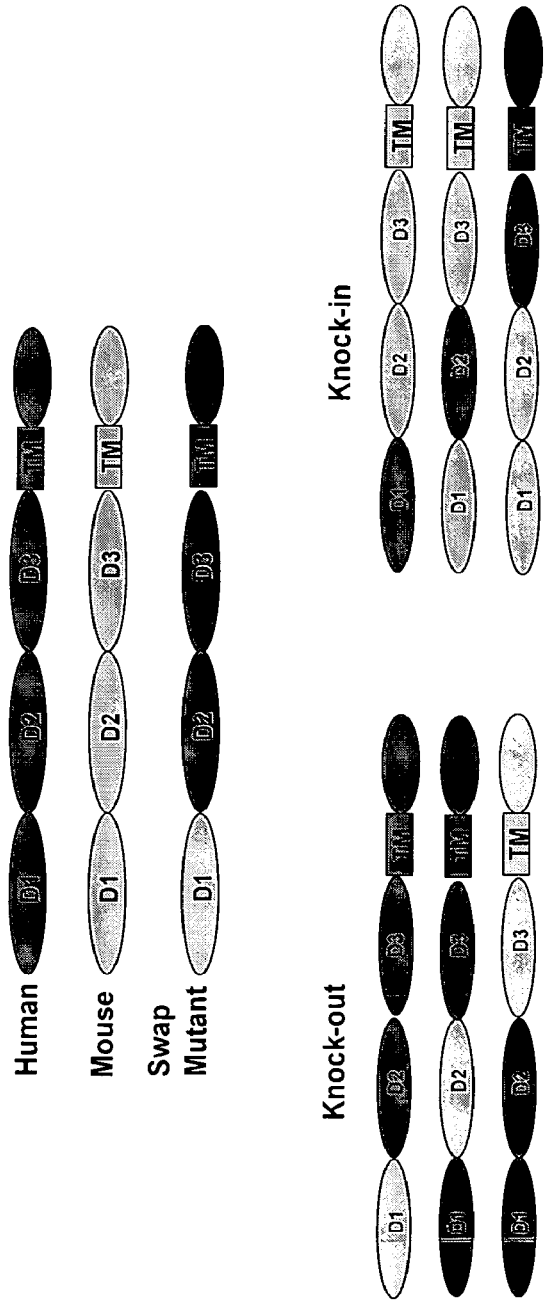
FIG. 25. MEDI-563 specifically binds an epitope within the D1 domain of the extracellular region of human IL-5Ralpha. Antibody binding to transgenic cells transiently expressing chimeric IL-5Ralpha proteins was ascertained by flow cytometry. Fluorescent staining profiles are shown. "Polyclonal" and "MEDI-563" denotes staining profiles observed using a polyclonal anti-human IL-5Ralpha and MEDI-563, respectively, antibodies. "Dual staining" denotes the fluorescent staining profile for the "polyclonal" (x axis) and MEDI-563 (y axis) antibodies. (A) A series of human-mouse chimeric IL-5Ralpha transgenes were expressed transiently. "Knock-out" transgenes were chimeric IL-5Ralpha constructs comprising a single mouse extracellular domain in an otherwise human background. "Knock-in" transgenes were chimeric IL-5Ralpha constructs comprising a single human extracellular domain in an otherwise mouse background. (B) MEDI-563 specifically bound transgenic cells expressing human IL-5Ralpha. MEDI-563 did not bind transgenic cells expressing mouse IL-5Ralpha. (C) MEDI-563 did not bind transgenic cells expressing a chimeric IL-5Ralpha transgene comprising mouse D1 and human D2-D3 extracellular domains ("knock-out D1"). MEDI-563 specifically bound transgenic cells expressing a chimeric IL-5Ralpha transgene comprising mouse D2 or D3 extracellular domains in a human background ("knock-out D2 or D3"). (D) MEDI-563 specifically bound transgenic cells expressing a chimeric IL-5Ralpha transgene comprising human D1 and mouse D2-D3 extracellular domains ("knock-in D1"). MEDI-563 did not bind transgenic cells expressing a mouse IL-5Ralpha based chimeric transgene comprising either the human D2 or D3 extracellular domain ("knock-in D2 or D3").
Figure 25B:
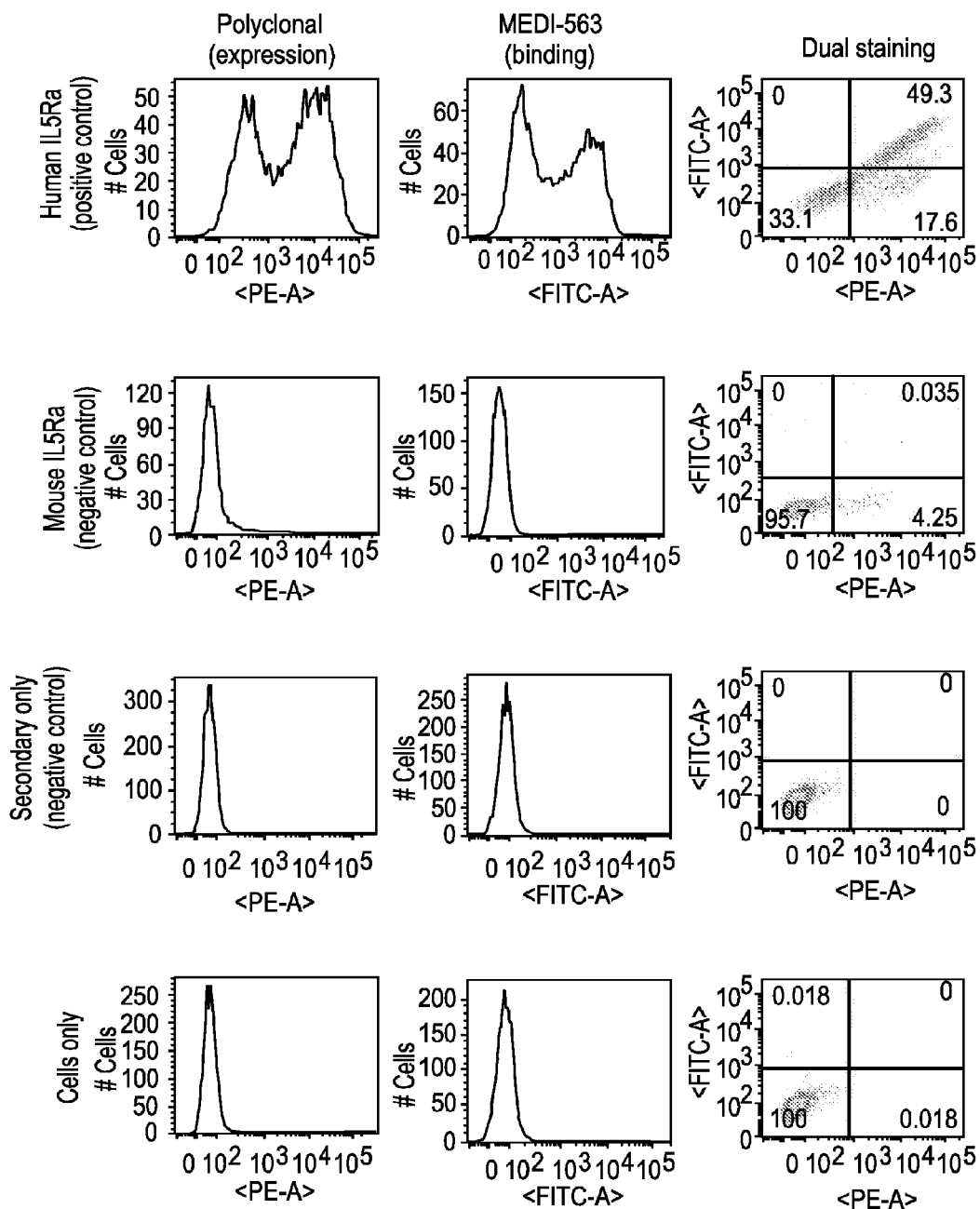

MEDI-563 specifically binds to transgenic cells expressing the human IL-5Ralpha protein. MEDI-563 does not bind to cells expressing a mouse IL-5Ralpha protein. See FIGS. 25B and 26C. The amino acid sequence of mouse and human IL5-Ralpha proteins are highly similar. The epitope specificity of MEDI-563 was determined by analyzing the binding characteristics of MEDI-563 to a large panel of mouse-human chimeric IL-5Ralpha proteins (FIGS. 25-27). The experiments utilized transgenic cells expressing the chimeric IL-5Ralpha proteins on their cell surface. Transgene constructs were generated and expressed using standard molecular methods. Antibody binding to a chimeric IL-5Ralpha protein expressed on the surface of transgenic cells was ascertained by flow cytometry. Fluorescent staining profiles are shown in FIGS. 25-27. "Polyclonal" and "MEDI-563" denotes staining profiles observed using a polyclonal anti-human IL-5Ralpha antibody and MEDI-563, respectively. While MEDI-563 is specific for a single epitope of the human IL-5Ralpha protein, the polyclonal antibody recognizes multiple epitopes of human IL-5Ralpha (FIGS. 25B and 26C). "Dual staining" denotes the fluorescent staining profile for the polyclonal (x axis) and MEDI-563 (y axis) antibodies.

First, the MEDI-563 epitope was mapped to the D1 region of the extracellular domain of IL-5Ralpha. IL-5Ralpha comprises 3 extracellular domains (D1, D2 and D3), a transmembrane domain and an intracellular domain (FIG. 25A). Because MEDI-563 recognizes IL-5Ralpha on intact cells, its epitope must be located in one of the extracellular domains. To map the MEDI-563 epitope to one of the three extracellular domains, transgenic cells expressing chimeric IL-5Ralpha proteins comprising mouse and human extracellular domains were generated using standard molecular cloning methods. A schematic representation of the chimeric proteins tested are shown in FIG. 25A. "Knock-out" variants were chimeric IL-5Ralpha proteins comprising a single mouse extracellular domain in an otherwise human background. "Knock-in" variants were chimeric IL-5Ralpha proteins comprising a single human extracellular domain in an otherwise mouse background.

Figure 25C:
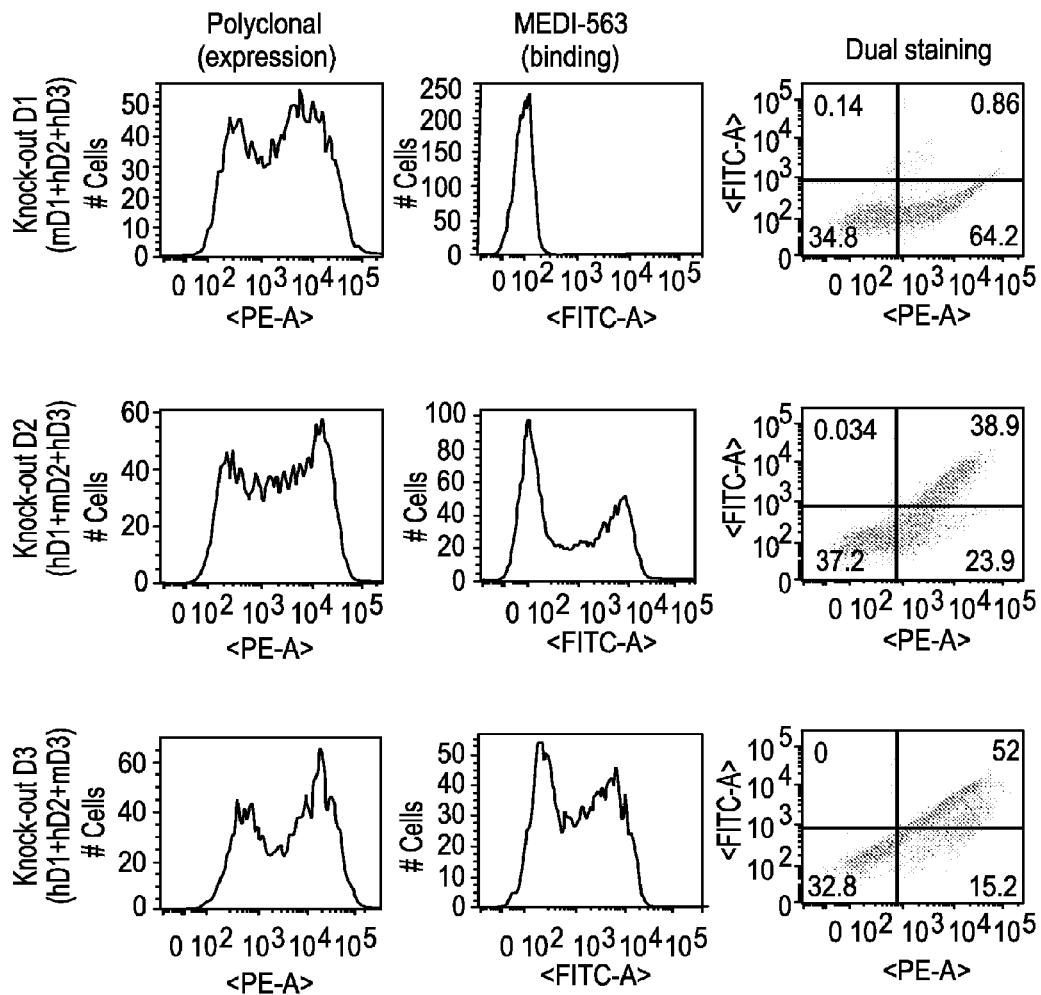
Figure 25D:
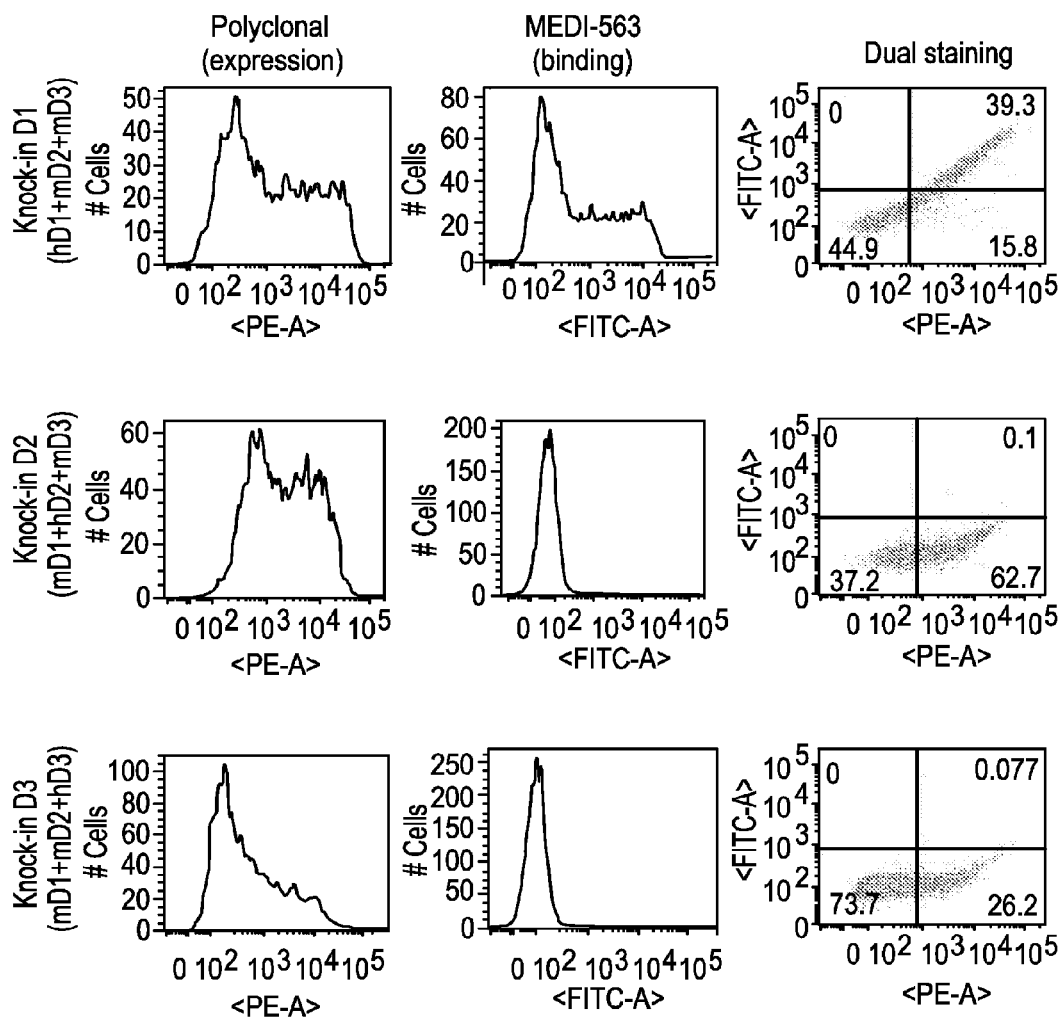
Figure 26C:
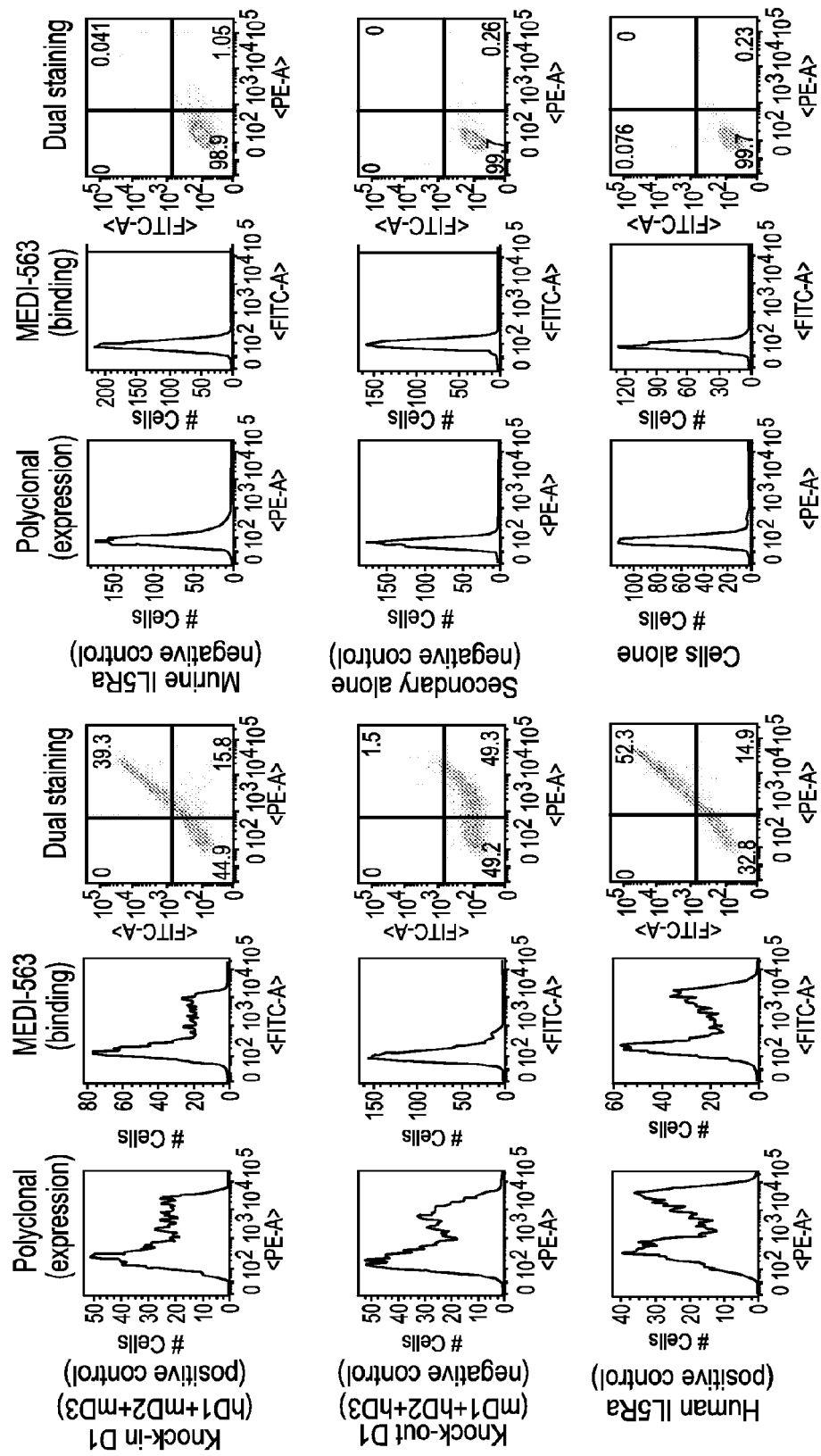
FIG. 26. MEDI-563 specifically binds an epitope within Segment B of the D1 extracellular domain of human IL-5Ralpha. Antibody binding to transgenic cells expressing a chimeric IL-5Ralpha protein was ascertained by flow cytometry. Fluorescent staining profiles are shown. "Polyclonal" and "MEDI-563" denotes staining profiles observed using a polyclonal anti-human IL-5Ralpha and MEDI-563, respectively, antibodies. "Dual staining" denotes the fluorescent staining profile for the polyclonal (x axis) and MEDI-563 (y axis) antibodies. (A) The amino acid sequence of the D1 extracellular domain of mouse IL-5Ralpha is 75% identical to that of the human IL-5Ralpha protein. The D1 extracellular domain of IL-5Ralpha was divided into Segments A, B and C. The human and mouse IL-5Ralpha amino acid sequences shown are residues 1-102 of SEQ ID NO: 5 and 6, respectively. (B) A series of human-mouse chimeric IL-5Ralpha transgenes were expressed transiently. "Knockout" transgenes were chimeric IL-5Ralpha constructs comprising a single mouse Segment of the D1 extracellular domain in an otherwise human background. "Knock-in" transgenes were chimeric IL-5Ralpha constructs comprising a single human Segment of the D1 extracellular domain in an mouse D1-human D2-mouse D3-mouse TM background. (C) MEDI-563 specifically recognized transgenic cells expressing (i) a human IL-5Ralpha transgene or (ii) a mouse IL-5Ralpha chimeric transgene comprising a human D1 extracellular domain (:knock-in D1"). MEDI-563 did not bind transgenic cells expressing (i) mouse IL-5Ralpha receptor transgene or (ii) a human chimeric IL-5Ralpha transgene comprising a mouse D1 extracellular domain. (D) MEDI-563 did not bind transgenic cells expressing a chimeric IL-5Ralpha transgene comprising a mouse Segment B of the D1 extracellular domain in an otherwise human background ("knock-out B"). MEDI-563 specifically bound transgenic cells expressing a chimeric IL-5Ralpha transgene comprising mouse Segment A or C of the D1 extracellular domains in a human background ("knock-out A or C"). (E) MEDI-563 specifically bound transgenic cells expressing a chimeric IL-5Ralpha transgene comprising a human Segment B of the D1 extracellular domain in a mouse D1-human D2-mouse D3-mouse TM background ("knock-in B"). MEDI-563 did not bind transgenic cells expressing a chimeric IL-5Ralpha transgene that comprised a human Segment A or C in an mouse D1-human D2-mouse D3-mouse TM background ("knock-in A or C").

FIG. 25B-C shows the result of a representative experiment. Both MEDI-563 and the polyclonal antibody stained transgenic cells expressing the human IL-5Ralpha protein; neither antibody stained transgenic cells expressing mouse IL-5Ralpha (FIG. 25B). MEDI-563 did not bind transgenic cells expressing a chimeric IL-5Ralpha transgene comprising mouse D1 and human D2-D3 extracellular domains (FIG. 25C; "knock-out D1"). MEDI-563 specifically bound transgenic cells expressing a chimeric IL-5Ralpha transgene comprising mouse D2 or D3 extracellular domains in a human background (FIG. 25C; "knock-out D2 or D3"). MEDI-563 specifically bound transgenic cells expressing a chimeric IL-5Ralpha transgene comprising human D1 and mouse D2-D3 extracellular domains (FIG. 25D; "knock-in D1"). MEDI-563 did not bind to transgenic cells expressing a mouse IL-5Ralpha based chimeric transgene comprising either the human D2 or D3 extracellular domain (FIG. 25D; "knock-in D2 or D3"). All cells expressing a chimeric IL-5Ralpha protein comprising at least one extracellular domain of the human protein were stained by the polyclonal anti-human IL-5Ralpha antibody showing that the difference in MEDI-563 staining pattern among the transgenic cells was not due to a difference in chimeric protein expression level.

Figure 26D:
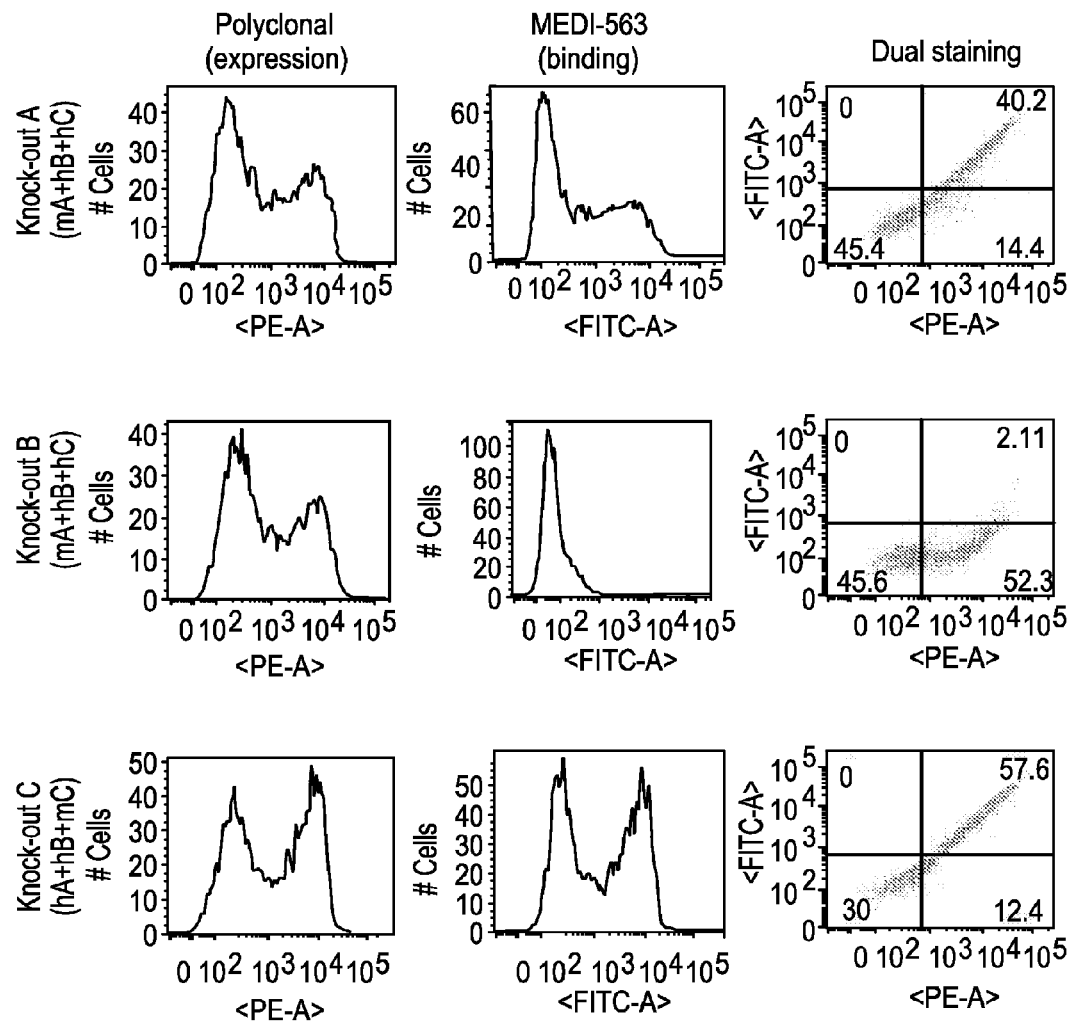
Figure 26E:
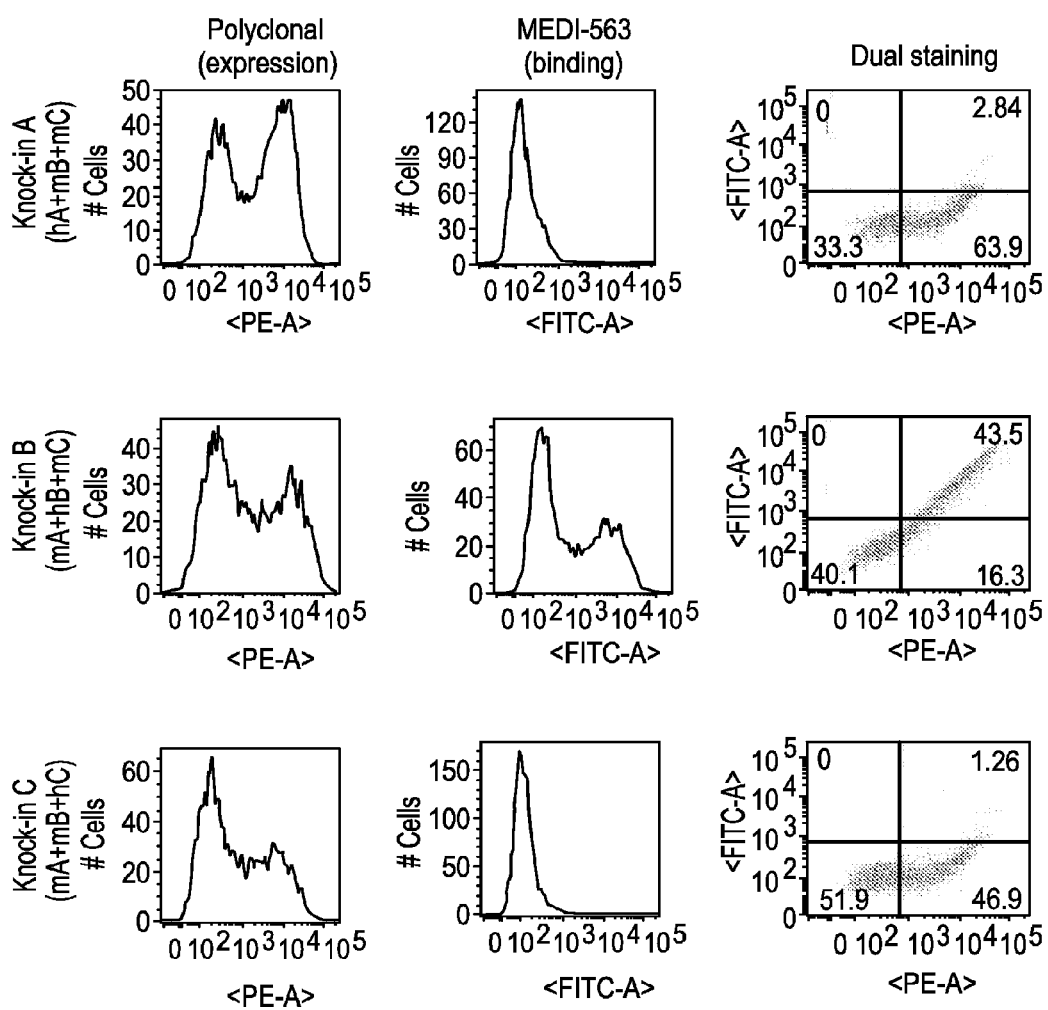

Second, the MEDI-563 epitope was mapped to Segment B of the D1 extracellular domain of human IL-5Ralpa (FIG. 26). The D1 extracellular domain of IL-5Ralpha was divided into three segments (FIG. 26A; Segment A, B and C). A series of human-mouse chimeric IL-5Ralpha transgenes comprising various combinations of human and mouse Segments of the D1 extracellular domain were generated; the chimeric proteins used at this stage comprised all human sequences outside the D1 extracellular domain. "Knock-out" transgenes were chimeric IL-5Ralpha constructs comprising a single mouse Segment of the D1 extracellular domain in an otherwise human background. "Knock-in" transgenes were chimeric IL-5Ralpha constructs comprising a single human Segment of the D1 extracellular domain in a mouse D1-human D2-mouse D3-mouse TM background (FIG. 26B). FIG. 26C shows the result of a control experiment. MEDI-563 specifically recognized transgenic cells expressing (i) a human IL-5Ralpha transgene or (ii) a mouse IL-5Ralpha chimeric transgene comprising a human D1 extracellular domain ("human IL-5Ra" and "knock-in D1"). MEDI-563 did not bind transgenic cells expressing (i) mouse IL-5Ralpha receptor transgene or (ii) a human chimeric IL-5Ralpha transgene comprising a mouse D1 extracellular domain ("mouse IL-5Ra", "knock out-D1"). FIGS. 26D and E shows the result of a representative mapping experiment. MEDI-563 did not bind to transgenic cells expressing a chimeric IL-5Ralpha transgene comprising a mouse Segment B of the D1 extracellular domain in an otherwise human background ("knock-out B"). MEDI-563 specifically bound transgenic cells expressing a chimeric IL-5Ralpha transgene comprising mouse Segment A or C of the D1 extracellular domains in a human background ("knock-out A", "knock out-C"). FIG. 26E shows an example of results obtained with the knock in constructs. MEDI-563 specifically bound transgenic cells expressing a chimeric IL-5Ralpha transgene comprising human Segment B of the D1 extracellular domain in a mouse D1-human D2-mouse D3-mouse TM background ("knock-in B"). MEDI-563 did not bind transgenic cells expressing a chimeric IL-5Ralpha transgene comprising a human Segment A or C of the D1 extracellular domain in a mouse D1-human D2-mouse D3-mouse TM background ("knock-in A or C"). All cells expressing a chimeric IL-5Ralpha protein were stained by the polyclonal anti-human IL-5Ralpha antibody showing that the difference in MEDI-563 staining pattern among the transgenic cells was not due to a difference in chimeric protein expression level.

Figure 27A:
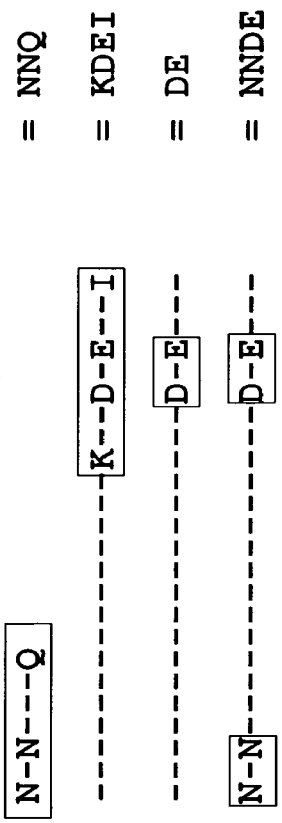
FIG. 27. MEDI-563 specifically binds an epitope of human IL-5Ralpha comprising amino acid residue Ile61 of the D1 extracellular domain. Antibody binding to transgenic cells expressing a variant IL-5Ralpha protein was ascertained by flow cytometry. Fluorescent staining profiles are shown. "Polyclonal" and "MEDI-563" denotes staining profiles observed using a polyclonal anti-human IL-5Ralpha and MEDI-563, respectively, antibodies. "Dual staining" denotes the fluorescent staining profile for the polyclonal (x axis) and MEDI-563 (y axis) antibodies. (A) Residues 50-61 of the D1 extracellular domain of human IL-5Ralpha are shown (residues 40-61 of SEQ ID NO:5). Residues shown in italics are different in the corresponding region of the mouse IL-5Ralpha protein. A series of IL-5Ralpha receptor variants comprising at least one mutant amino acid residue were expressed in transgenic cells. The "knock-out" IL-5Ralpha variants were mutant human proteins comprising at least one substitution exchanging a human residue for the corresponding mouse residue. For example, the "knock-out DE" variant is a human IL-5Ralpha protein comprising the D56E and E58D amino acid substitutions. The "knock-in" IL-5Ralpha variants were chimeric proteins comprising the mouse D1, human D2, mouse D3 and mouse TM domains wherein the mouse D1 domain comprised a mutant Segment B having at least one substitution exchanging a mouse residue for the corresponding human residue. For example, the "knock-in DE" variant was a chimeric IL-5Ralpha protein comprising a mutant mouse Segment B wherein the mutant mouse segment B comprised the E56D and D58E amino acid substitutions. (B) MEDI-563 did not bind transgenic cells expressing a mutant human IL-5Ralpha protein comprising the K53Q, D56E, E58D, I61K amino acid substitutions ("knock out-KDEI"). MEDI-563 specifically binds to transgenic cells expressing a mutant human IL-5Ralpha protein comprising the N40H, N42D, Q46H ("knock out-NNQ") or D56E, E58D ("knock out-DE"), or N40H, N42D, D56E, E58D ("knock out-NNDE") amino acid substitutions. (C) MEDI-563 specifically bound transgenic cells expressing a chimeric IL-5Ralpha protein comprising a mutant mouse Segment B wherein the mutant mouse Segment B comprised the Q53K, E56D, D58E, K61I amino acid substitutions ("knock in-KDEI"). (D) MEDI-563 did not bind transgenic cells expressing a mutant human IL-5Ralpha protein comprising the I61K amino acid substitution ("knock out-I61"). MEDI-563 specifically binds to transgenic cells expressing a mutant human IL-5Ralpha protein comprising the K53Q ("knock out-K53") amino acid substitution. (E) MEDI-563 specifically bound transgenic cells expressing a chimeric IL-5Ralpha protein comprising a mutant mouse Segment B wherein the mutant mouse Segment B comprised the K61I amino acid substitution ("knock in-I61"). MEDI-563 did not bind transgenic cells expressing a chimeric IL-5Ralpha protein comprising a mutant mouse Segment B wherein the mutant mouse Segment B comprised the Q53K amino acid substitution ("knock in-K53").
Figure 27B:
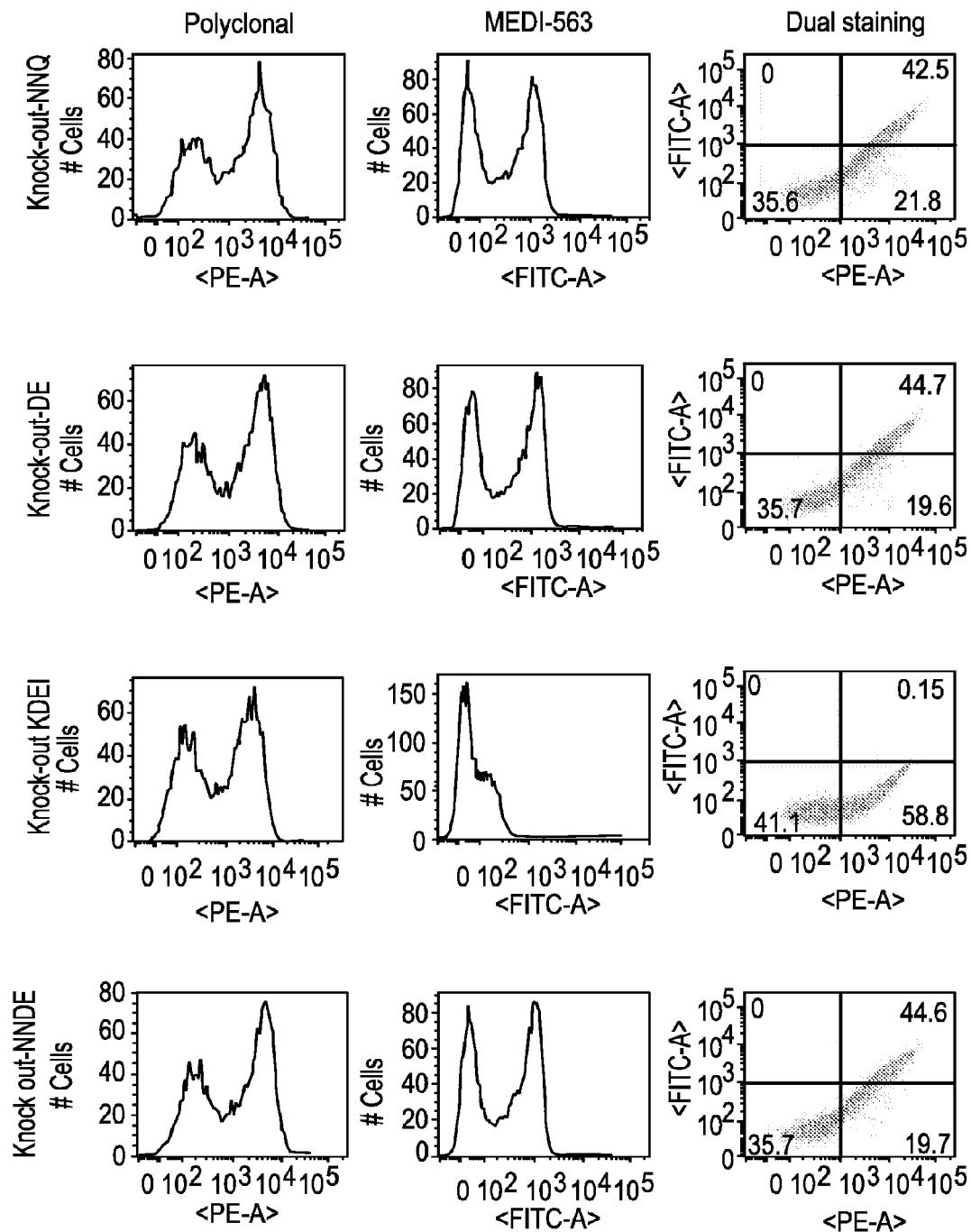
Figure 27C:
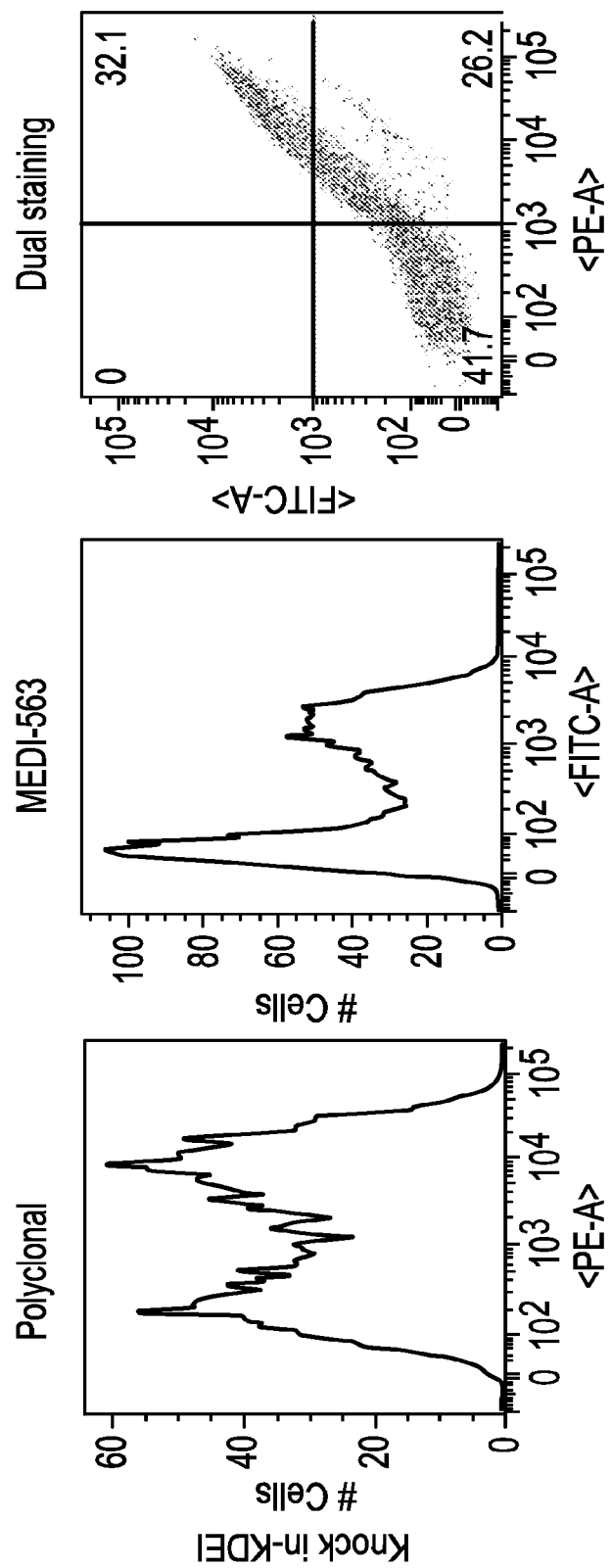
Figure 29A:
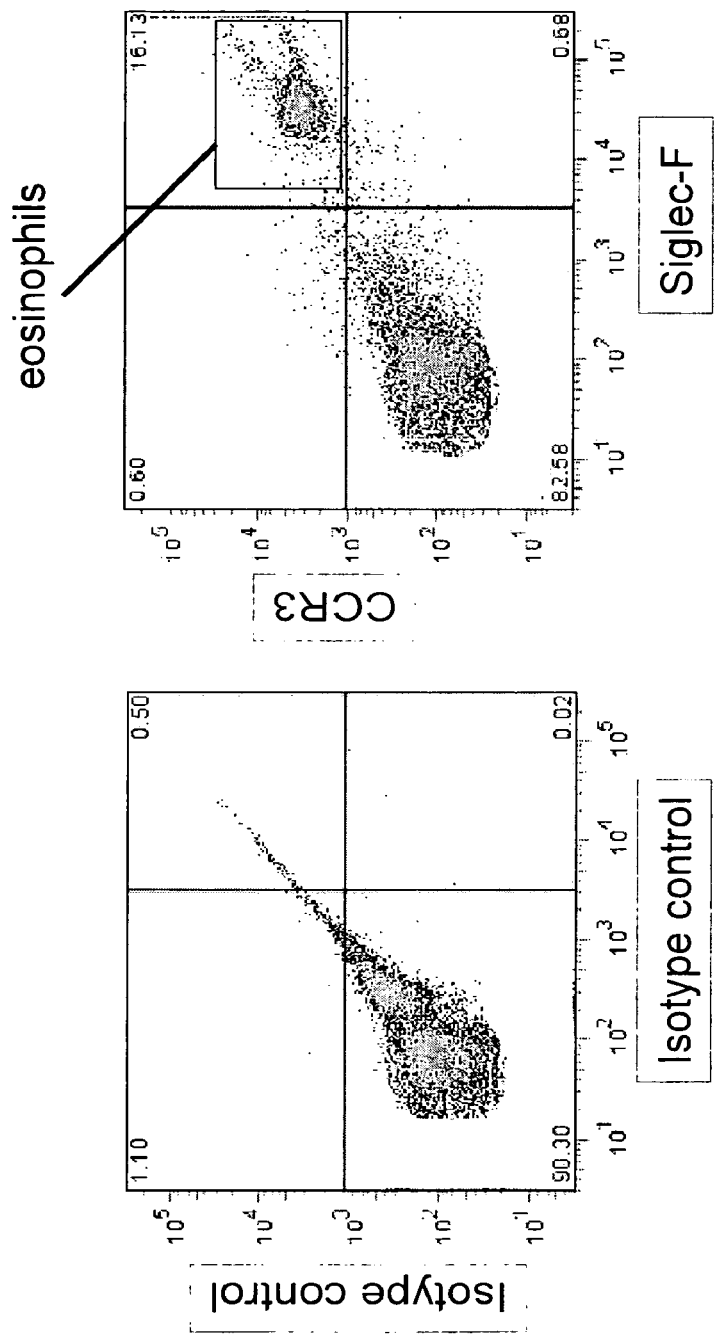
FIG. 29. (A) Eosinophils were identified by flow cytometric analysis as cells with high side scatter that stained positively for CCR3 and Siglec-F. (B) IL-5R was selectively expressed by eosinophils in bone marrow, blood, spleen and lung tissue of IL-5Tg mice.
Figure 29B:
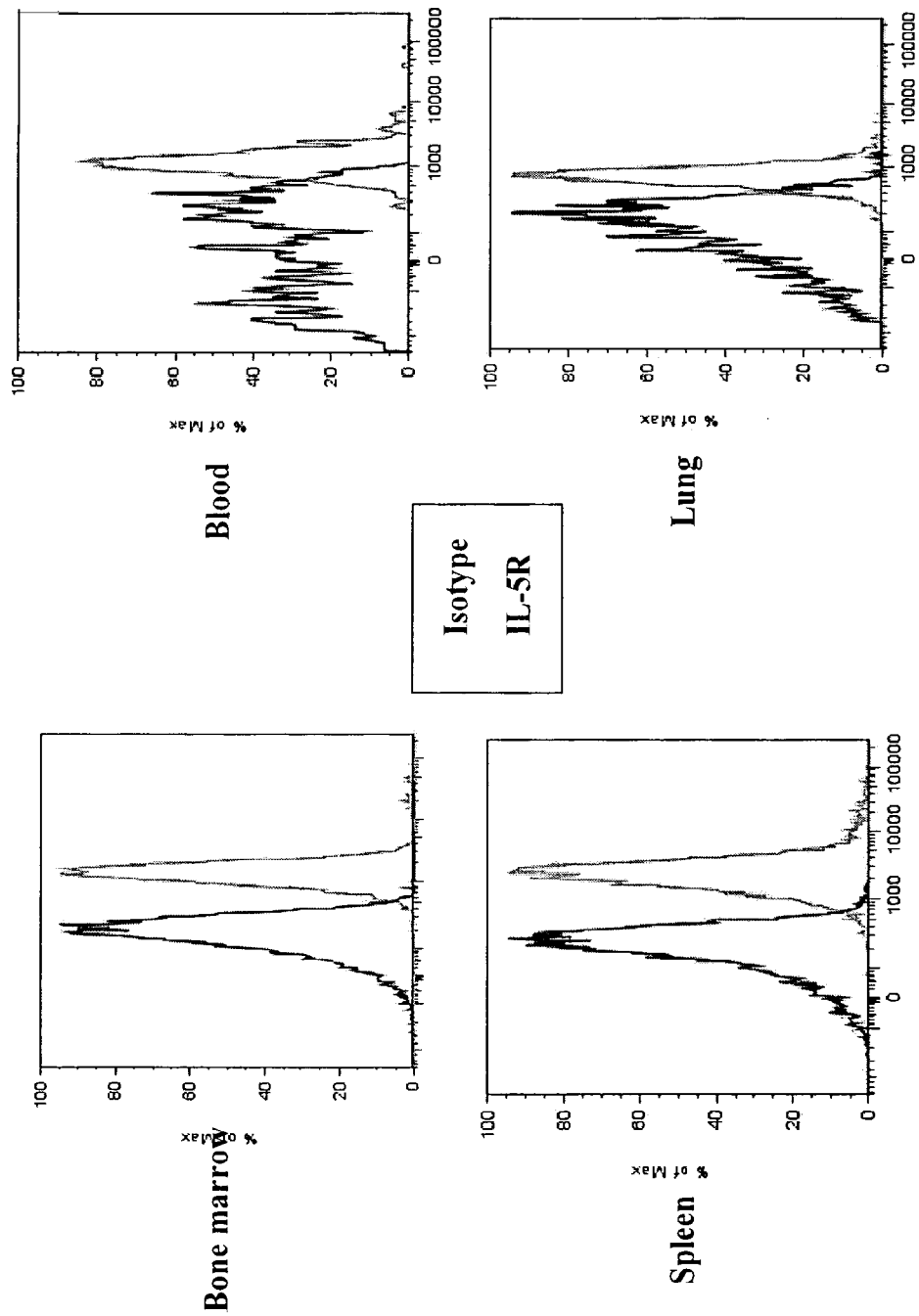
Figure 30A:
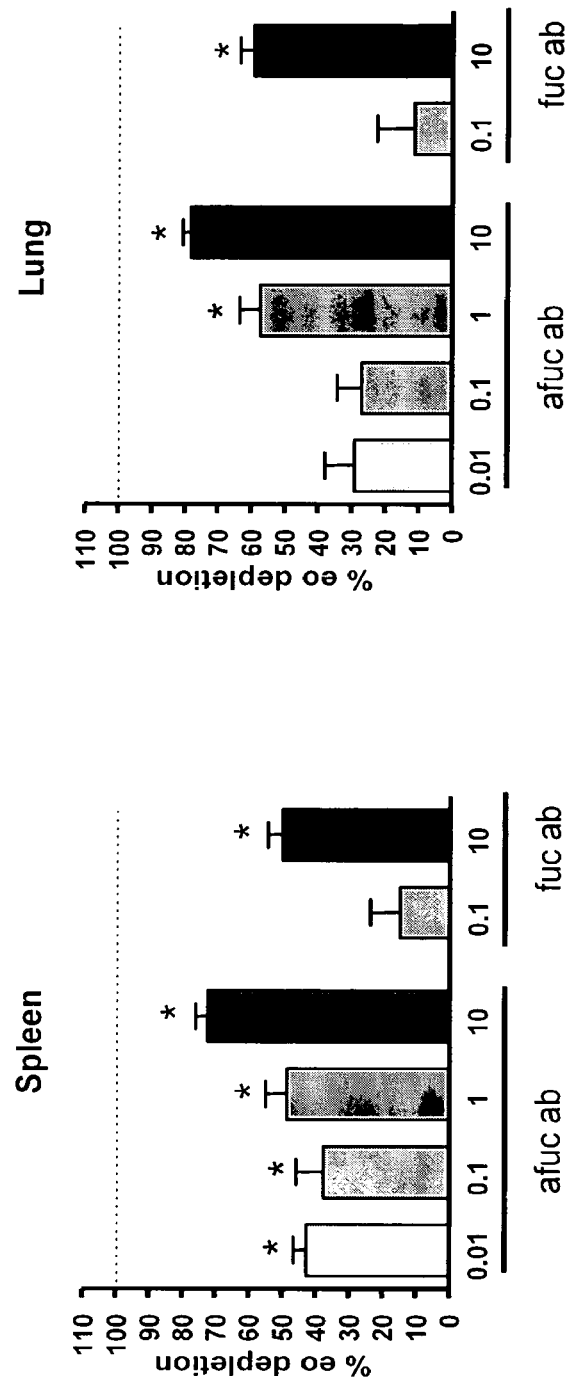
FIG. 30. Both afuc and fuc 1-17 depleted eosinophils in spleen (A), lung tissue (A) and blood (B) of IL-5Tg mice. No depletion was detected in the bone marrow (B). Afuc H7 was more potent at removing eosinophils compared with fuc H7, especially at lower antibody doses. Data are expressed as mean±SEM, n=6-8 mice/group, p<0.05 antibody treated compared with Control IgG treated, Mann-Whitney U test.
Figure 30B:
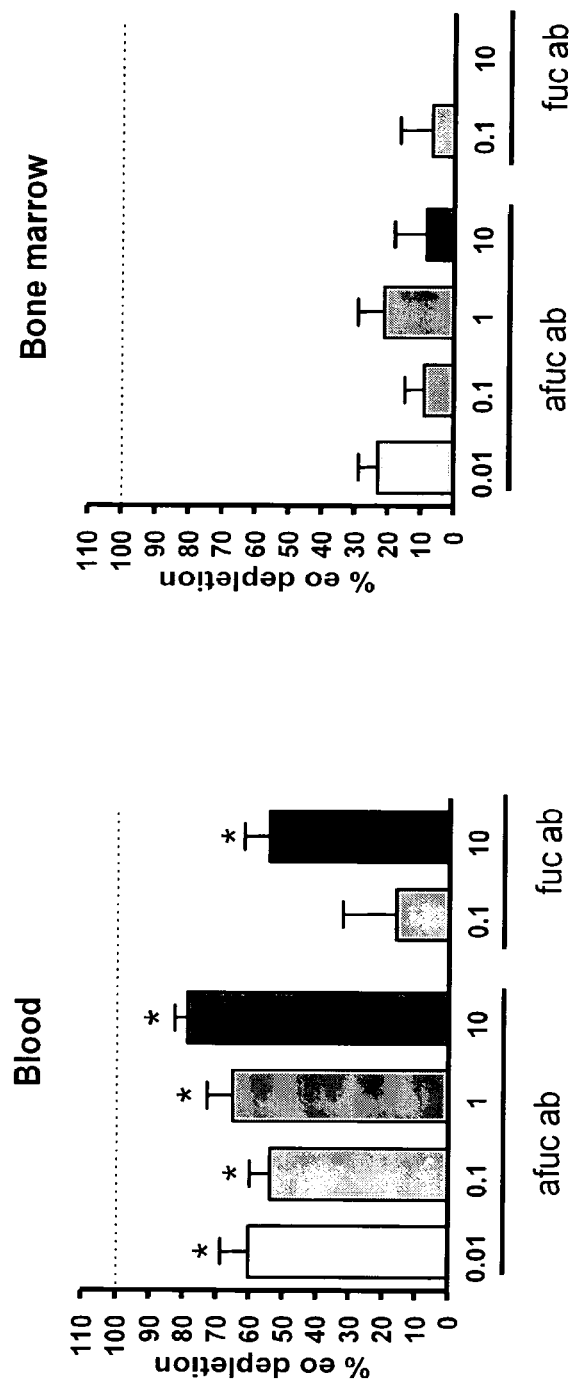
Figure 31:
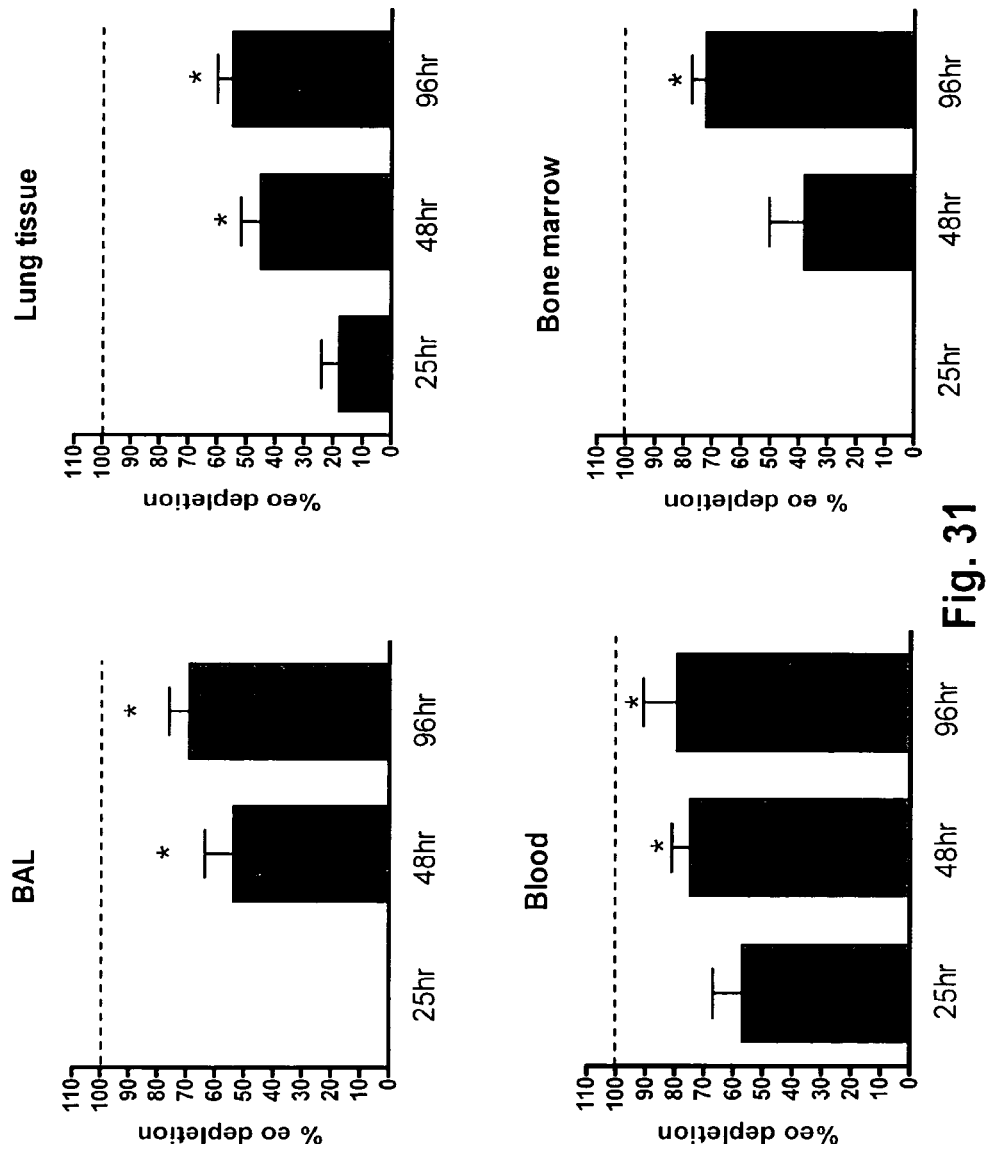
FIG. 31. Afuc H7 also depletes eosinophils in an allergen challenge model. Afuc H7 depleted eosinophils in the airway lumen, lung tissue, blood and bone marrow. Depletion was highest in all compartments 72 h after the final challenge (96 h after antibody delivery). Data are expressed as mean±SEM, n=6 mice/group, *p<0.05 antibody treated compared with Control IgG treated, Mann-Whitney U test.

Third, the MEDI-563 epitope was mapped to particular amino acid residues within Segment B1 of the D1 extracellular domain of human IL-5Ralpha. A series of IL-5Ralpha receptor variants comprising at least one mutant amino acid residue within Segment B1 of the D1 extracellular domain were expressed in transgenic cells. The position of mutant residues were selected by comparing the mouse and human amino acid sequence. A schematic of the variant proteins tested are shown in FIG. 27A. The "knock-out" IL-5Ralpha variants were mutant human proteins comprising at least one substitution exchanging a human residue for the corresponding mouse residue. For example, the "knock-out DE" variant was a human IL-5Ralpha protein comprising the D56E and E58D amino acid substitutions. The "knock-in" IL-5Ralpha variants were chimeric proteins comprising mouse D1, human D2, mouse D3 and mouse TM wherein the mouse D1 domain comprised a mutant version of mouse Segment B having at least one substitution exchanging a mouse residue for the corresponding human residue. For example, the "knock-in DE" variant was a chimeric IL-5Ralpha protein comprising mutant mouse Segment B in a mouse D1-human D2-mouse D3-mouse TM background wherein the mutant mouse Segment B comprised the E56D and D58E amino acid substitutions. FIG. 27B shows an example of the results obtained using the knock out constructs. MEDI-563 did not bind transgenic cells expressing a mutant human IL-5Ralpha protein comprising the K53Q, D56E, E58D, I61K amino acid substitutions ("knock out-KDEI"). MEDI-563 specifically bound transgenic cells expressing a mutant human IL-5Ralpha protein comprising the N40H, N42D, Q46H ("knock out-NNQ") or D56E, E58D ("knock out-DE"), or N40H, N42D, D56E, E58D ("knock out-NNDE") amino acid substitutions. FIG. 27C shows an example of the results obtained using the knock in constructs. MEDI-563 specifically bound transgenic cells expressing a variant IL-5Ralpha protein comprising a mutant mouse Segment B of D1 having the Q53K, E56D, D58E, K61I amino acid substitutions ("knock in-KDEI"). FIG. 27D shows an example of the results obtained using the knock out constructs. MEDI-563 did not bind transgenic cells expressing a mutant human IL-5Ralpha protein comprising the I61K amino acid substitution ("knock out-I61"). MEDI-563 specifically bound transgenic cells expressing a mutant human IL-5Ralpha protein comprising the K53Q ("knock out-K53") amino acid substitution. (E) FIG. 27E shows an example of the results obtained using the knock in constructs. MEDI-563 specifically bound transgenic cells expressing a variant IL-5Ralpha protein comprising a mutant mouse Segment B of D1 having the K61I amino acid substitution ("knock in-I61"). MEDI-563 did not bind transgenic cells expressing a variant IL-5Ralpha protein comprising a mutant mouse Segment B of D1 having the Q53K amino acid substitution ("knock in-K53"). All cells expressing a chimeric IL-5Ralpha protein were stained by the polyclonal anti-human IL-5Ralpha antibody showing that the difference in MEDI-563 staining pattern among the transgenic cells was not due to a difference in chimeric protein expression level.

Example 14

In Vivo Depletion of Eosinophils from Various Tissues

We assessed the potency of an afucosylated anti-mouseIL-5Ra antibody (afuc H7) to selectively deplete eosinophils from various tissues in vivo in comparison with fucosylated H7 (fuc H7).

Methods: Monoclonal Antibody H7:

The variable regions of H7 were grafted onto hIgG1 Fc. Fuc H7 was expressed in wild-type CHO cells and afuc H7 in CHO cells deficient in FUT8.

Antibody affinities (KD):

Affinities were measured using surface plasmon resonance technology.

Mice:

IL-5 transgenic mice, and BALB/c mice were used at 6-8 weeks of age.

Depletion of Eosinophils in IL-5Tg Mice:

Mice were dosed with 0.01-10 mg/kg afuc and fuc H7 i.p. and eosinophil numbers were analyzed 48 h later.

Induction of Allergic Airway Inflammation:

BALB/c mice were sensitized to OVA in alum and challenged with OVA on days 17-22. Mice were dosed with 0.1 mg/kg afuc H7 i.p. on day 22 and analysis was performed 1 hr, 24 hrs and 72 hrs after the final challenge. This corresponded to 25, 48 and 96 hrs post-antibody treatment.

Isolation of Leukocytes:

i) Blood Blood was collected by cardiac puncture and kept in heparinised tubes. Blood leukocytes were phenotyped using a Sysmex Hematology Analyser (Sysmex Corp.), or by flow cytometry.

ii) Airway lumen Airways were lavaged with 3×0.6 ml PBS. BAL samples were centrifuged at 1200 rpm, supernatants were removed, and cells resuspended in RPM I. Cells were counted using a Coulter Z2 counter (Beckman-Coulter), and phenotyped by flow cytometry.

iii) Lung tissue One lobe of lung was incubated at 37° C. for 1 h in digest reagent (18 µg/ml Liberase™ [Blenzyme 2; Roche], 25 µg/ml DNase [type 1; Roche]) in RPMI/10% FCS. The recovered cells were filtered through a 70-µm nylon sieve (Falcon), washed twice, and counted and phenotyped as for BAL.

iv) Bone marrow Femurs from donor mice were isolated, and the marrow was flushed out with a syringe attached to a 25-gauge needle containing PBS (without calcium/magnesium). Single cell suspensions were prepared by flushing the marrow gently up and down in a syringe attached to a 22-gauge needle. The bone marrow cells were centrifuged at 1200 rpm for 5 minutes, washed twice with PBS without additives, resuspended in RPMI, counted and phenotyped by flow cytometry.

v) Spleen Spleens were removed and single cell suspensions were prepared using 70-µm nylon sieves. Leukocytes were resuspended in RPMI, counted and phenotyped as for BAL.

Flow Cytometry

Cells were phenotyped using flow cytometric analysis. Antibodies used were anti-mouse CD4, CD19, CD11b, Siglec-F, Gr-1, IL-5R, c-kit (BD Biosciences), FcεR1 (eBiosciences), and CCR-3 (R and D Systems), and their relevant isotype controls. Samples were analyzed using an LSR11 flow cytometer and FACS DIVA software (BD Biosciences). Results were further analyzed using FlowJo (TreeStar Corp.)

Identification of Eosinophils:

Eosinophils were identified by flow cytometric analysis as cells with high side scatter that stained positively for CCR3 and Siglec-F.

Results:

IL-5R was selectively expressed by eosinophils in bone marrow, blood, spleen and lung tissue of IL-5Tg mice. IL-5R expression was restricted to eosinophils and was not detected on any other cell type, including mast cells or basophils. Anti-IL-5R antibody selectively depletes eosinophils in spleen, lung tissue and blood of IL-5Tg mice. Neither afucosylated nor fucosylated anti-IL-5R depleted: Neutrophils (Gr-1hi); Macrophages/monocytes (CD11b+); T cells (CD3+); B cells (CD19+). Both afuc and fuc H7 depleted eosinophils in spleen, lung tissue and blood of IL-5Tg mice. No depletion was detected in the bone marrow. Afuc H7 was more potent at removing eosinophils compared with fuc H7, especially at lower antibody doses.

Afuc H7 also selectively depletes eosinophils in an allergen challenge model. Afuc H7 depleted eosinophils in the airway lumen, lung tissue, blood and bone marrow. Depletion was highest in all compartments 72 h after the final challenge (96 h after antibody delivery).

Whereas, particular embodiments of the invention have been described above for purposes of description, it will be appreciated by those skilled in the art that numerous variations of the details may be made without departing from the invention as described in the appended claims.

All publications, patents and patent applications mentioned in this specification are herein incorporated by reference into the specification to the same extent as if each individual publication, patent or patent application was specifically and individually indicated to be incorporated herein by reference. In addition, U.S. Provisional Application Nos. 60/924,422, filed May 14, 2007, 60/924,832, filed Jun. 1, 2007, 60/935,005, filed Jul. 20, 2007, and 61/064,612, filed Mar. 14, 2008, are hereby incorporated by reference in their entirety for all purposes.

---

The invention claimed is:

1. A method of reducing the numbers of peripheral blood basophils in an asthmatic subject comprising parenterally administering to said subject in need thereof between 0.01 to 0.25 mg/kg of an anti-Interleukin-5 receptor (IL-5R) antibody comprising the amino acid sequences of SEQ ID NO: 1 and SEQ ID NO:3 and comprising an immunoglobulin Fc region comprising no fucose, wherein the administration of the antibody reduces the number of peripheral blood basophils from the asthmatic subject's circulation by 5 to 70 basophils/mm$^3$ by 24 hours post-administration.

2. The method of claim 1, wherein the reduction of basophils is reversible.

3. The method of claim 1, wherein the numbers of basophils are reduced to a level that is less than 9 basophils/mm$^3$.

4. The method of claim 1, wherein there is a post-administration reduction in absolute basophil count of at least 5, at least 10, at least 15, at least 20, at least 25, at least 30, at least 35, at least 40, at least 45, at least 50, at least 55, at least 60, at least 65, or at least 70 basophils/mm$^3$.

5. The method of claim 1, wherein said subject's pre-administration absolute basophil count is between 5 and 500 basophils/mm$^3$.

6. The method of claim 1, wherein said subject's pre-administration absolute basophil count is at least 5, at least 10, at least 15, at least 20, at least 25, at least 30, at least 50, at least 60, at least 70, at least 100, at least 200, at least 300, at least 400, or at least 500 basophils/mm$^3$.

\* \* \* \* \*